(12) United States Patent
Opstelten et al.

(10) Patent No.: US 7,304,031 B2
(45) Date of Patent: Dec. 4, 2007

(54) METHODS AND MEANS FOR PRODUCING PROTEINS WITH PREDETERMINED POST-TRANSLATIONAL MODIFICATIONS

(75) Inventors: Dirk Jan Elbertus Opstelten, Oegstgeest (NL); Johan Christiaan Kapteyn, Wageningen (NL); Petrus Christianus Johannes Josephus Passier, Driebergen (NL); Ronald Hendrik Peter Brus, Voorschoten (NL); Abraham Bout, Moerkapelle (NL)

(73) Assignee: Crucell Holland B.V., Leiden (NL)

( * ) Notice: Subject to any disclaimer, the term of this patent is extended or adjusted under 35 U.S.C. 154(b) by 546 days.

(21) Appl. No.: 10/494,140

(22) PCT Filed: Oct. 29, 2002

(86) PCT No.: PCT/NL02/00686

§ 371 (c)(1),
(2), (4) Date: Apr. 29, 2004

(87) PCT Pub. No.: WO03/038100

PCT Pub. Date: May 8, 2003

(65) Prior Publication Data

US 2005/0164917 A1     Jul. 28, 2005

(30) Foreign Application Priority Data

Oct. 29, 2001    (WO)   ................... PCT/NL01/00792
Apr. 19, 2002    (WO)   ................... PCT/NL02/00257

(51) Int. Cl.
*A61K 38/00*    (2006.01)
*C07K 14/505*    (2006.01)

(52) U.S. Cl. .................. 514/2; 530/397; 530/399
(58) Field of Classification Search ............ None
See application file for complete search history.

(56) References Cited

U.S. PATENT DOCUMENTS 5,789,247 A    8/1998    Ballay et al.
7,138,371 B2 *   11/2006    DeFrees et al. ............ 514/8
2002/0058313 A1 *   5/2002    Renkonen et al. .......... 435/105
2002/0116723 A1    8/2002    Grigliatti et al.

FOREIGN PATENT DOCUMENTS

WO    WO 98 44141    10/1998
WO    WO 00 63403 A    10/2000
WO    WO 03 003810 A1    5/2003

OTHER PUBLICATIONS

Wells, Additivity of Mutational Effects in Proteins. Biochemistry 29:8509-8517 (1990).*
Pazur et al., Abstract, Oligosaccharides as immunodeterminants of erythropoietin for two sets of anti-carbohydrate antibodies, Journal of Protein Chemistry, Nov. 2000, pp. 631-635, vol. 19, No. 8.
Cronan, Abstract, Biotination of Proteins in-vivo a post-translational modification to label purify and study proteins, Journal of Biological Chemistry, Jun. 25, 1990, pp. 10327-10333, vol. 265, No. 18.
Stockwell et al., High-throughput screening of small molecules in Miniaturized Mammalian Cell-based Assays involving Post-translational Modifications, Chemistry and Biology, Feb. 1999, pp. 71-83, vol. 6, No. 2.

* cited by examiner

*Primary Examiner*—Marianne P. Allen
*Assistant Examiner*—Regina M. DeBerry
(74) *Attorney, Agent, or Firm*—TraskBritt

(57) ABSTRACT

Described are methods for identifying, selecting, and obtaining mammalian cells capable of producing proteinaceous molecules having predetermined post-translational modifications, wherein the post-translational modifications are brought about by the mammalian cell in which the proteinaceous molecule is expressed. Preferably, the predetermined post-translational modifications include glycosylation. Also described are methods for obtaining and producing proteinaceous molecules, using mammalian cells obtainable by a method of the present invention. Preferably, the proteinaceous molecules includes erythropoietin (EPO), since EPO's effect depends heavily on its glycosylation pattern. Mammalian cells that have been obtained on the basis of their ability to produce proteins and/or post-translational modifications that are indicative for a predetermined post-translational modification that is desired are also provided. Preferably, the mammalian cells have neural characteristics and properties such that significant amounts of recombinant proteins can be produced that harbor 'neural- or brain-type' properties.

4 Claims, 42 Drawing Sheets

◆ Sialic acid

● Galactose

■ N-acetyl-glucosamine

▷ Fucose

R   N-linked sugar substructure

Fraction 1

Fraction 2

Figure 10A:
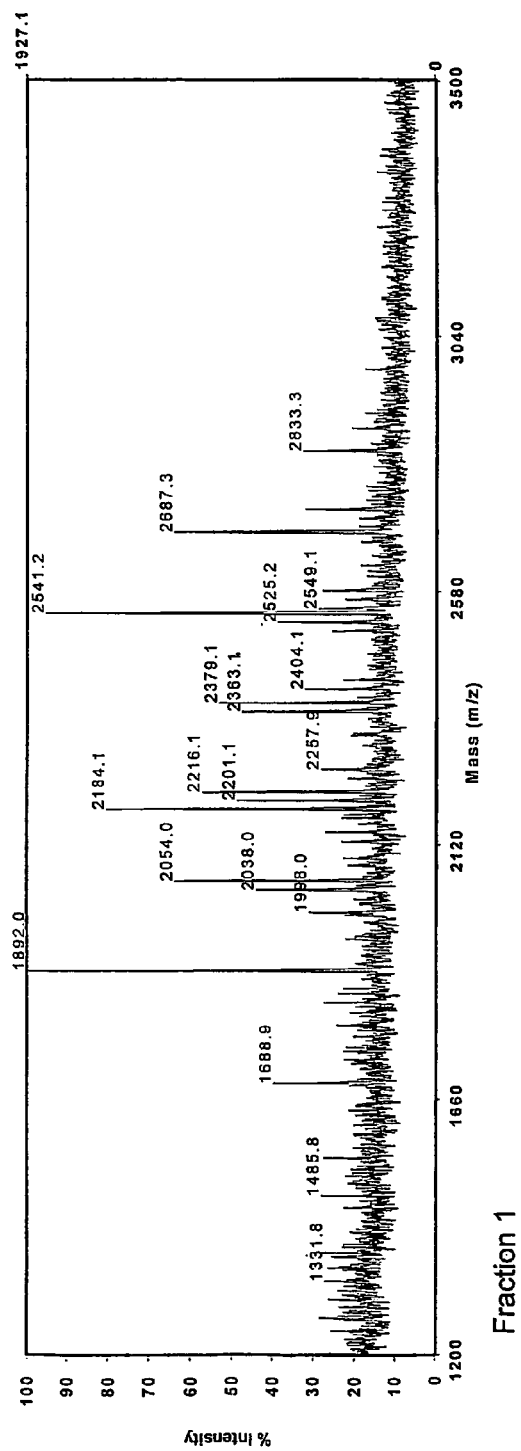
Figure 10A:
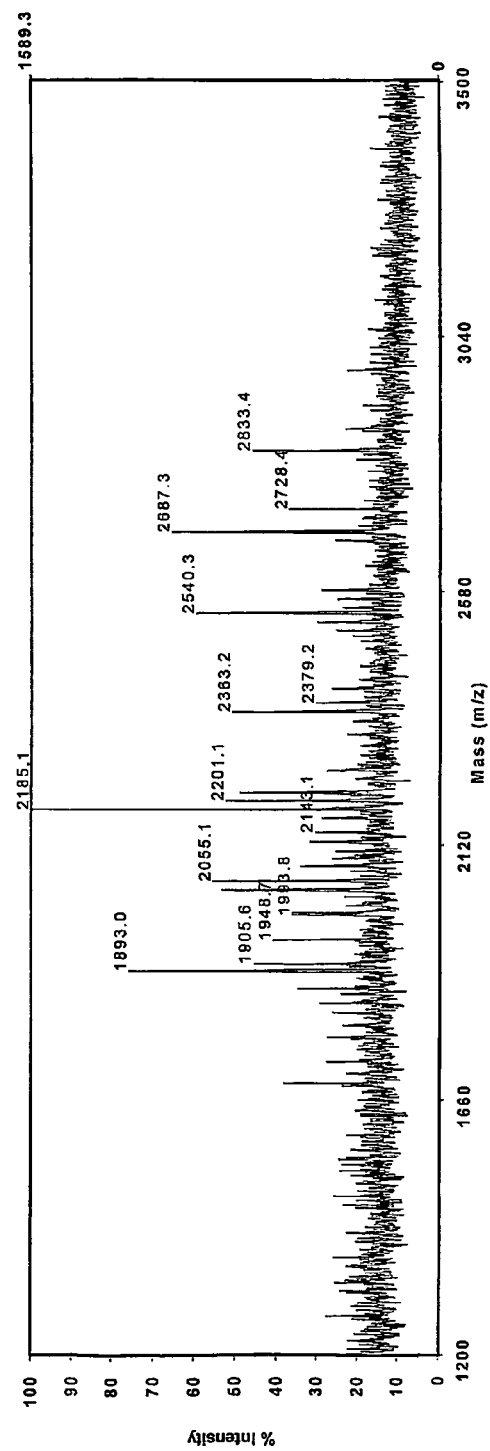

Fig. 10A, contd.
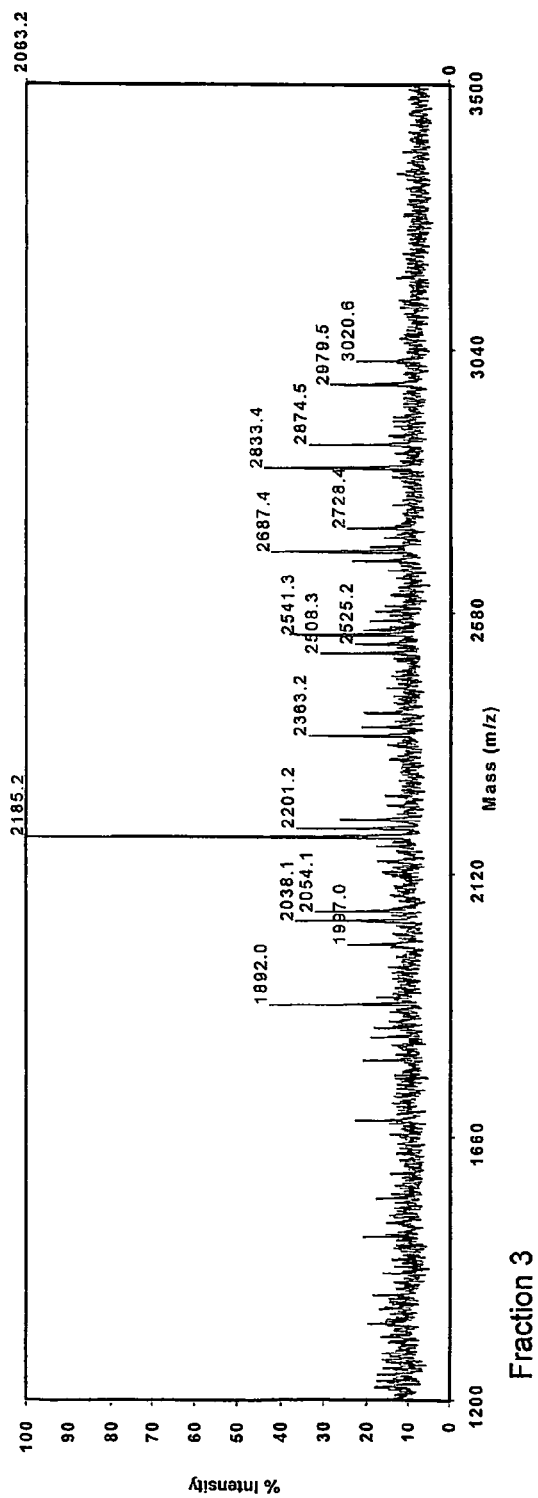
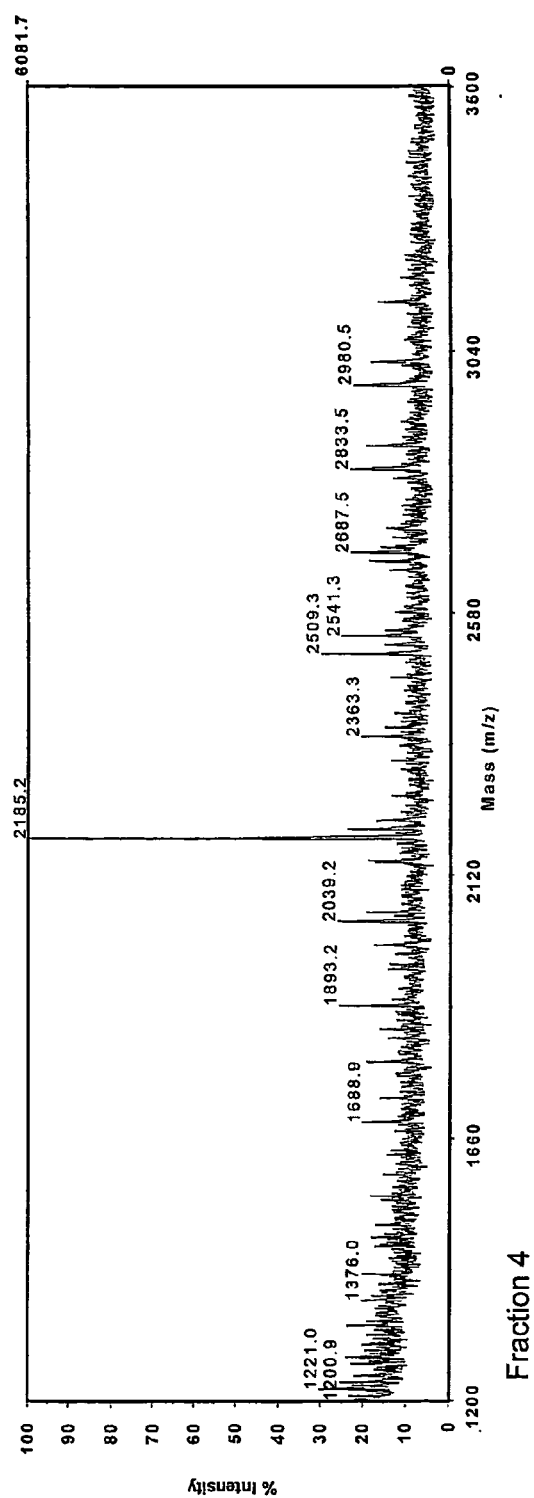

Figure 13:
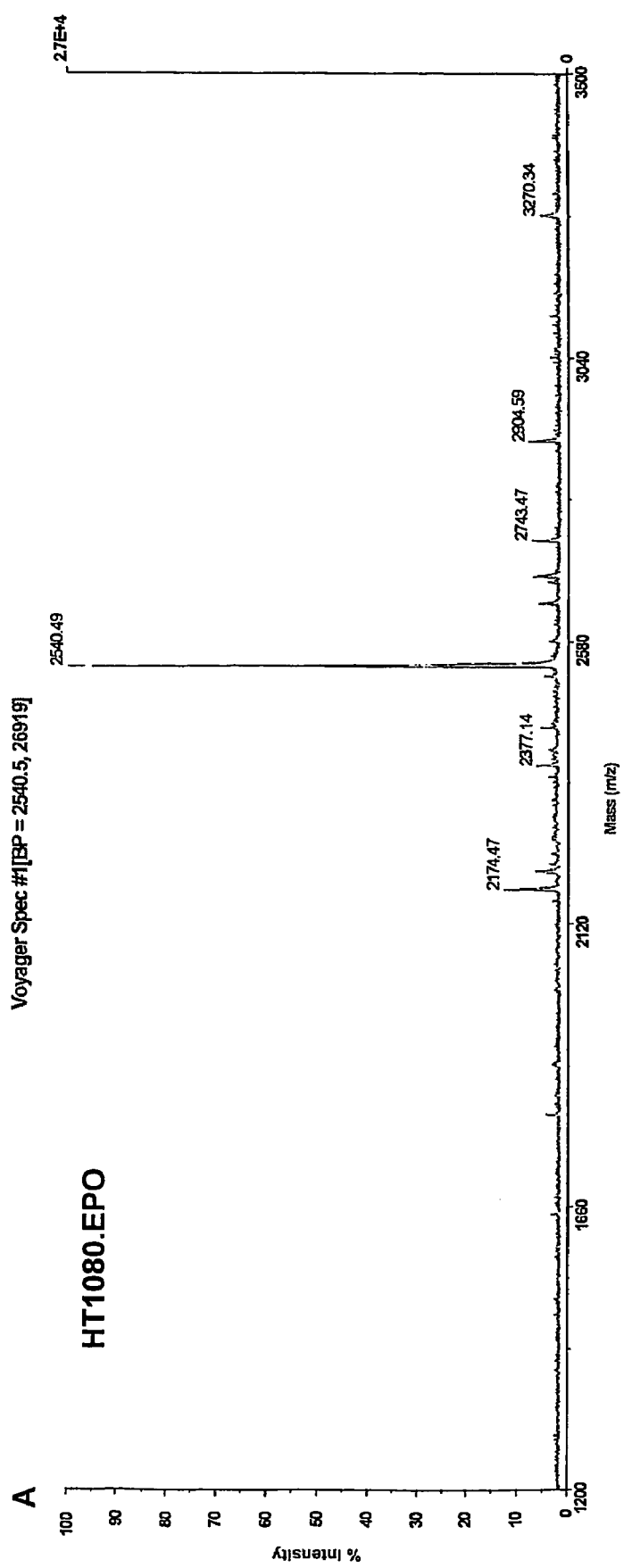

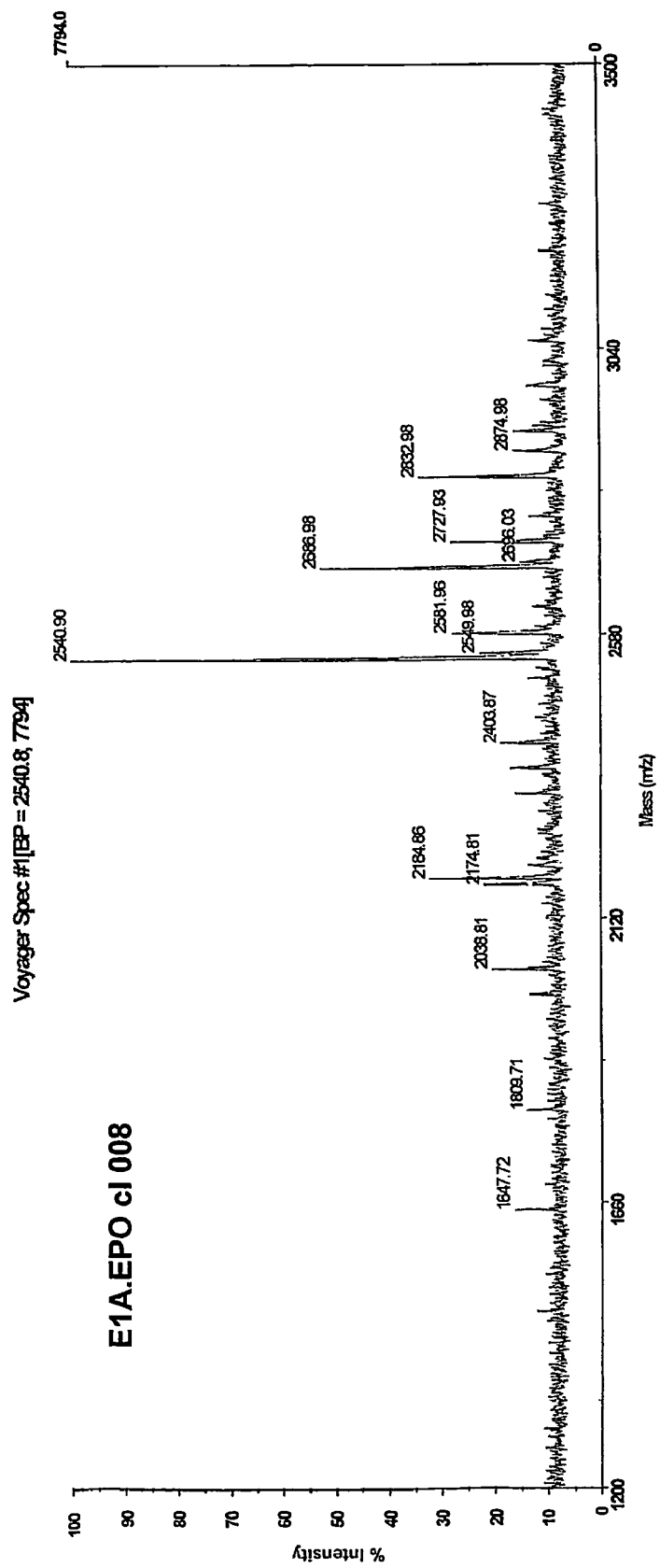
Fig. 13, contd.

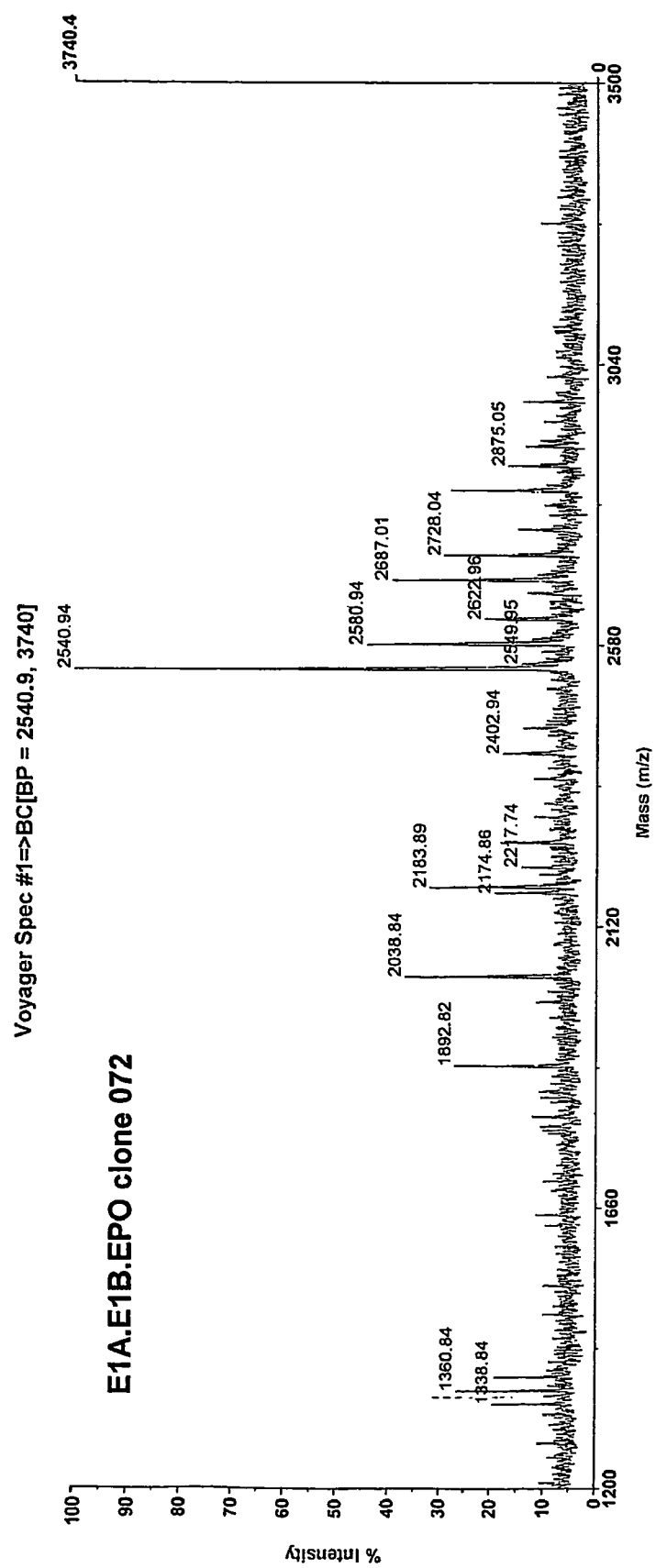
Fig. 13, contd.

Figure 26:
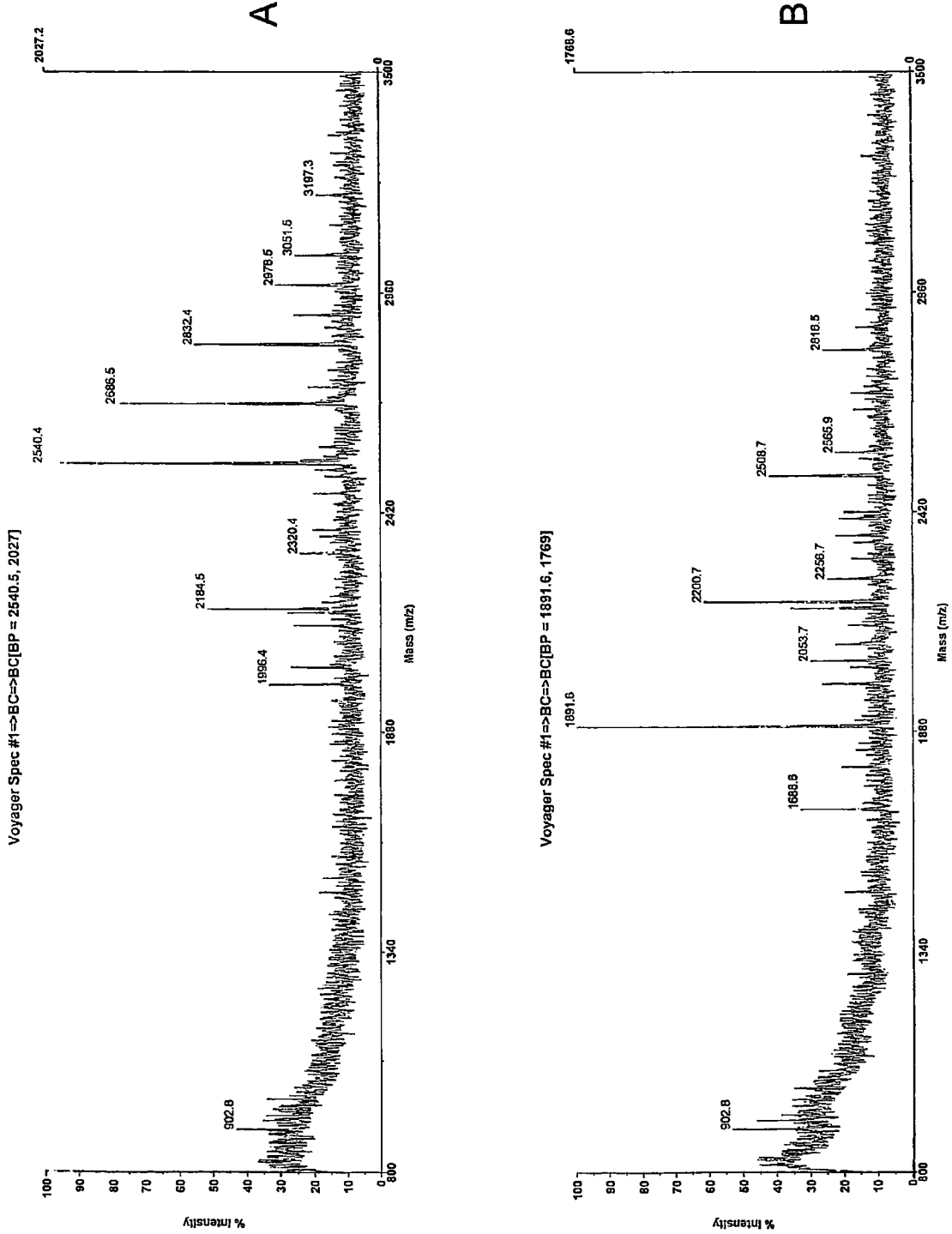

Fig. 26, contd.
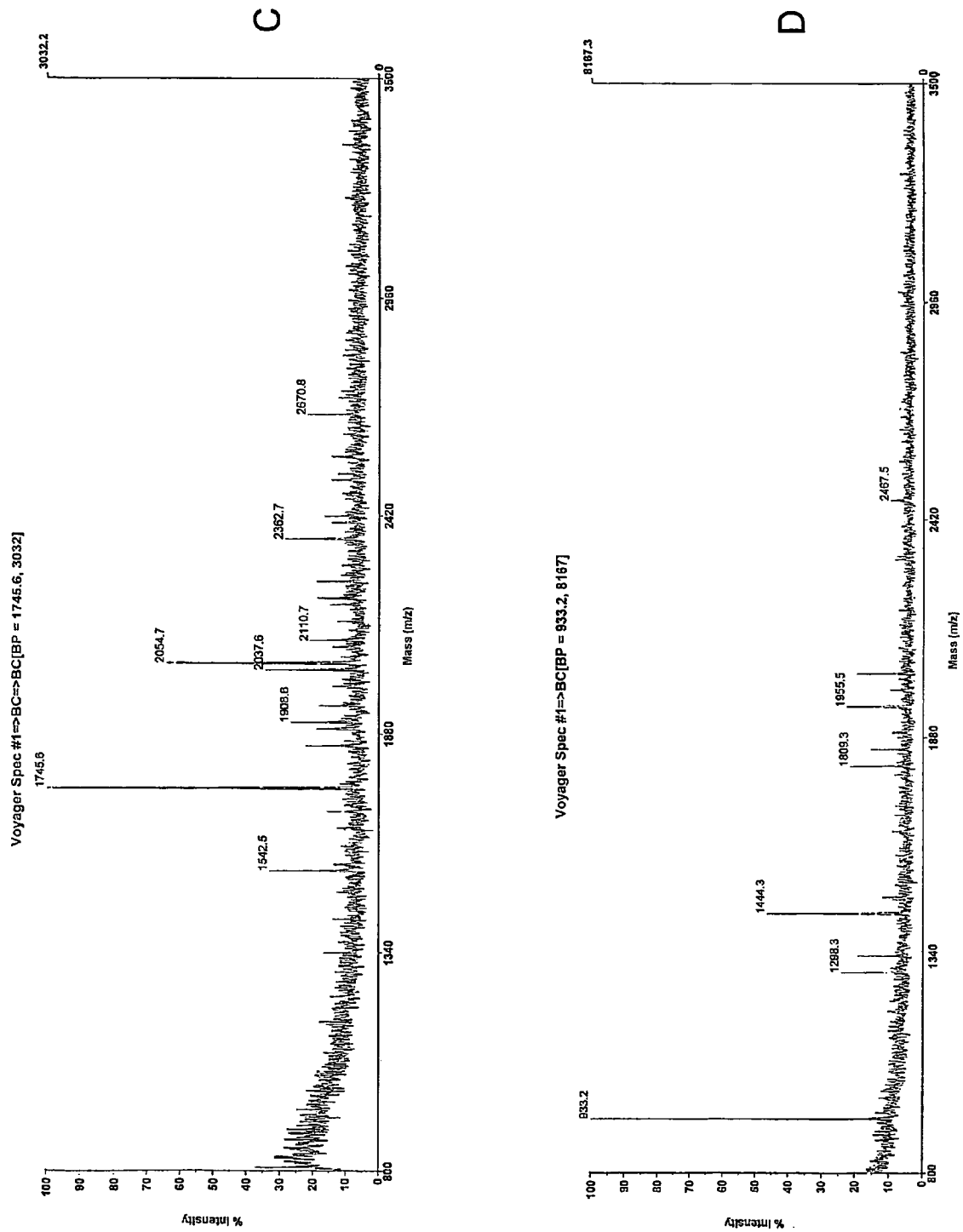

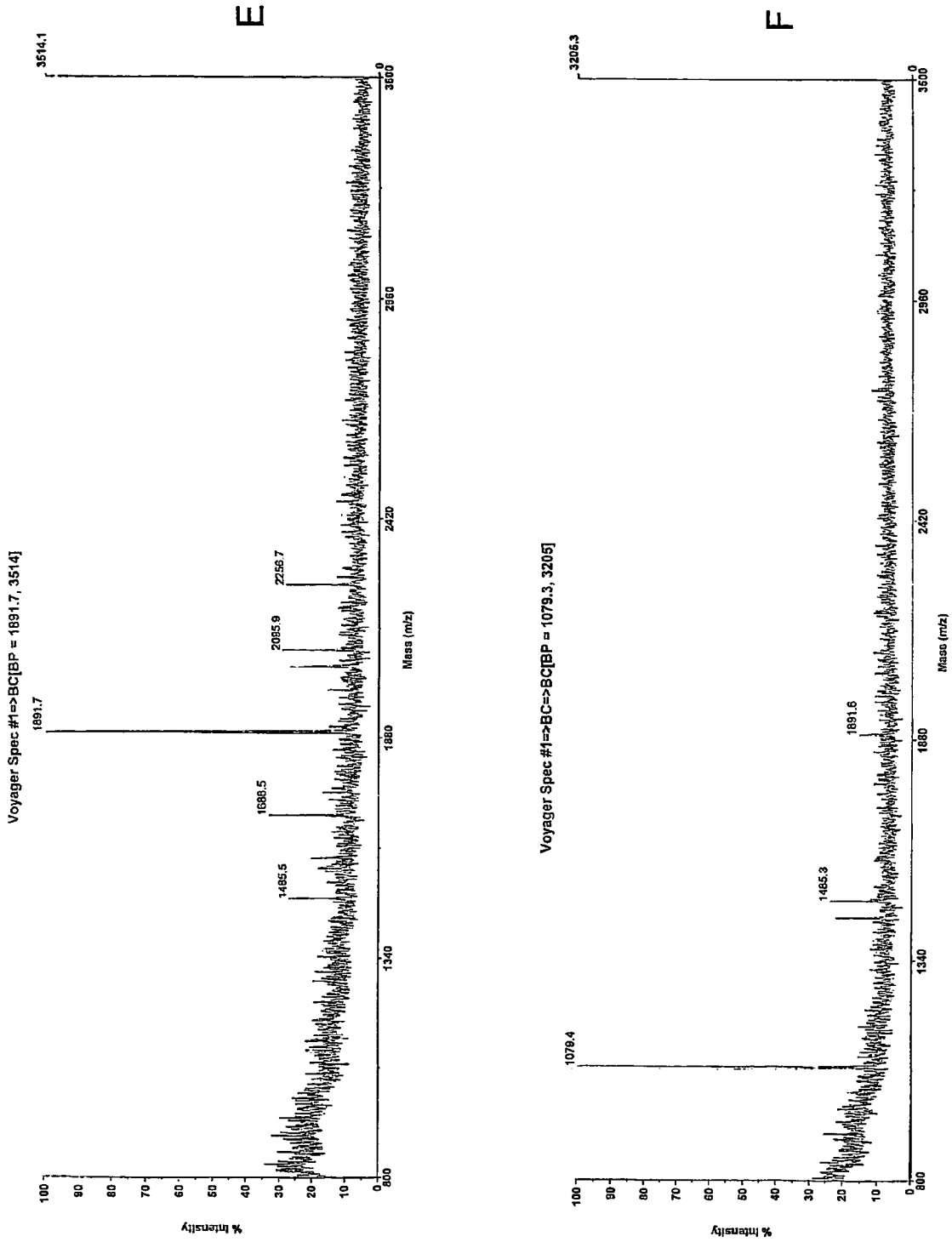
Fig. 26, contd.

METHODS AND MEANS FOR PRODUCING PROTEINS WITH PREDETERMINED POST-TRANSLATIONAL MODIFICATIONS

CROSS-REFERENCE TO RELATED APPLICATIONS

This application is a national entry under 35 U.S.C. § 371 of international application PCT/NL02/00686, filed Oct. 29, 2002, published in English as international publication WO 03/038100 May 8, 2003, the entirety of which is incorporated by reference.

FIELD OF THE INVENTION

The invention relates to the field of recombinant DNA technology. The invention further relates to the production of proteins. More particularly the present invention relates to the production of recombinant proteins for use as a therapeutically active constituent of a pharmaceutical preparation. The invention also relates to mammalian cell lines, identified, selected and/or created for the recombinant production of proteins. The invention further relates to the use of proteins so produced.

BACKGROUND OF THE INVENTION

Recombinant cellular expression systems for the production of proteins are known. These systems range from bacteria, yeast and fungi to plant cells, and from insect cells to mammalian cells. The choice for the production host and expression system generally depends on considerations such as the ease of use, cost of culturing, growth characteristics, production levels and the ability to grow on serum-free medium. It is known that the cellular expression systems mentioned above also differ in the capacity to exert co- and post-translation modifications such as folding, phosphorylation, γ-carboxylation, and γ-hydroxylation. Despite the recognition that the choice of Despite the recognition that the choice of the recombinant expression system may have dramatic consequences on the ultimate structure of the expressed proteins, post-translational modifications have in general not played a decisive role in selecting a suitable expression system for a given protein.

In the last number of years, studies have revealed more about the complexities of differential post-translational modifications of human proteins and the potential implications on functions in the human body. For example, relatively recent findings suggest that differential glycosylation patterns of human proteins that occur in the blood (so-called 'serum-type' modifications) are different from the ones that occur in the cerebrospinal fluid in the brain ('brain-type' modifications). This difference may be a key issue that is of paramount importance for the design of effective therapeutics.

Figure 5:
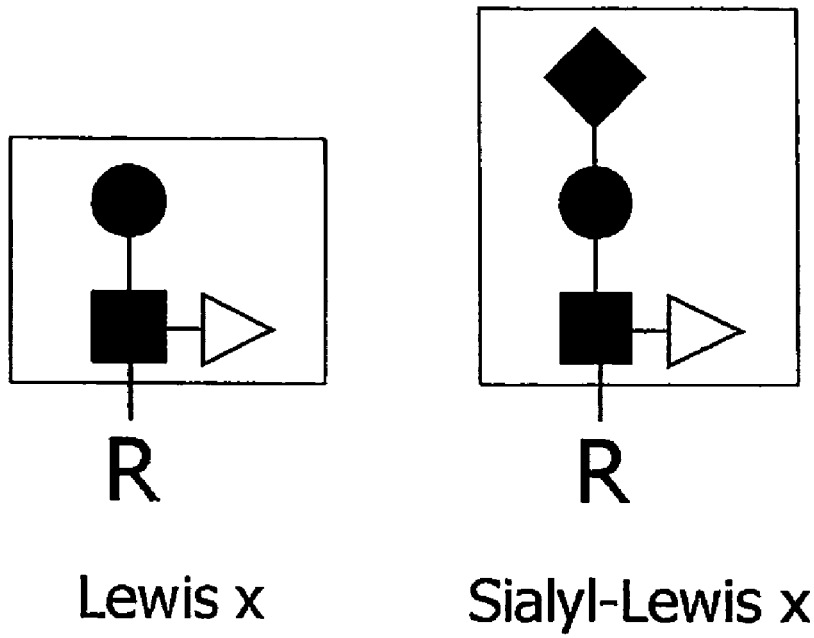

In general, human neural glycoproteins are characterized by their glycosylation, which has been referred to in literature as 'brain-type' glycosylation (Margolis and Margolis 1989; Hoffmann et al. 1994). In contrast to 'serum-type' glycosylated proteins (i.e., glycoproteins circulating in the blood) brain-type glycosylated proteins characteristically possess complex-type N-linked sugars that are modified with α1,3-linked fucose attached to N-acetyl-glucosamine in lactosamine-type antennae thereby forming Lewis x or sialyl-Lewis x structures (FIG. 5). There are two types of Lewis x structures: One with a terminal galactose residue and one with a terminal N-acetyl-galactosamine (GalNac) residue. If these terminal groups are linked to a sialic acid, the Lewis x structure is called a sialyl Lewis x structure. Another difference between serum-type and brain-type oligosaccharides is that the latter often contain terminal N-acetyl-glucosamine and/or terminal galactose, and may include a terminal N-acetyl-galactosamine modification, whereas serum-type oligosaccharides usually contain only low amounts of such structures.

Oligosaccharides that are generally found on proteins circulating in the serum often contain heavily galactosylated structures. This means that a galactose is linked to a peripheral N-acetyl-glucosamine thereby forming a lactosamine structure. The glycoprotein is in this way protected from endocytosis by the N-acetyl-glucosamine receptors (i.e., receptors that recognize terminal N-acetyl-glucosamine) present in hepatic reticuloendothelial cells and macrophages (Anchord et al. 1978; Stahl et al. 1978). Serum-type oligosaccharides usually also contain terminal sialic acids (also often referred to as neuraminic acid) which protect the glycoprotein from clearance through the asialoglycoprotein receptor. These clearance mechanisms specifically apply to glycoproteins circulating in the blood and are probably lacking in the human central nervous system (CNS) (Hoffmann et al. 1994).

Recombinant expression systems for the production of proteins comprising 'serum-type' modifications are available in the art, as exemplified by Chinese Hamster Ovary (CHO) cells and Baby Hamster Kidney (BHK) cells. For the production of proteins with other modifications, such as 'brain-type' modifications however, no such convenient systems have been described. Hence, there is a need for expression systems that take into account the different post-translational modifications on therapeutic proteins. In particular, a need exists for an efficient expression system for proteins comprising 'brain-type' post-translational modifications.

Proteins that have these specific needs may be beneficial in the treatment of all sorts of disorders, among which are the diseases related to the CNS, the peripheral nervous system and heart tissue. Disorders affecting the CNS encompass different kinds of afflictions such as acute brain damage, neurodegenerative diseases and other dysfunctions such as epilepsy, schizophrenia and mood disorders. Other pathological disorders that might afflict neural cells and tissues are due to injuries that might be a result of hypoxia, seizure disorders, neurotoxin poisoning, multiple sclerosis, hypotension, cardiac arrest, radiation or hypoglycemia. Neural injuries might also occur during surgical procedures such as aneurysm repair or tumor resection.

An example of a protein having different roles which are at least in part related to differences in post-translational modifications, is a hormone known as erythropoietin (EPO). EPO, a protein famous for its role in differentiating hematopoietic stem cells into red blood cells, has several other functions, including functions in neural tissues. A role of EPO in the development of the CNS has been suggested (Dame et al. 2001). EPO protein has also been detected in the cerebrospinal fluid (CSF) of human neonates and adults (Juul et al. 1997; Buemi et al. 2000). EPO as present in the CSF appears to be produced locally in the brain as it does not cross the intact blood-brain barrier (Marti et al. 1997; Buemi et al. 2000). The regulation of EPO expression is tissue-specific, which further strengthens the hypothesis that EPO has tissue-specific functions that are different in the brain and the bone marrow (Masuda et al. 1999; Chikuma et al. 2000; Sasaki et al. 2001). It has therefore been postulated that EPO, in addition to its heamatopoietic function, may have a neurotrophic role. Neurotrophic factors are defined as humoral molecules acting on neurons to influence their development, differentiation, maintenance, and regeneration (Konishi et al. 1993). The results of several studies have now demonstrated that EPO can act as a neurotrophic factor (e.g. Sadamoto et al. 1998; Brines et al. 2000). In addition to the mentioned effects of EPO on erythropoiesis and neuroprotection, other roles of EPO have been described, e.g. in endothelial cells and muscle cells. It has been well established in the art that the effect of (recombinant) EPO depends heavily on the glycosylation pattern of the oligosaccharides present on the protein. The N-linked oligosaccharides of human EPO are highly important for its well-known biological activity: the stimulation of erythropoiesis (Takeuchi and Kobata 1991; Wasley et al. 1991; Tsuda et al. 1990; Morimoto et al. 1996; Takeuchi et al. 1989; Misaizu et al. 1995).

In the case of EPO, one can also refer to a serum-type EPO (or a 'renal-type', or a 'urinary-type' EPO) for the protein that is produced in the kidney and that circulates in the blood, as compared to EPO that is been produced by other tissues such as the brain (brain-type). Production and purification systems for serum-type EPO are well established in the art, and recombinantly produced serum-type EPO is routinely and successfully used for instance in patients suffering from a low red blood cell level. It is well established in the art that this recombinant EPO had to fulfill all requirements of a stable protein that could circulate in the bloodstream for a sufficient amount of time to enable the induction of erythropoiesis. Usually a CHO or BHK based cell system is used for the production of EPO with these characteristics. However, the serum-type EPO resulting from this production and purification system is relatively useless in the treatment of disorders related to the Central- or Peripheral Nervous system as well as in the treatment of afflictions related to ischemia/reperfusion induced disorders. This is because of its glycosylation pattern that is not suited for the treatment of these disorders, and also because it leads to an increase in the number of red blood cells (erythropoiesis) due to its strong hematopoietic activity, which is to be qualified as undesirable side effects in the context of these non-hematopoietic disorders (Wiessner et al, 2001). Hence, a need exists for new production systems for proteins such as EPO, that have the characteristic features of an EPO molecule that is active in the brain or in tissues that involve selectin-based transport or targeting. Furthermore, a need exists for pharmaceutically acceptable preparations of proteins such as EPO, with post-translational modifications that differ from the serum type glycosylation, preferably having a brain-type glycosylation, and efficient production and purification systems to provide for these.

Another example of a protein that has different glycosylation patterns in separate tissues, suggesting a differential role of the different glycosylation patterns, is transferrin, which occurs in significant amounts as asialotransferrin in the CSF but not in that form in serum (Van Eijk et al. 1983; Hoffmann et al. 1995).

A certain family of glycoproteins, named selectins, play an important role in the initial steps of adhesion of leukocytes to the endothelium in ischemia/reperfusion injury. There are three members in the selectin family: P-selectin, E-selectin and L-selectin. Selectins have a lectin domain that recognizes the sugar structures of the glycoprotein ligands binding to them. There is a possible role for the sialyl Lewis x modifications in oligosaccharides in binding to selectins (Foxall et al. 1992). Several studies have indicated the importance of selectins and sialyl Lewis x structures for the adhesion of leukocytes in models of ischemia/reperfusion. The sialyl Lewis x oligosaccharide $Sle^x$-OS was for instance shown to be cardioprotective in a feline model of ischemia/reperfusion by reducing cardiac necrosis by 83% (Buerke et al. 1994). Furthermore, patent application WO 02/38168 describes the use of selectin binding proteins comprising sialyl Lewis x structures for use as anti-inflammatory agents in the treatment of various diseases. However, suitable expression systems for the preparation of proteins comprising (sialyl) Lewis x glycans have not been described. Hence, a need exists for a recombinant expression system for proteins in need of predetermined glycosylation structures, such as (sialyl) Lewis x structures. More in general, there is a need for expression systems for recombinant production of proteins in need of predetermined post-translational modifications.

BRIEF DESCRIPTION OF TABLES AND FIGURES

Table I. Overview of the marker proteins that can be used to characterize cells.

Table II. Positive control tissues that can be used for some of the marker proteins depicted in Table I.

Table III. Detailed information (Supplier and Catalogue numbers) of antibodies directed to marker proteins that were used to characterize the PER.C6™ cell line.

Table IV. Score of the presence of the marker proteins on PER.C6™.

Table V. Monosaccharide composition of the N-linked sugars of PER.C6™-EPO and Eprex.

Table VI. Assignments of MS peaks observed for the molecular ions of desialylated N-glycans released by N-glycanase F from EPO produced in DMEM by EPO producing PER.C6™ clone P7. Peaks with mass (m/z) values that are also found in Eprex are underlined and indicated in bold.

Table VII. Assignments of MS peaks observed for the molecular ions of desialylated N-glycans released by N-glycanase F from EPO produced in DMEM by EPO producing PER.C6™ clone P8. Peaks with mass (m/z) values that are also found in Eprex are underlined and indicated in bold.

Table VIII. FUT activities in CHO and PER.C6™ cells.

Table IX. Assignment of MS peaks observed for the molecular ions of desialylated N-glycans released by N-glycanase F from EPO fractionated on an AAL column to select for high and low fucose content.

Table X. Relative E1A expression and morphology of EPO producing E1A.EPO and E1A.E1B.EPO HT1080 clones. The quantity of E1A expression was assessed by Western blot analysis. Clones marked with * were selected for the EPO production assay.

Table XI. Relative presence of mass profiles of the N-linked sugars of EPO obtained from the HT1080/Epo clone 033, the HT1080/E1A-EPO clone 008, and the HT1080/E1A.E1B-EPO clone 072. The ExPAsy's computer program was used to predict the sugar composition. The number of the hexosamines, hexoses and deoxyhexoses present in the antennae of the glycans and the proposed structures are shown in the table.

FIG. 1. Mass spectra of the N-linked sugars of Eprex, P7-EPO (pools A, B, and C), and P8-EPO (pools A, B, and C). (A) Eprex; (B) P7, pool A; (C) P7, pool B; (D) P7, pool C; (E) P8, pool A; (F) P8, pool B; and (G) P8, pool C.

Figure 1A:
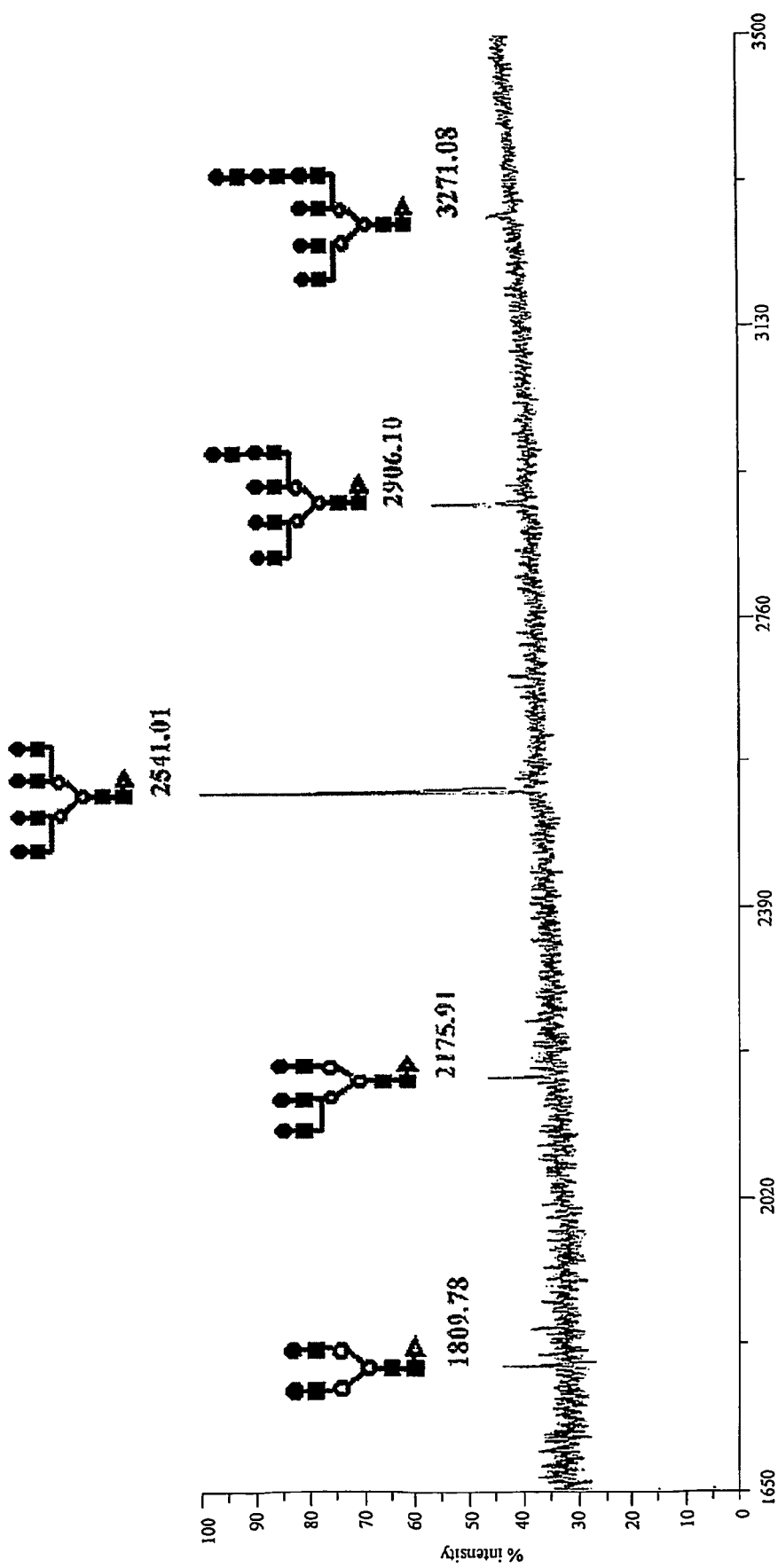
Figure 1B:
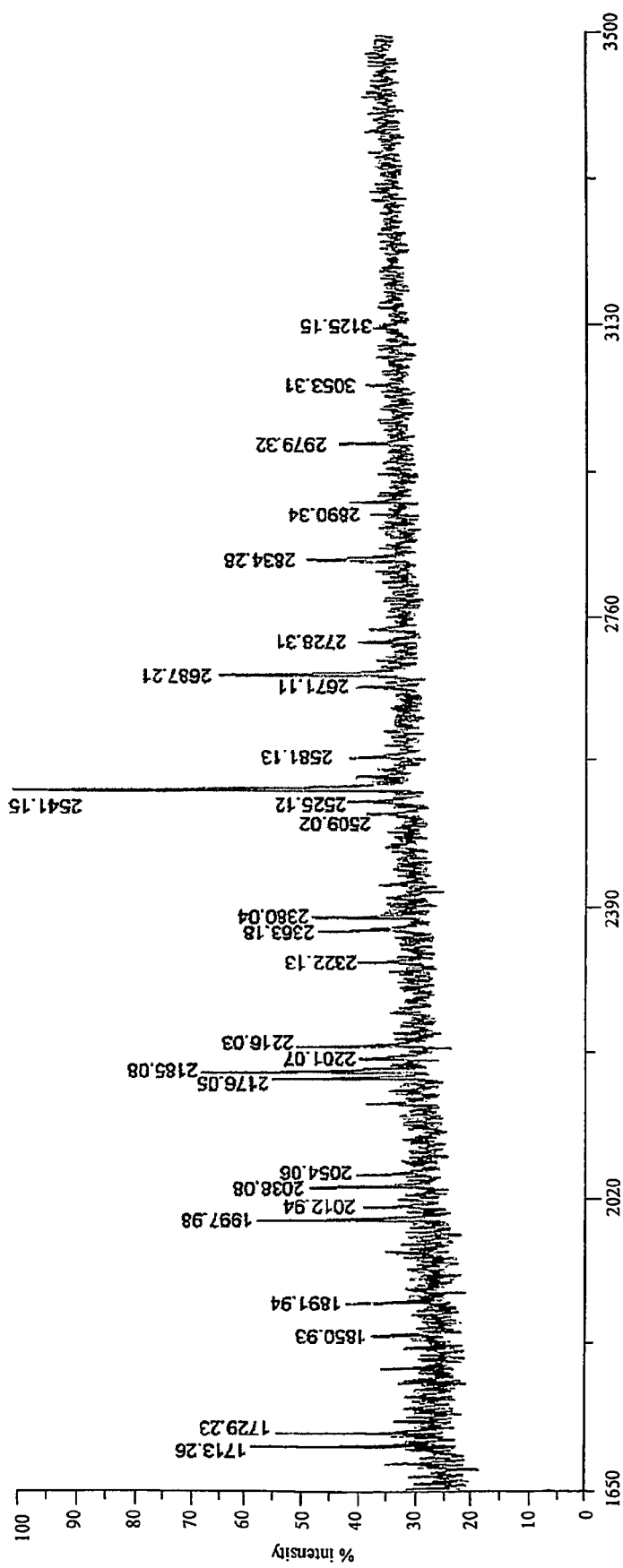
Figure 1C:
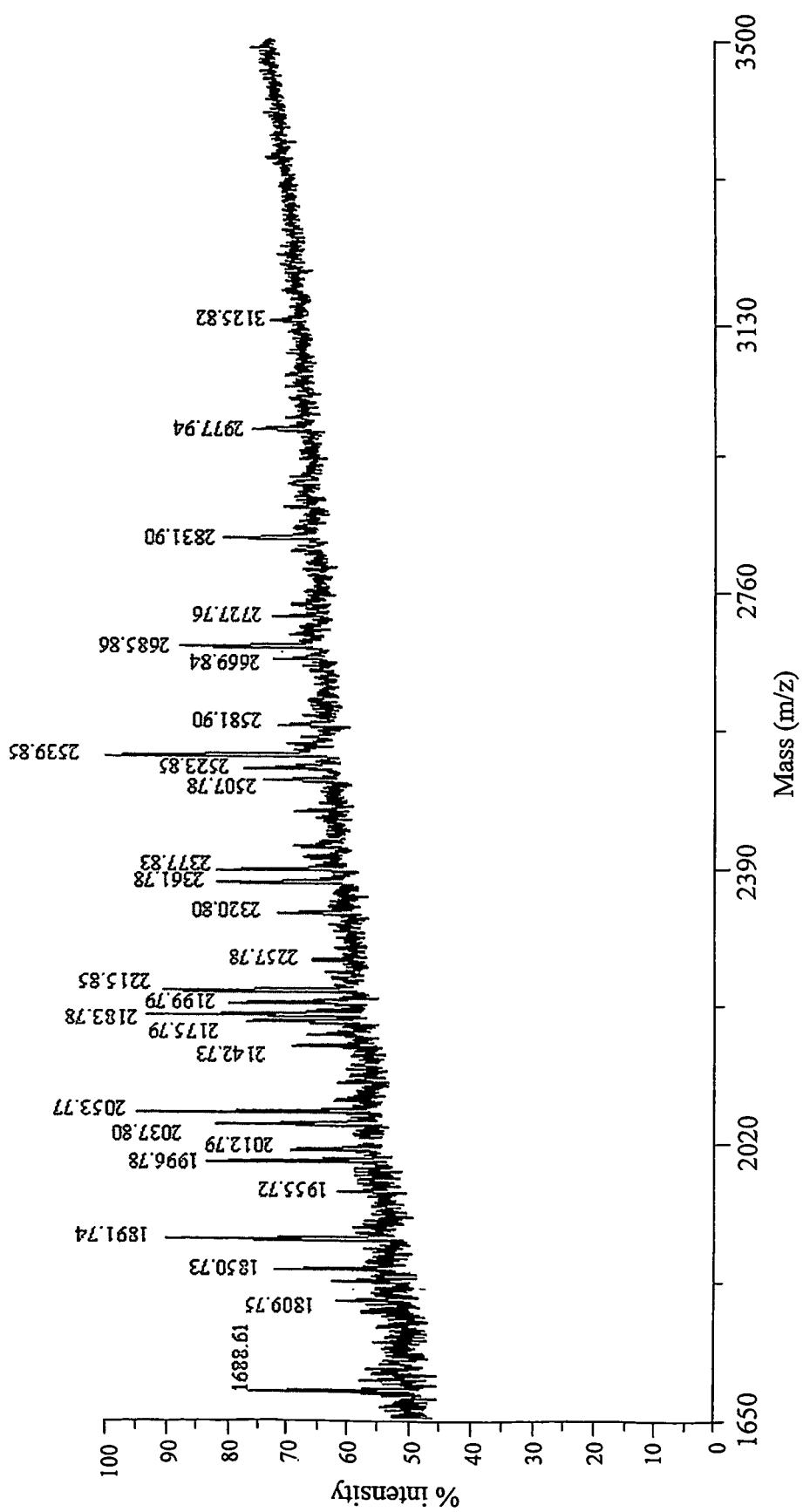
Figure 1D:
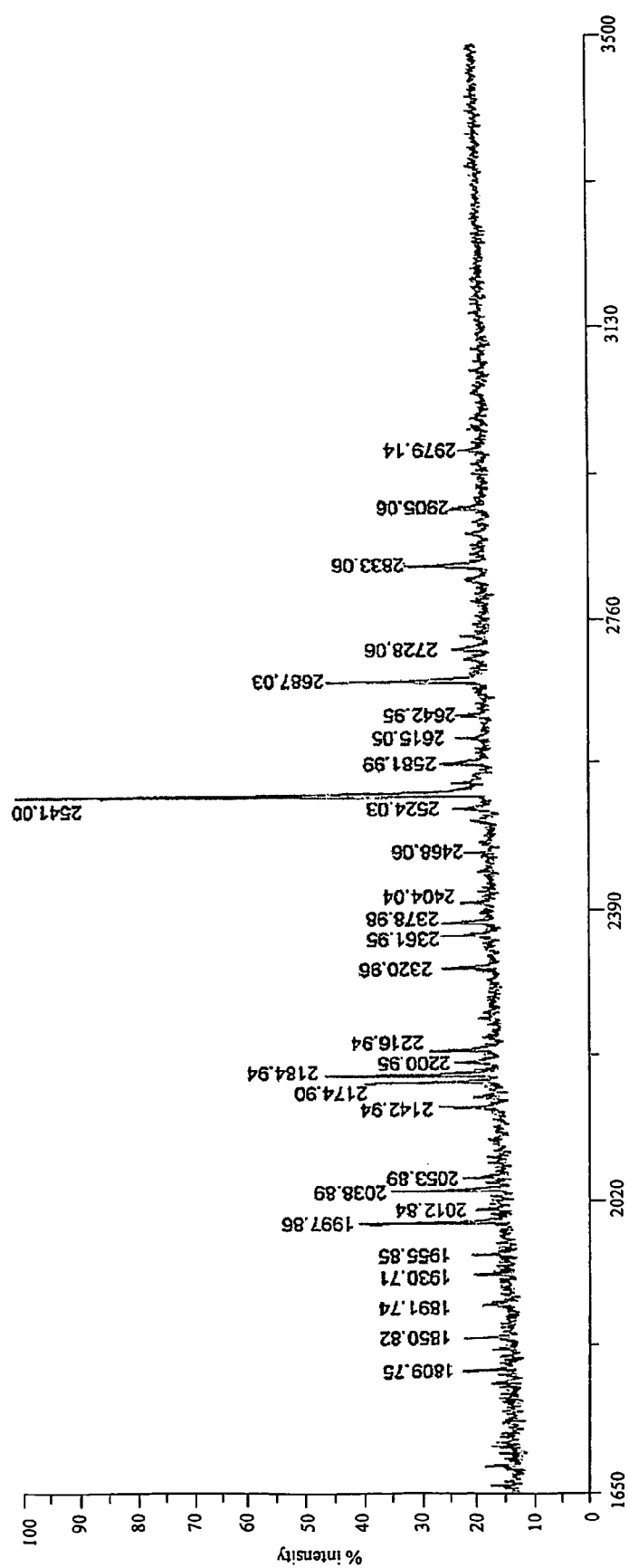
Figure 1E:
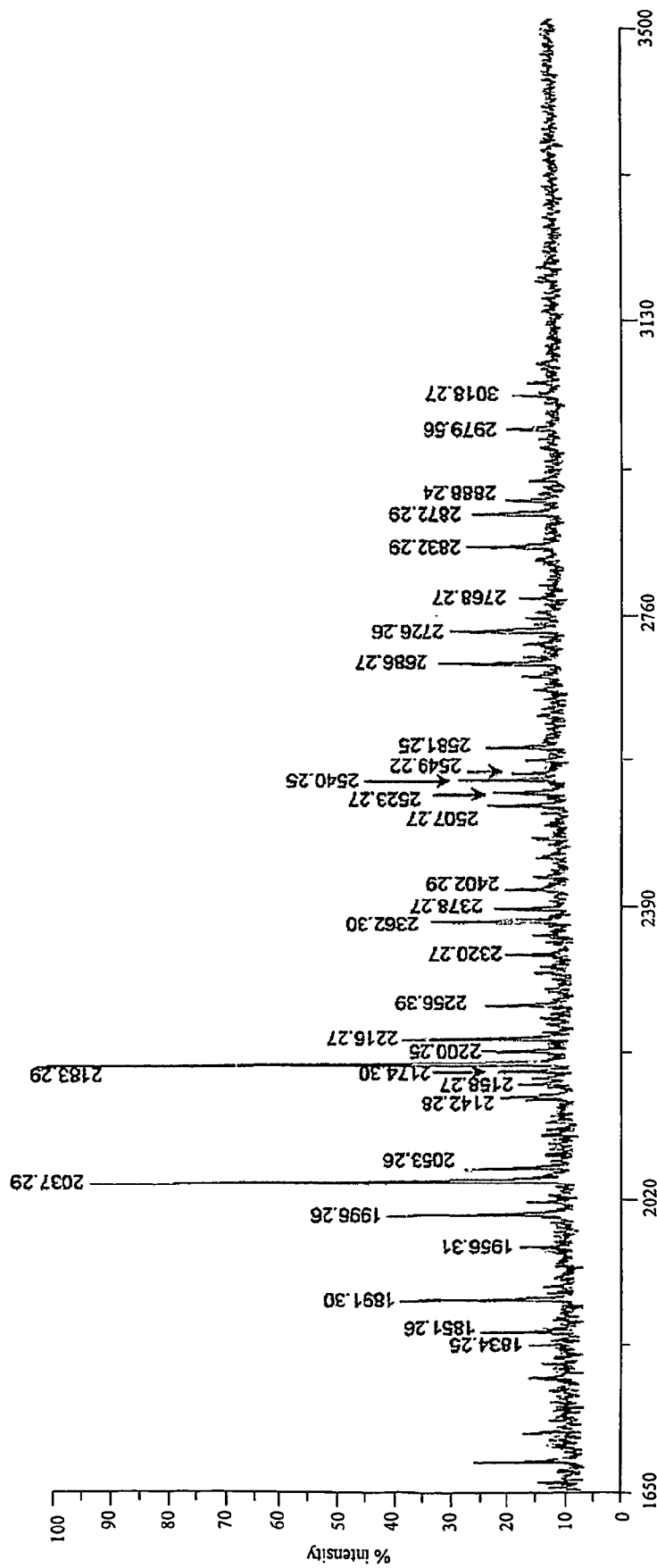
Figure 1F:
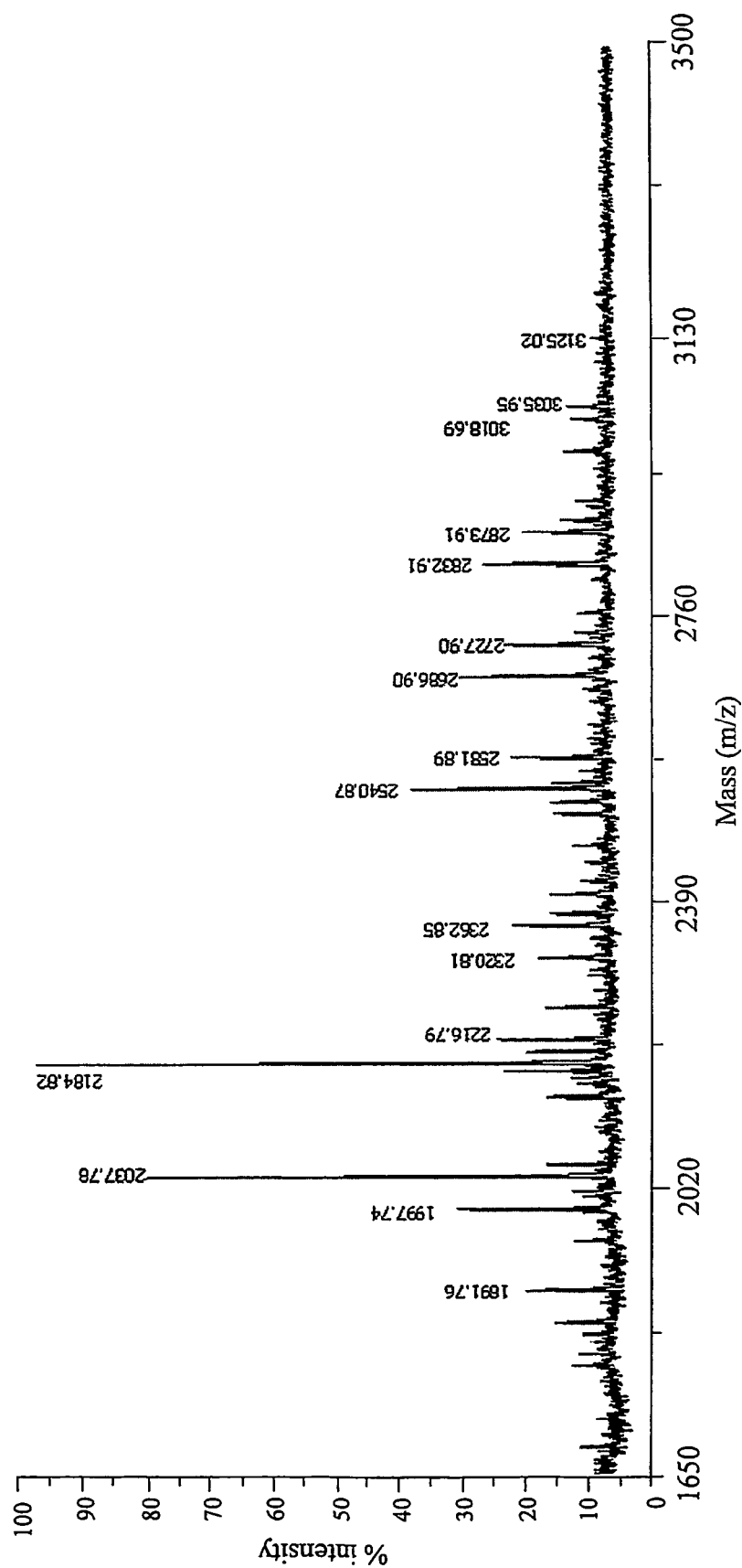
Figure 1G:
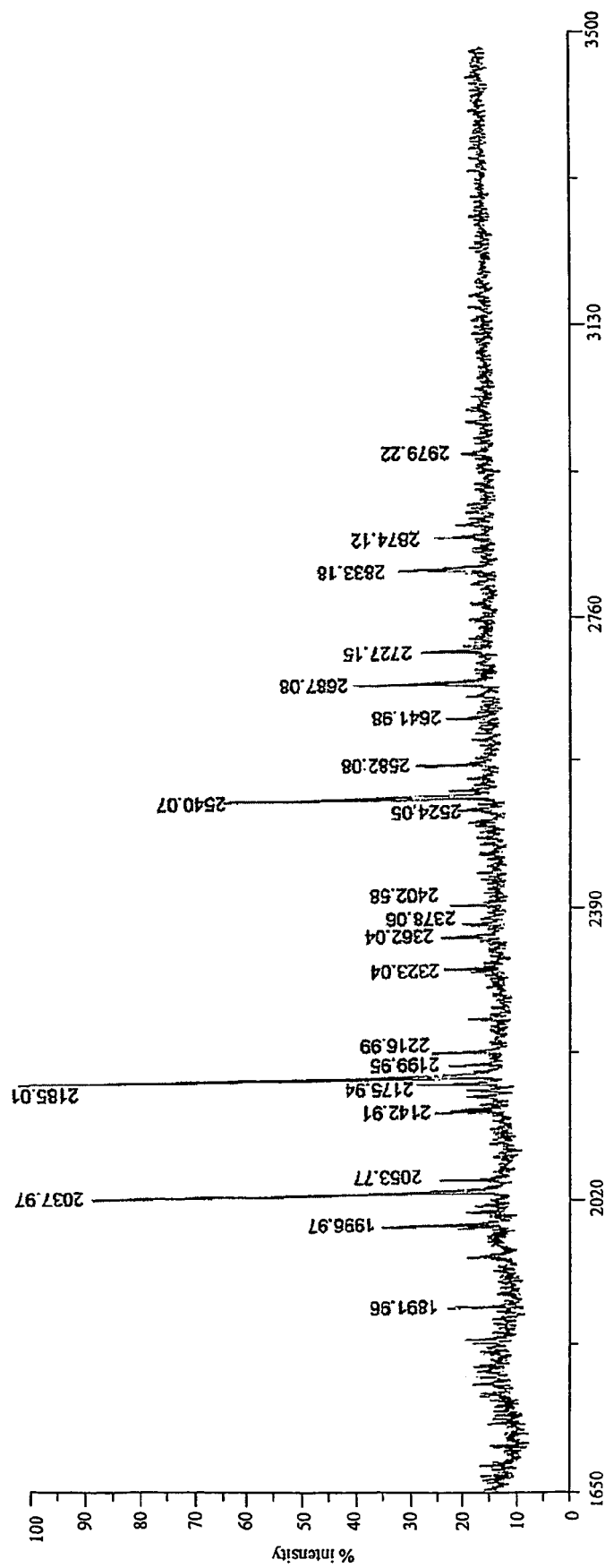
Figure 2:
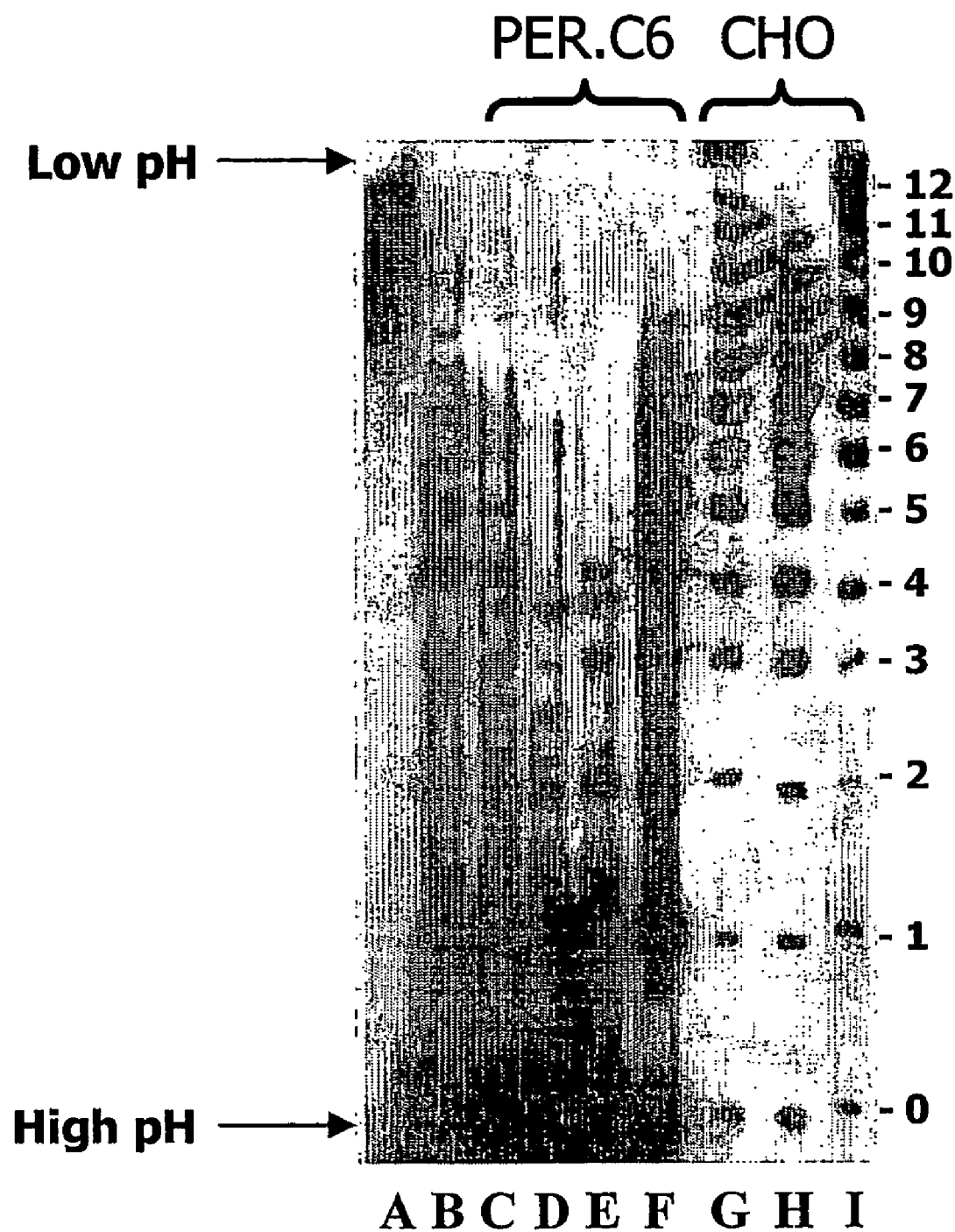

FIG. 2. Sialic acid content of PER.C6™-EPO and CHO-EPO.

Figure 3:

FIG. 3. Lewis x glycan structures present on PER.C6™-EPO.

Figure 4:
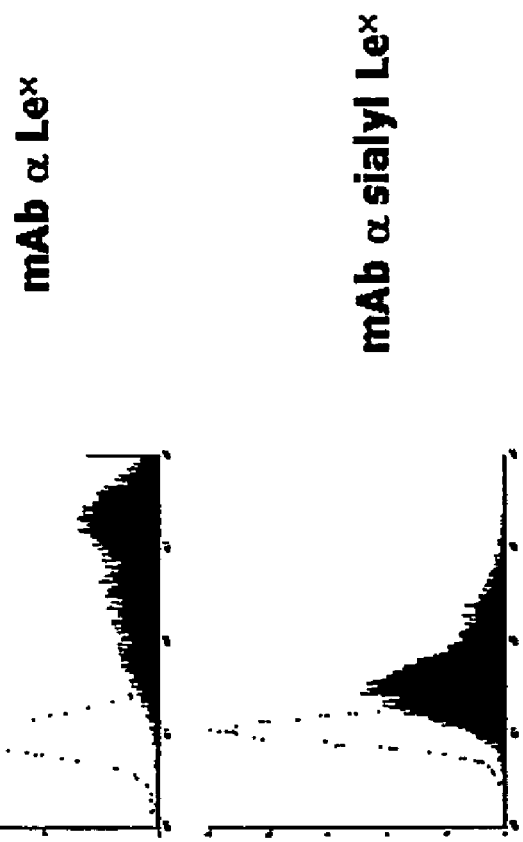
Figure 4:
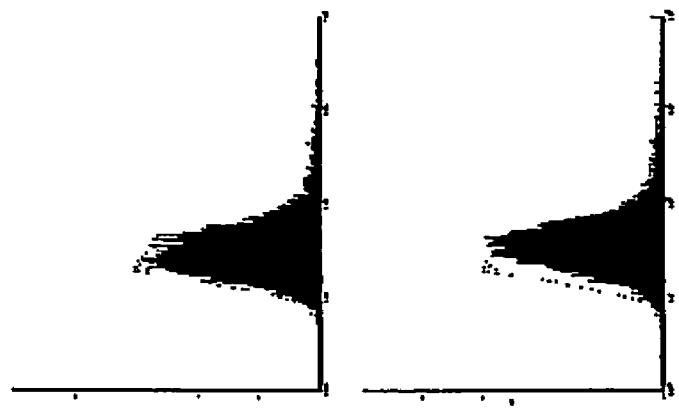

FIG. 4. Lewis x structures expression at the PER.C6™ cell surface.

FIG. 5. Schematic representation of Lewis x and Sialyl Lewis x structures.

Figure 6:
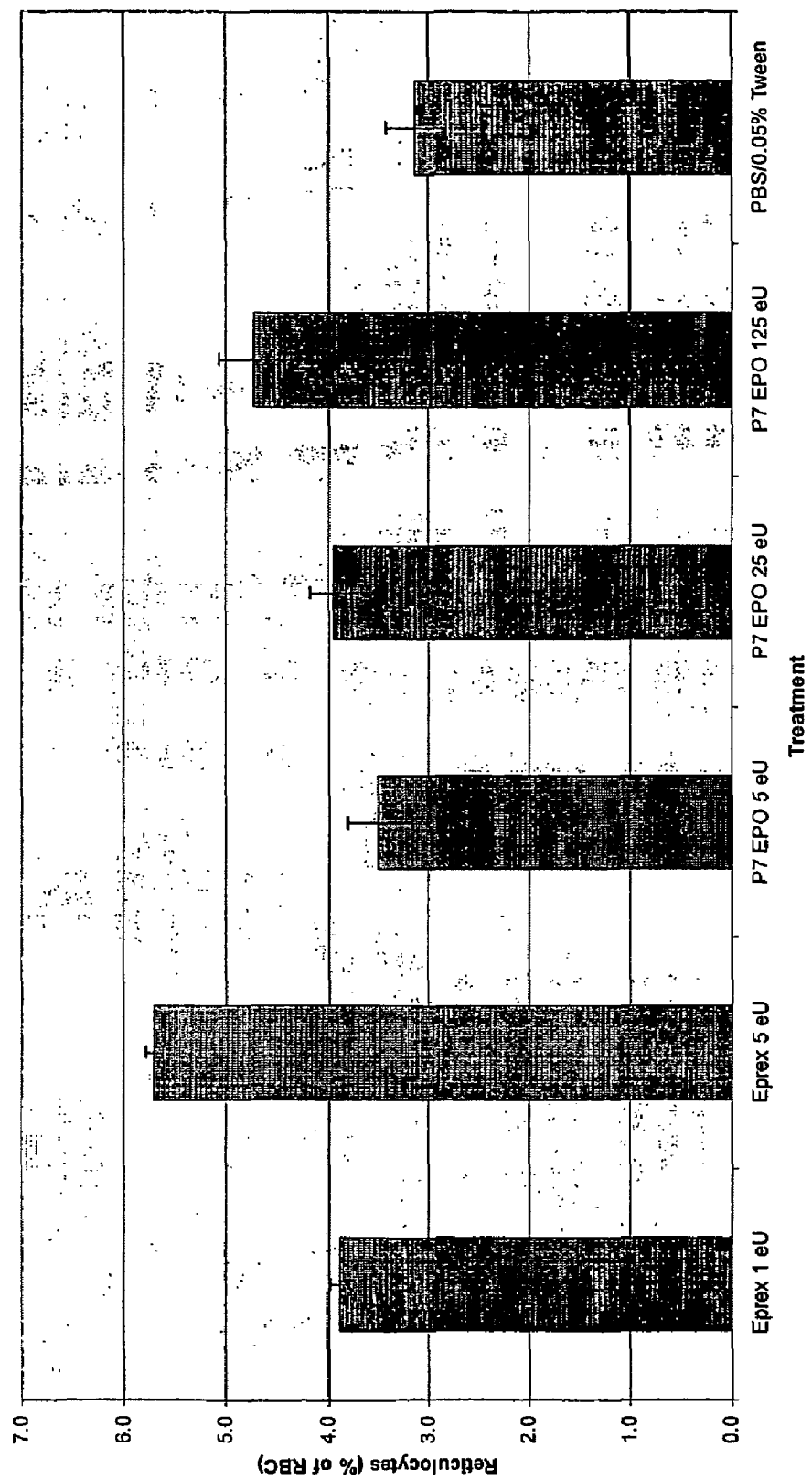

FIG. 6. Effect of PER.C6™-EPO and Eprex on erythropoiesis in vivo.

Figure 7A:
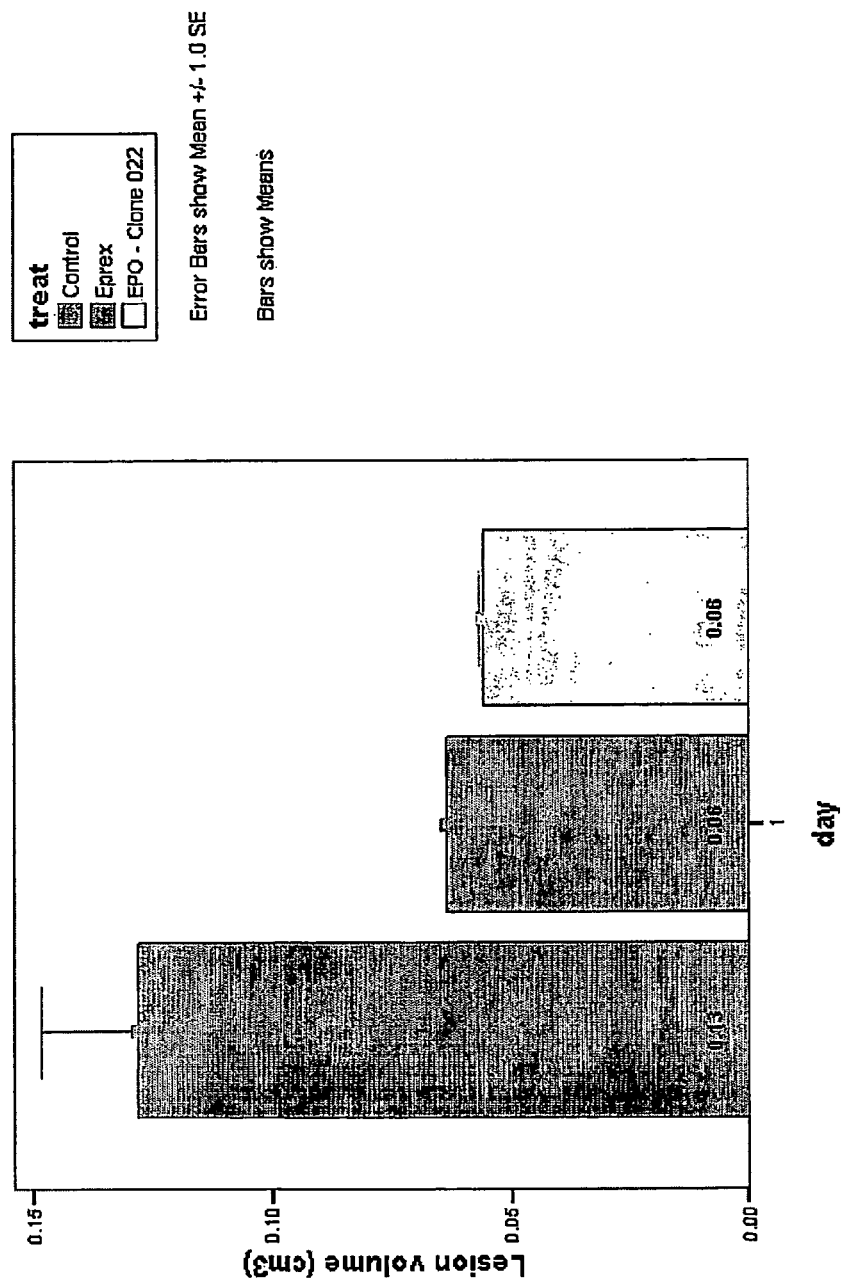
Figure 7B:
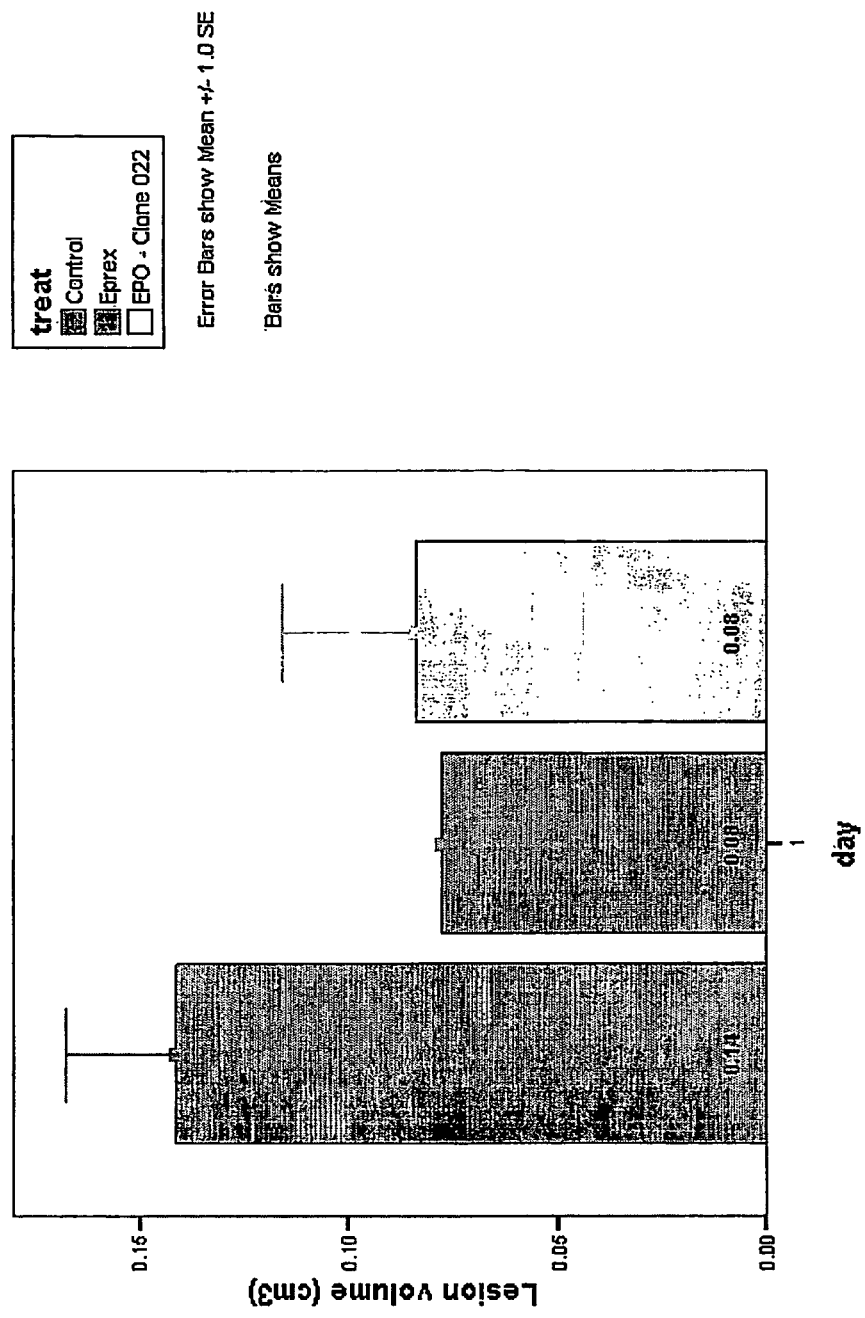

FIG. 7. Infarct volumes in untreated rats (control) and Eprex and PER.C6™-EPO treated rats based on the ADC maps (FIG. 7A) and the T2 maps (FIG. 7B) generated at 24 h after the onset of reperfusion, using MRI.

Figure 8:
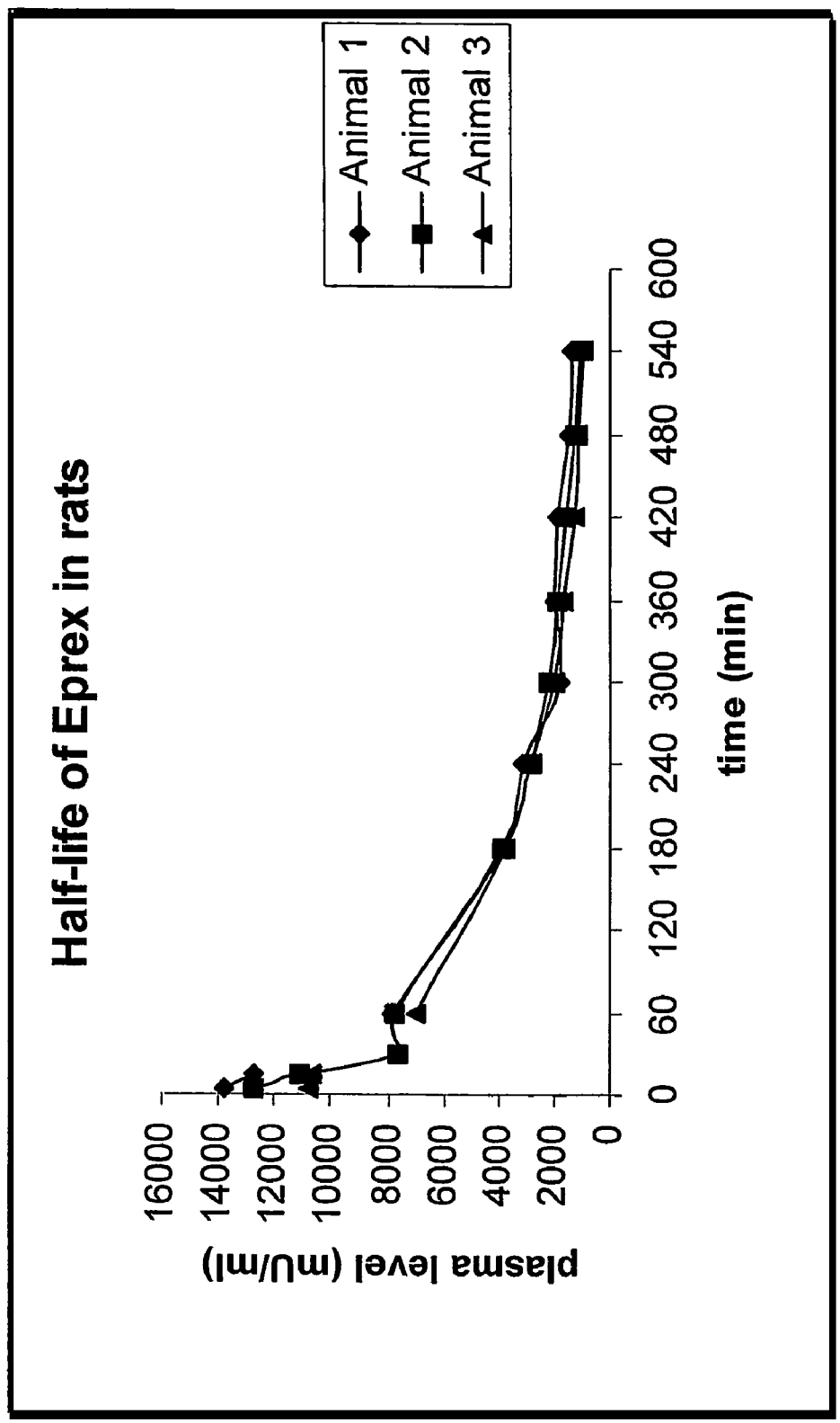

FIG. 8. Concentration of Eprex at the indicated timepoints after a single i.v. injection of 150 eU of Eprex in three animals.

Figure 9:
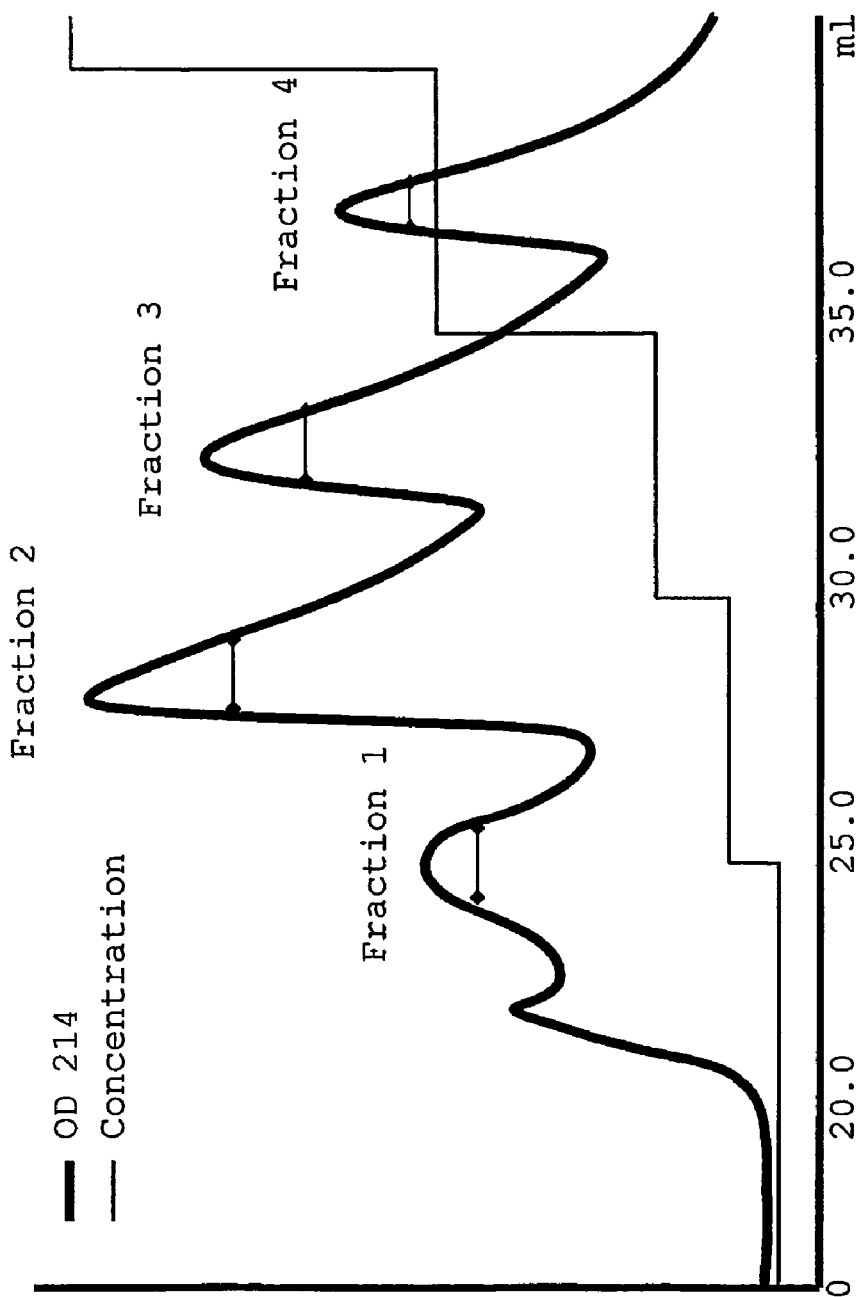

FIG. 9. Chromatogram of PER.C6™ EPO fractionated on an AAL column to select for high and low fucose content.

FIG. 10A. Mass spectra of the N-linked sugars of fraction 1-4 from the AAL column. B. Mass spectrum of the N-linked sugars of fraction 4 from the AAL column in an independent experiment.

Figure 11:
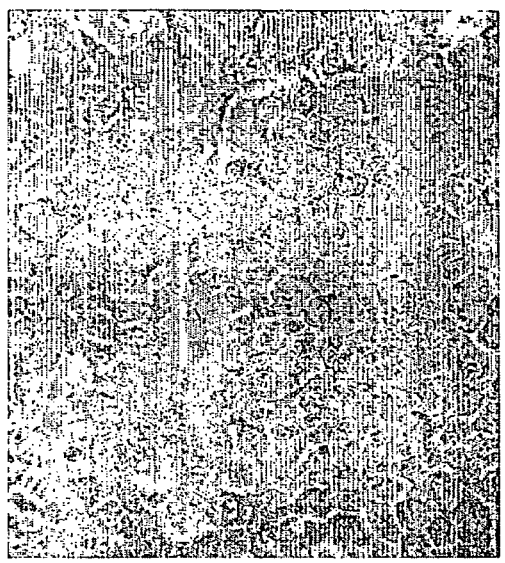
Figure 11:
Figure 11:
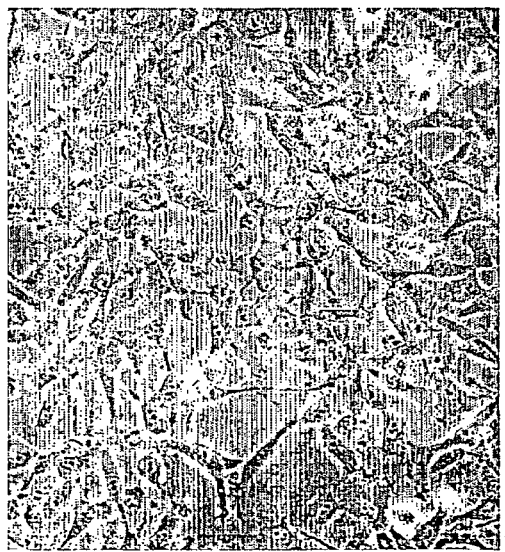
Figure 11:

FIG. 11. Pictures of the HT1080/EPO clone 033 (A) and of the HT1080/E1A.E1B.EPO clone 058 (B) and 026 (C). Their expression of E1A is shown by Western blot analysis (D). The E1A expressing clones have a flat morphology.

Figure 12:
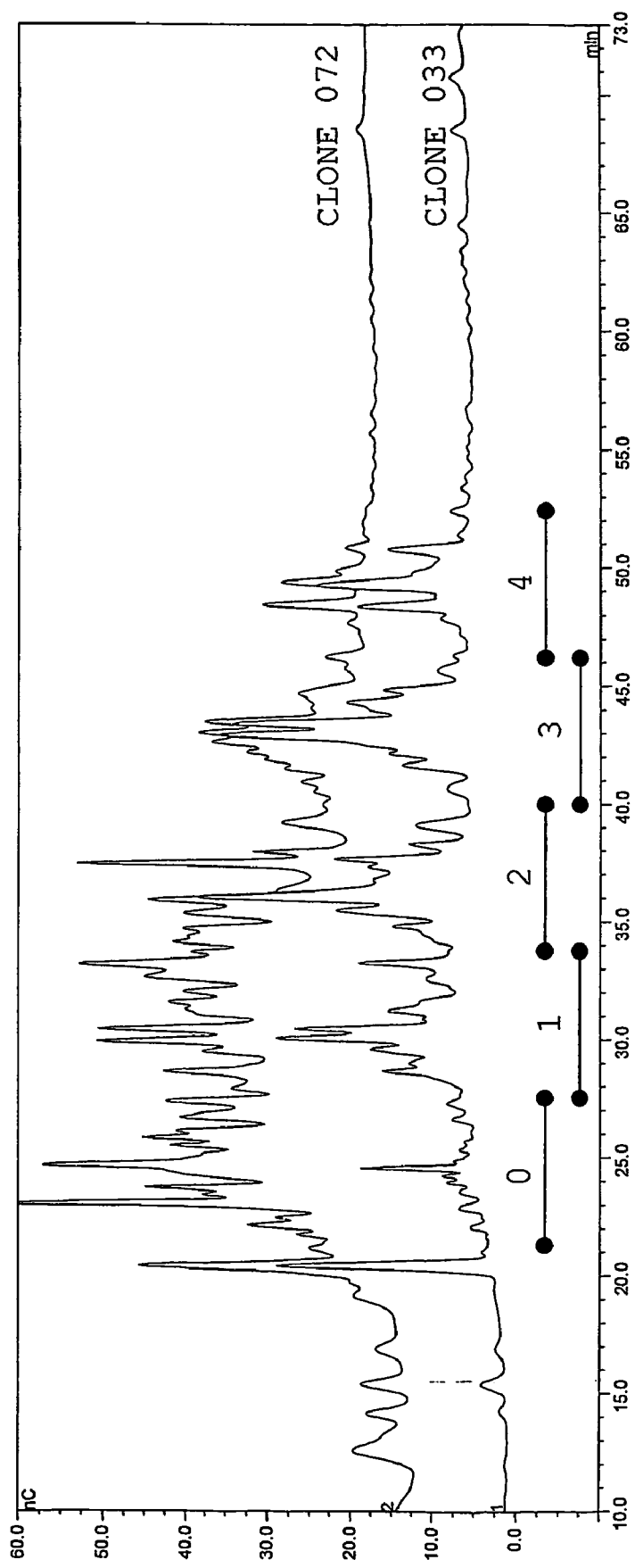

FIG. 12. HPAEC-PAD profile of N-glycans released from EPO produced by the HT1080/EPO clone 033 and the HT1080/E1A.E1B clone 072. Lines at the bottom indicate the elution of uncharged (0), monocharged, double charged, triple charged and tetra charged (1-4, resp.) glycans. Note the shift to less loaded N-linked glycans of clone 072.

FIG. 13. Maldi-MS analyses of EPO produced by 3 different clones (A). The HT1080/EPO clone 033, the HT1080/E1A-EPO clone 008 and the HT1080/E1A.E1B-EPO clone 072. The latter 2 clones show a more complex profile.

Figure 14:
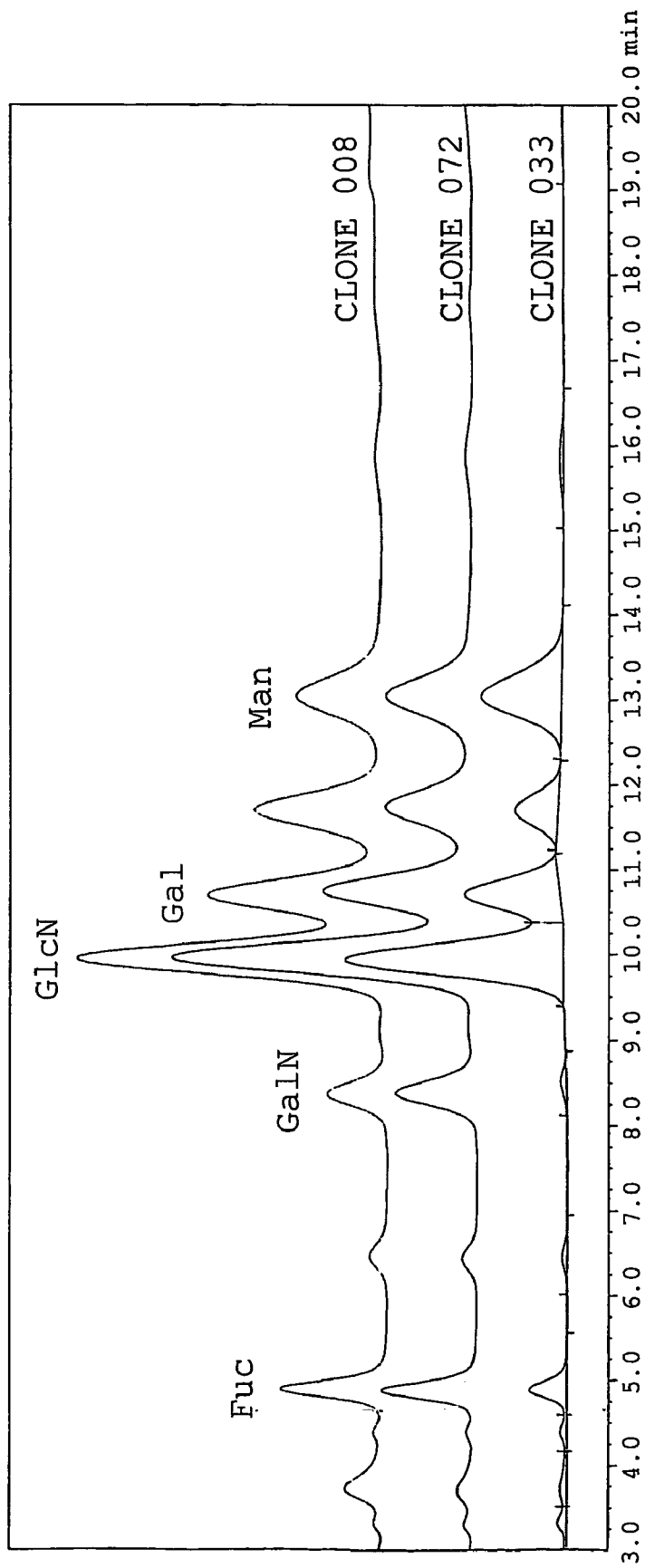
Figure 15A:
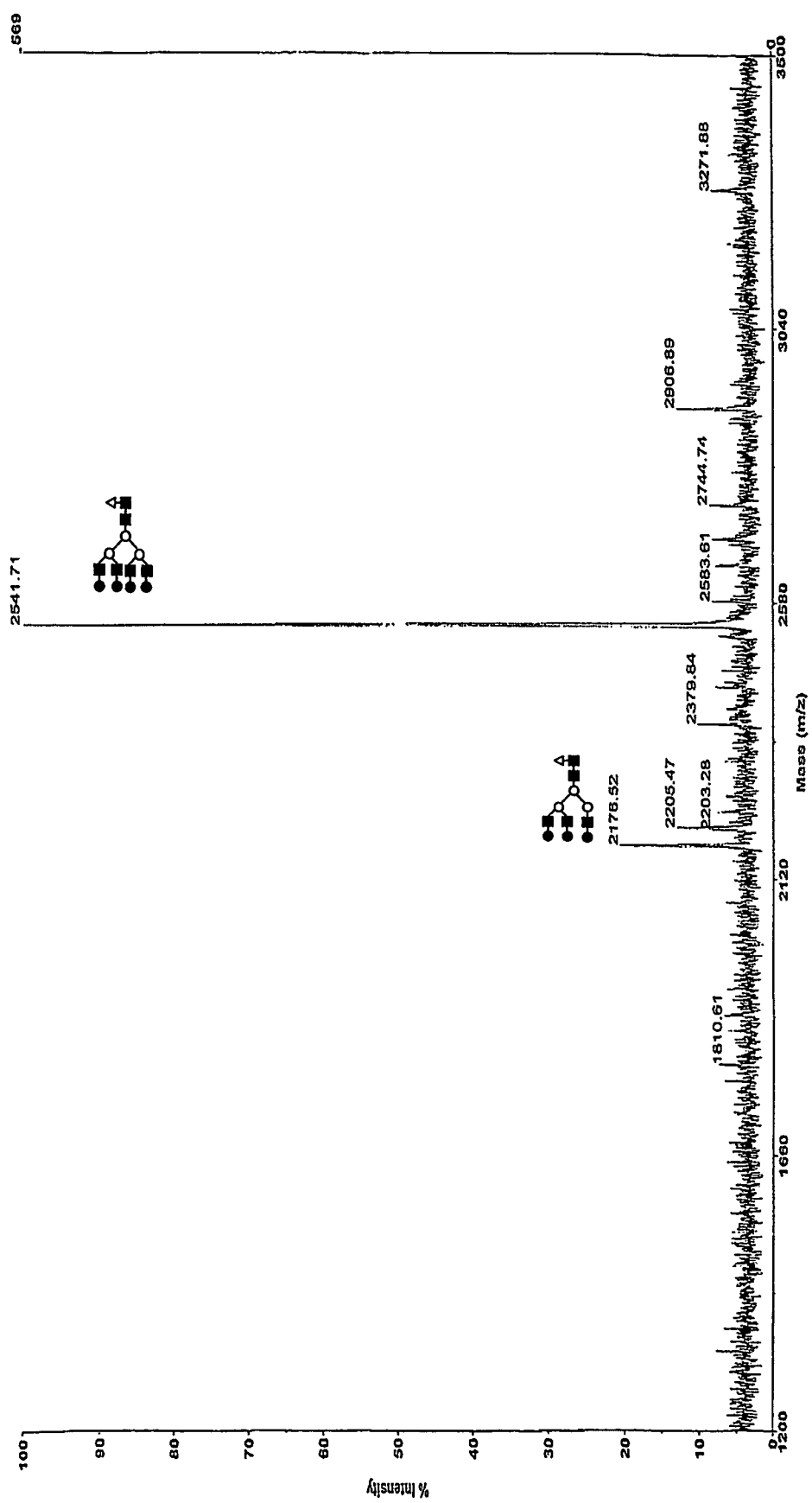
Figure 15B:
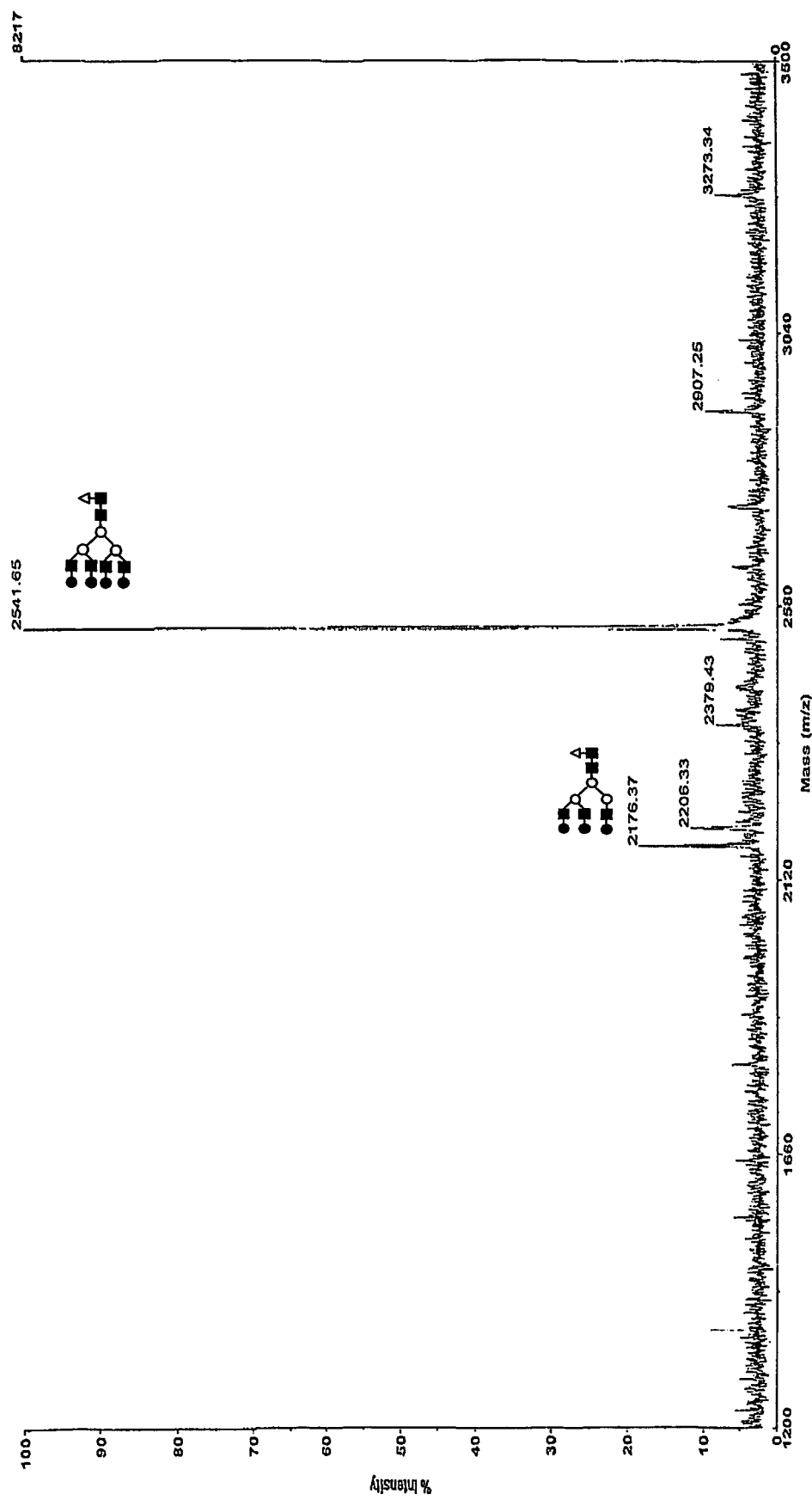
Figure 15C:
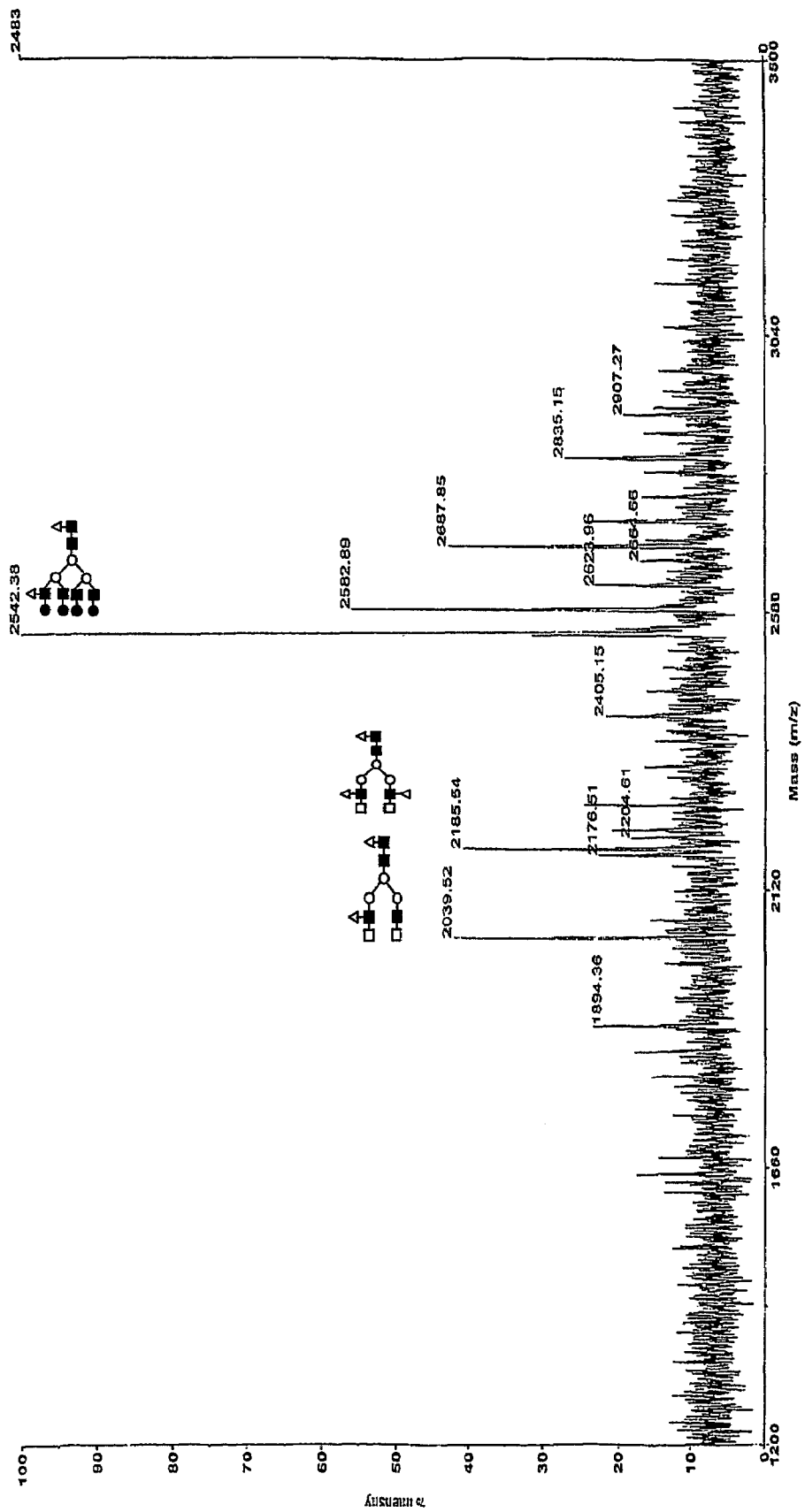
Figure 15D:
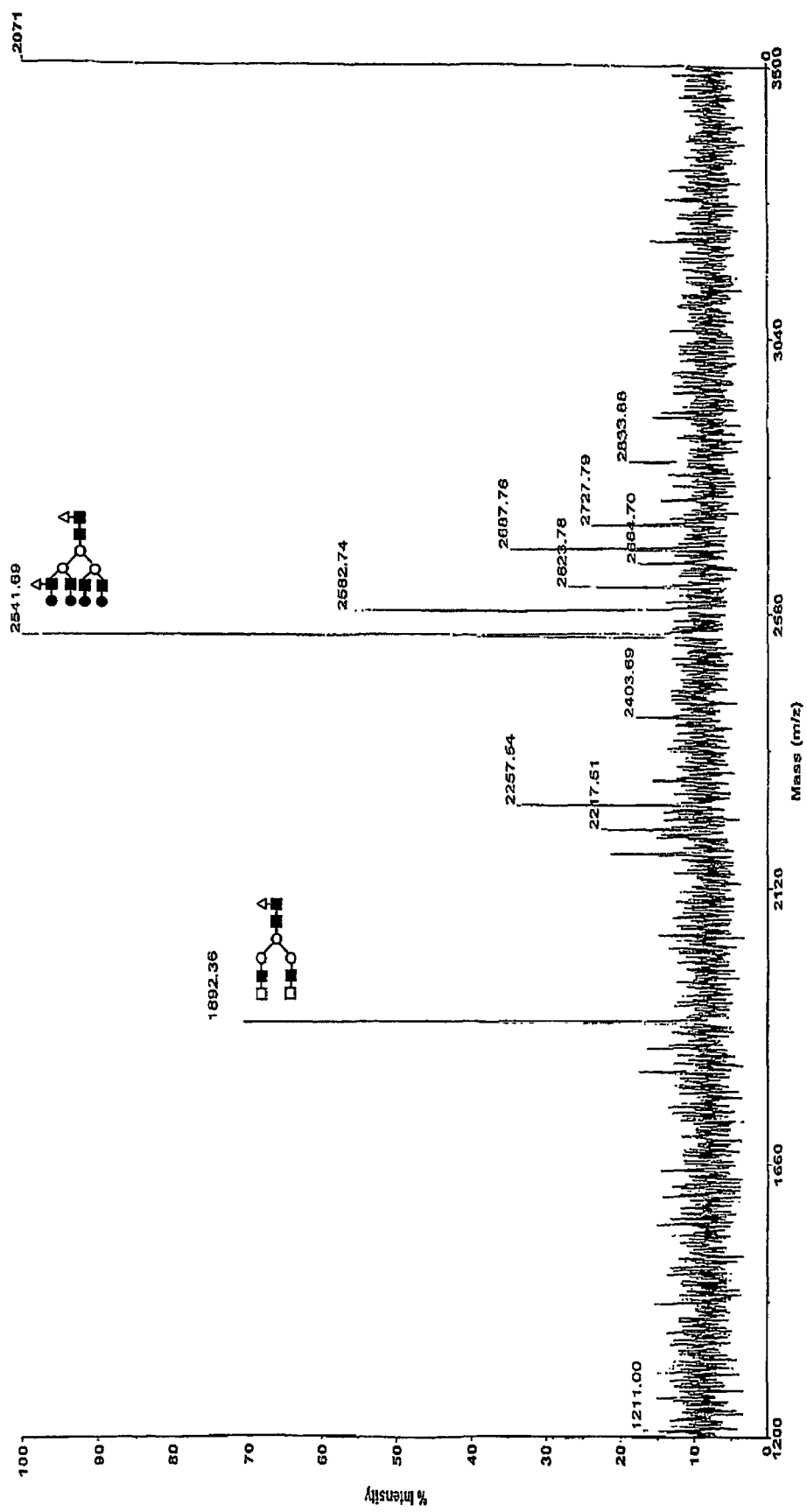

FIG. 14. Profiles obtained from monosaccharide analysis of the N-linked glycans of HT1080/EPO clone 033, HT1080/E1A-EPO clone 008 and HT1080/E1A.E1B-EPO clone 072. The ratio of the indicated monosaccharides (Fuc=Fucose, GalN=N-acetyl-galactosamine, GlcNac=N-acetyl-glucosamine, Gal=Galactose, Man=Mannose) was normalized to mannose.

FIG. 15. Maldi-MS analyses of EPO produced by the HT1080/EPO clone 033 (A,B) and the HT1080/E1A.E1B-EPO clone 072 (C,D) treated with (B,D) or without (A,C) α-fucosidase. Only differences were observed in the glycan profiles of EPO derived from clone 072. A clear change of peaks with m/z values of ~2039, ~2185 and ~1892 is found (C and D), which most likely represent the decrease of proposed structures containing antennary deoxyhexoses.

Figure 16:
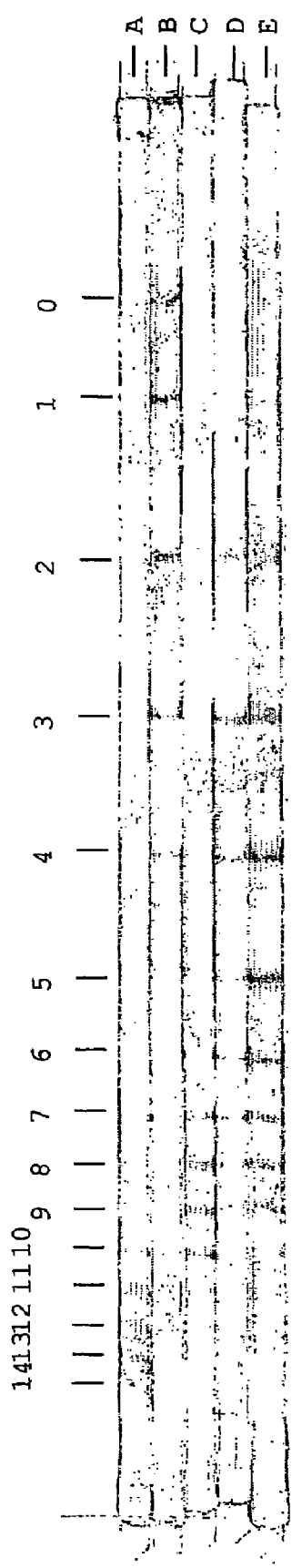

FIG. 16. Various isoforms of the different EPO preparations separated by IEF. EPO-isoforms contain 0-14 sialic acids per molecule. The following samples were applied (2000 eU per strip): Eprex (A); neuraminodase-treated Eprex (B); CHO-EPO, total production (C); PER.C6™ EPO, clone 022 (D); frCHO-EPO (E)

Figure 17:
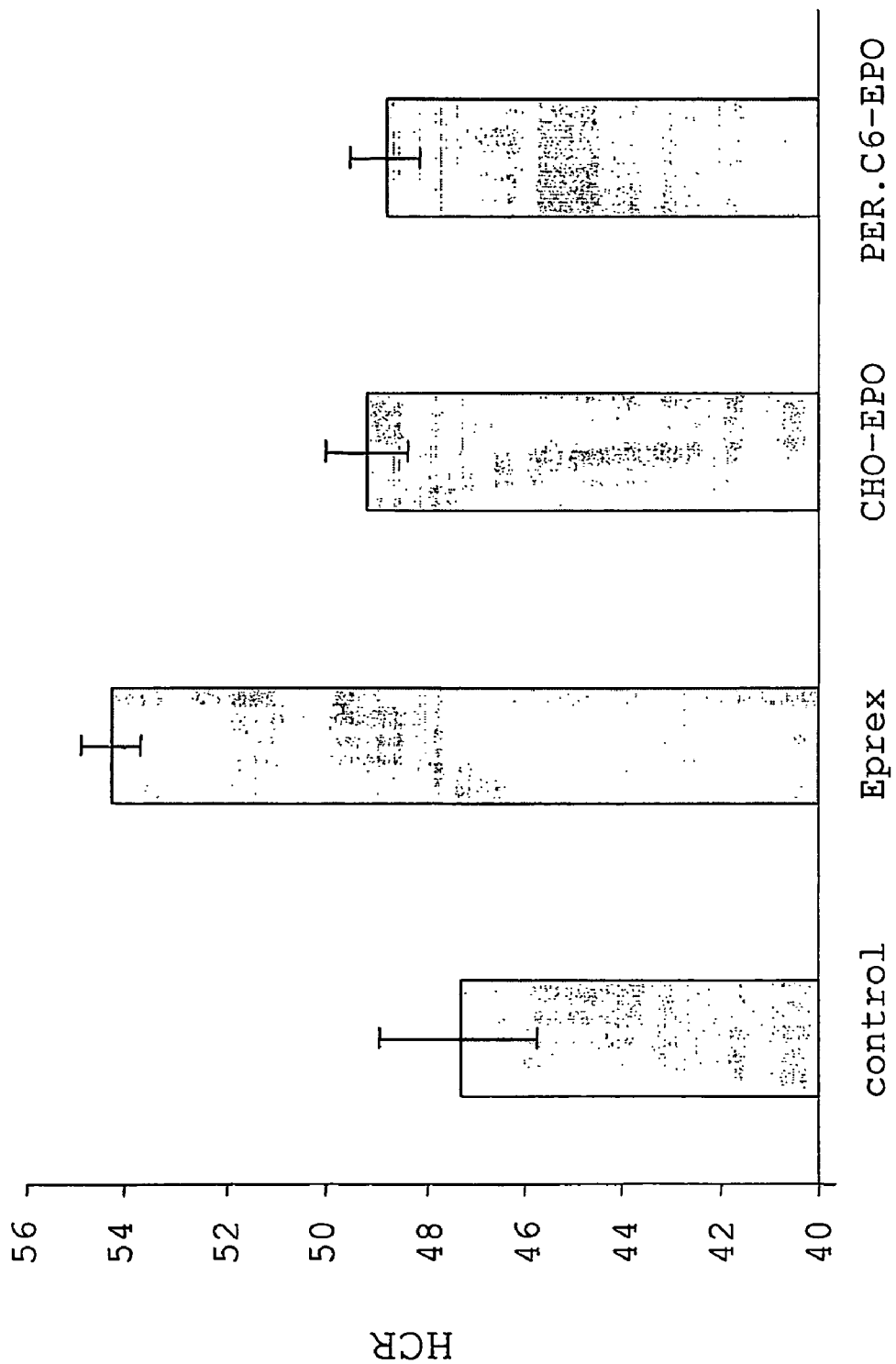

FIG. 17. Heamatocrit (HCR, volume percentage) of rats injected with 5000 eU/kg Eprex, frCHO-EPO, PER.C6™-EPO, or with diluent buffer (control). The EPO treated rats revealed a significant higher HCR vs. control, frCHO-EPO and PER.C6™-EPO ($p<0.001$).

Figure 18:
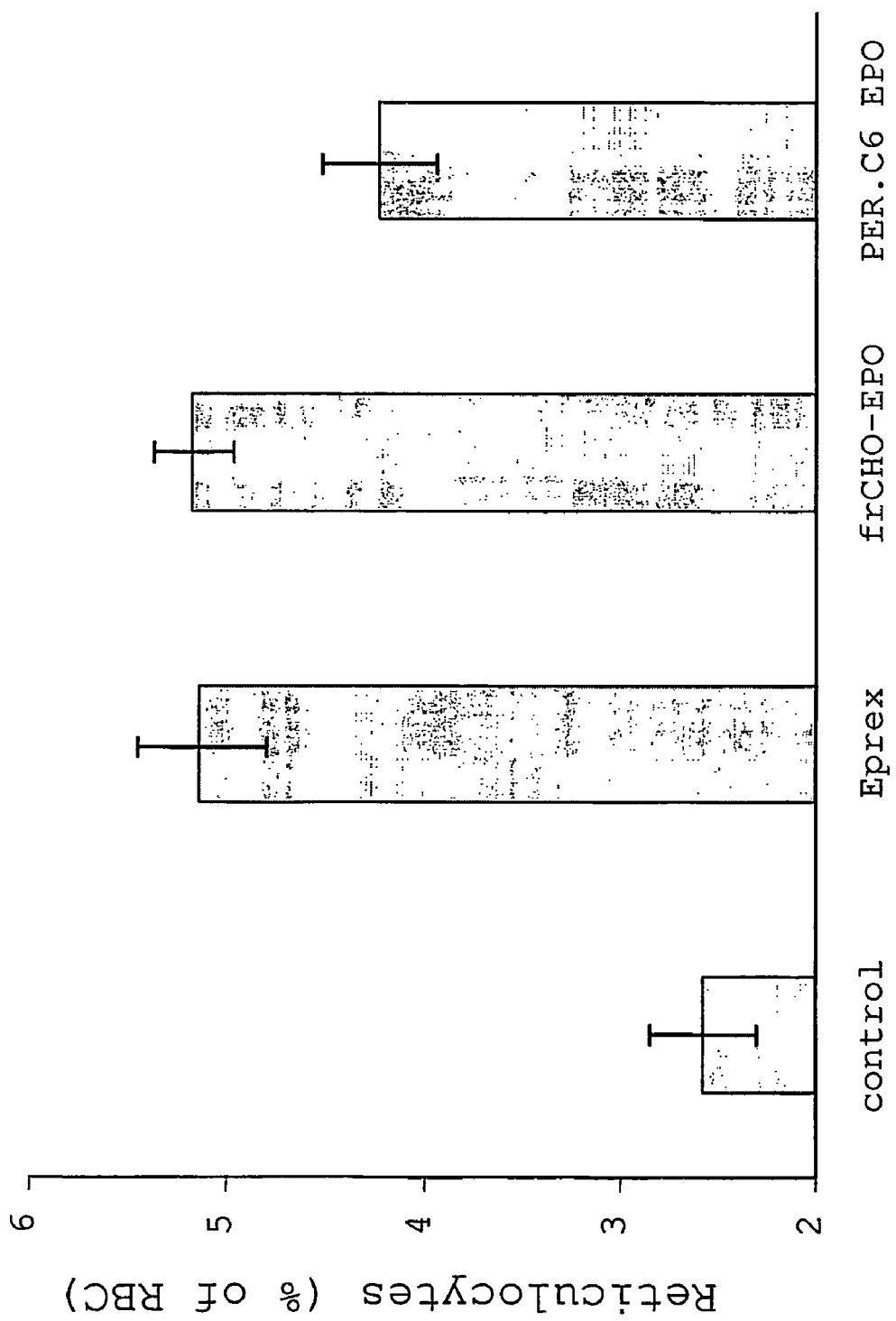

FIG. 18. Percentage reticulocytes in blood of rats injected with 5000 eU/kg Eprex, frCHO-EPO, PER.C6™-EPO, or with diluent buffer (control). The EPO treated rats revealed a significant higher percentage reticulocytes vs. control ($p<0.001$). The percentage reticulocytes of both Eprex and frCHO-EPO treated rats was significantly higher compared to PER.C6™-EPO ($p<0.001$).

Figure 19:
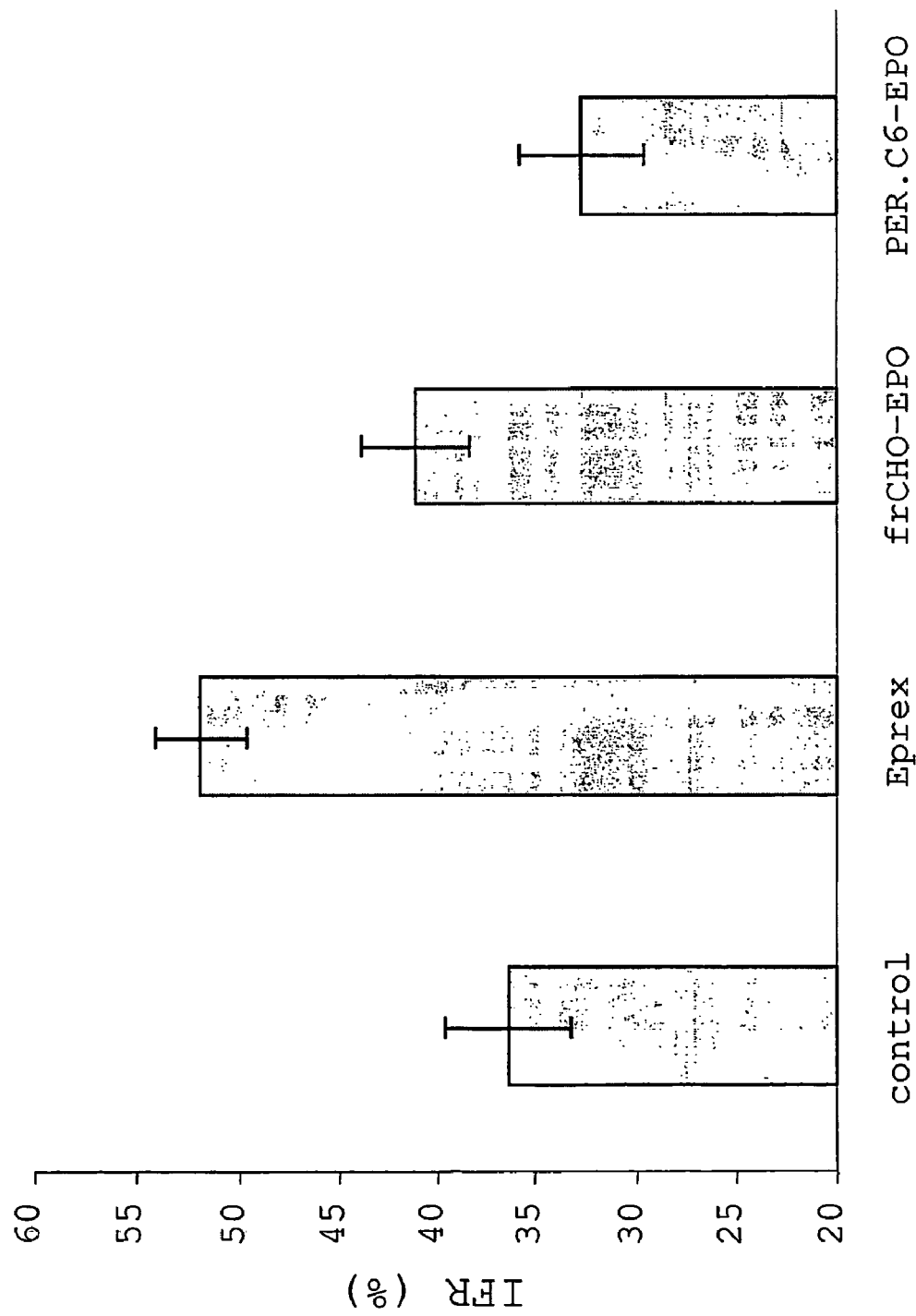

FIG. 19. Percentage immature reticulocytes (IFR) of the total reticulocyte population four days after injection with 5000 eU/kg Eprex, frCHO-EPO, PER.C6™-EPO, or with diluent buffer (control). The Eprex treated rats revealed a significant higher % immature reticulocytes vs. control, frCHO-EPO or PERC6-EPO ($p<0.001$).

Figure 20:
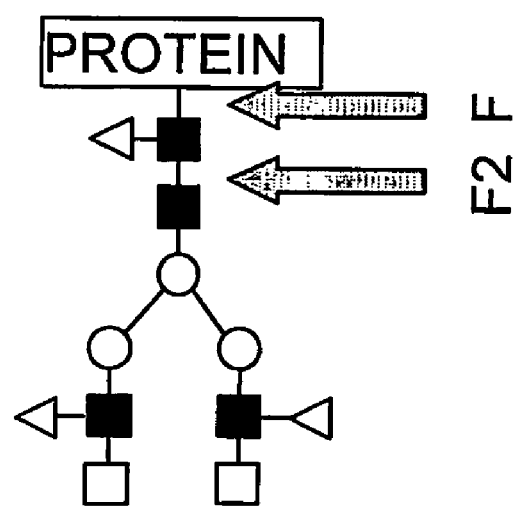

FIG. 20. Cleavage site of PNGase F (marked with F) and endoglycosidase F2 (marked with F2).

Figure 21:
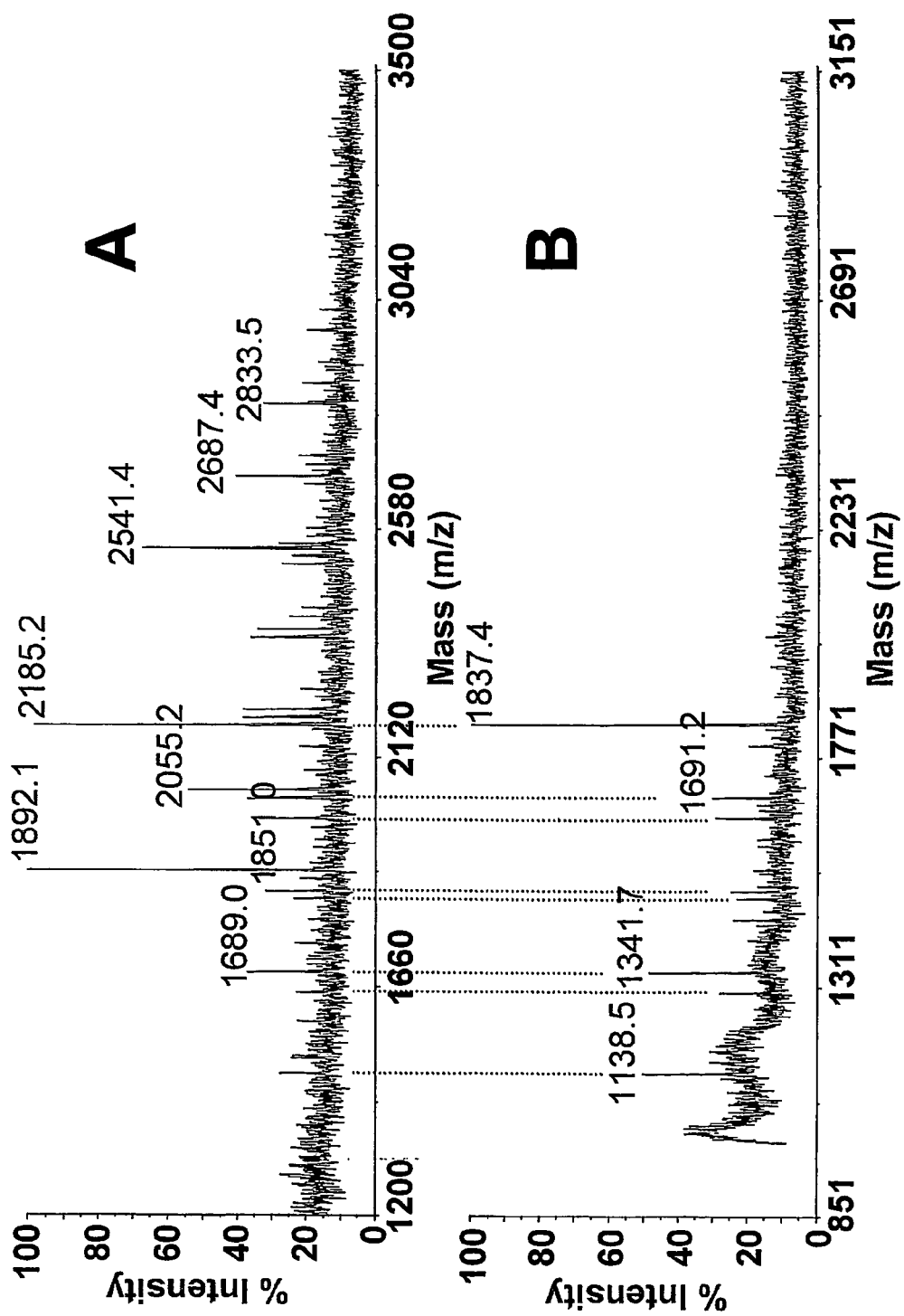

FIG. 21. MALDI spectrum of PER.C6™-EPO glycans released with PNGase F (A) and with endoglycosidase F2 (B). The x-axis of the lower spectrum is aligned in such a way that the corresponding peaks in both spectra are directly above each other (349 Da difference, see text).

Figure 22:
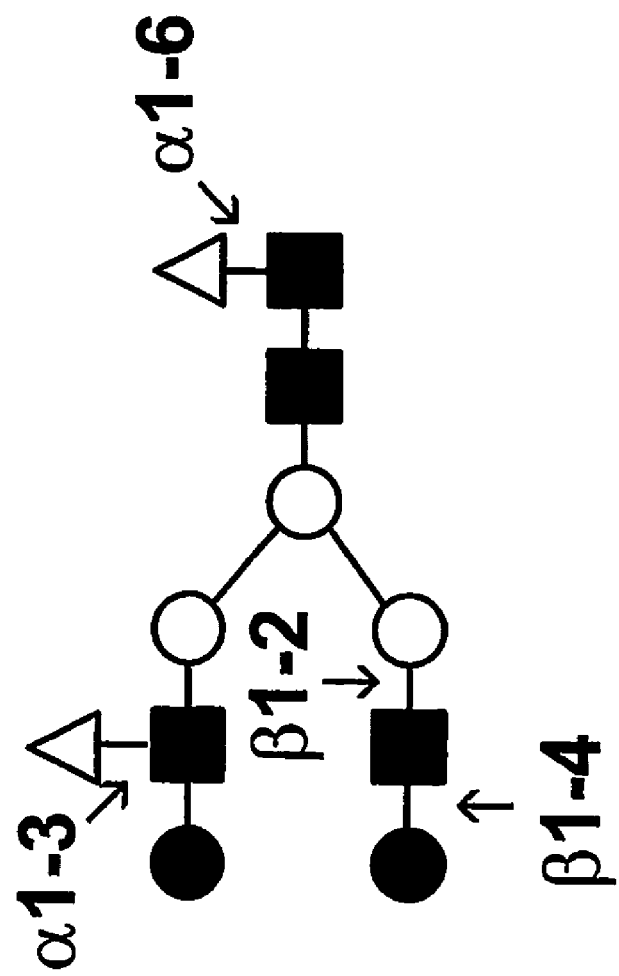

FIG. 22. Some monosaccharide linkages of N-terminal glycans.

Figure 23:
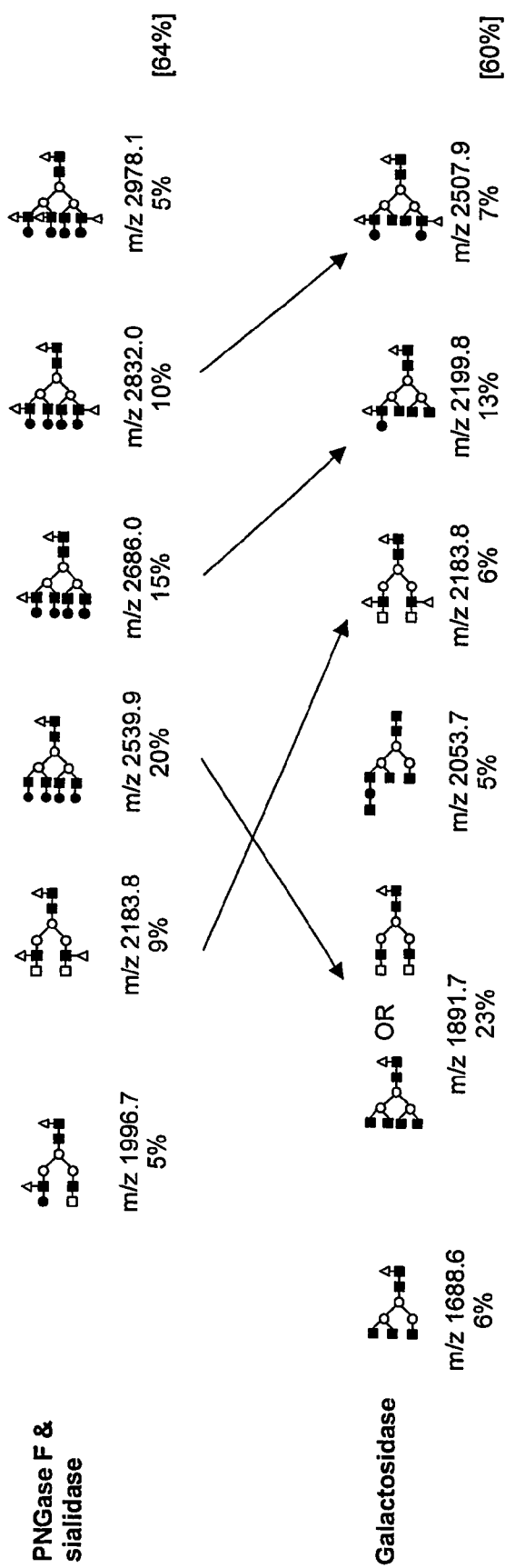

FIG. 23. The upper part of the scheme gives the desialylated glycans released from PER.C6™-EPO; the values in the lower part are detected in the spectrum after galactosidase treatment. Between brackets the total percentage of the spectrum reflected in the given structures. Spectra in FIG. 26.

Figure 24:
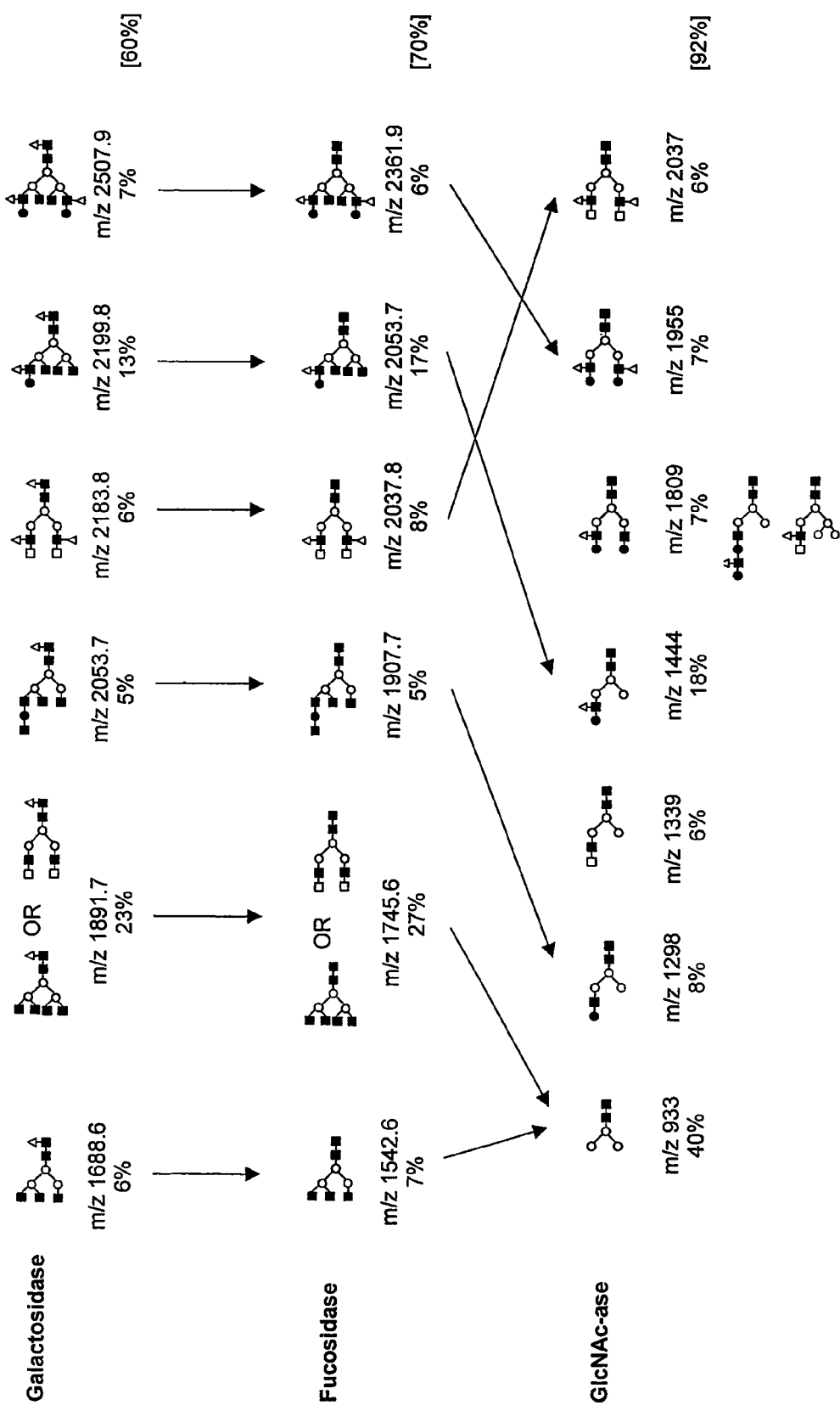

FIG. 24. The upper part of the scheme gives the desialylated glycans released from PER.C6™-EPO which were incubated with galactosidase; the values in the middle part are detected in the spectrum after bovine kidney fucosidase treatment and the lower values are obtained after GlcNAc-ase incubation. Between brackets the total percentage of the spectrum reflected in the given structures. Spectra in FIG. 26.

Figure 25:
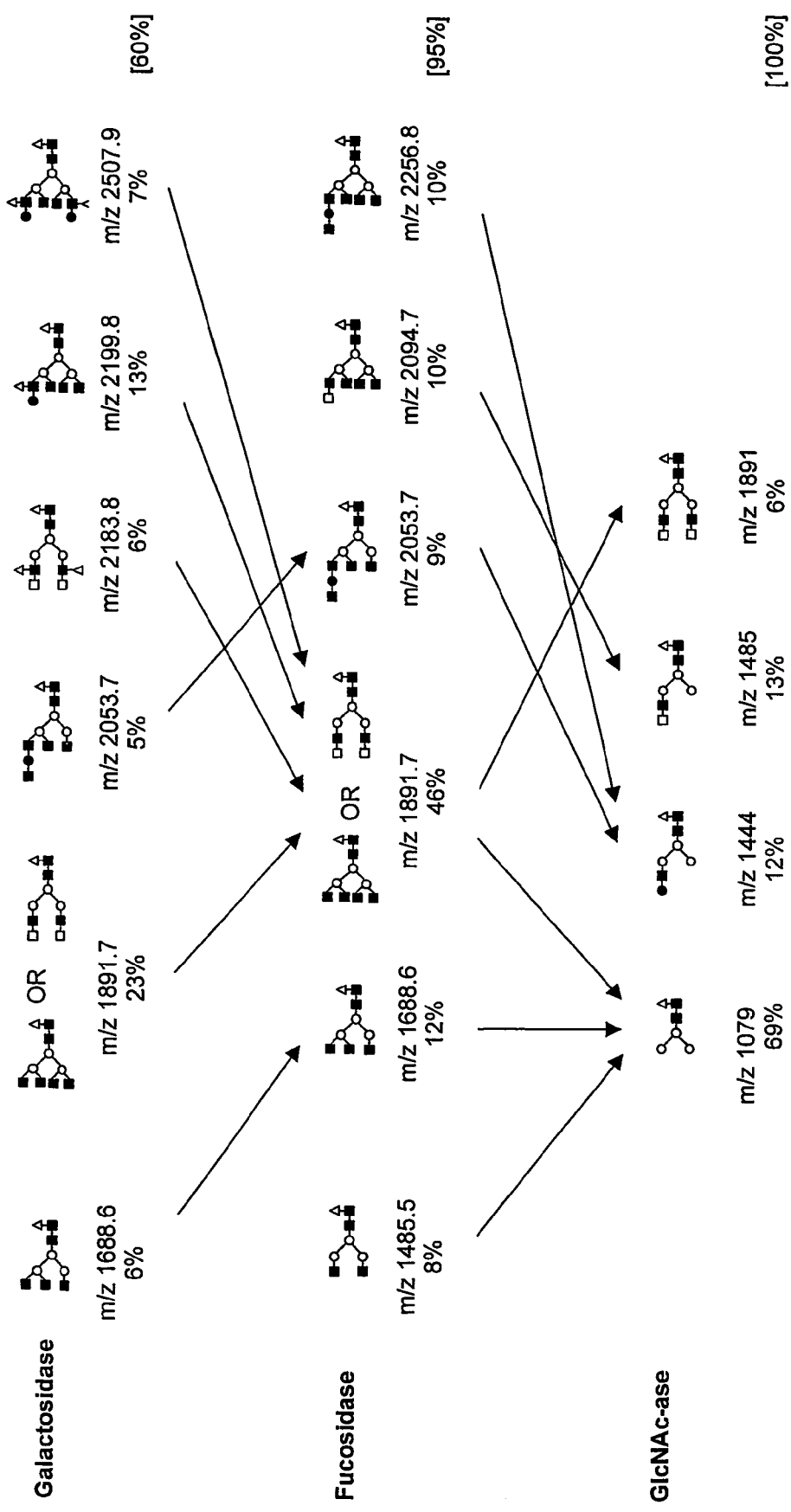

FIG. 25. The upper part of the scheme gives the desialylated glycans released from PER.C6™-EPO which were incubated with galactosidase; the values in the middle part are detected in the spectrum after almond meal fucosidase treatment and the lower values are obtained after GlcNAc-ase incubation. Between brackets the total percentage of the spectrum reflected in the given structures. Spectra in FIG. 27.

FIG. 26. MALDI spectra of exoglycosidase treatments of the N-linked glycans of PER.C6™-EPO.
A.) PER.C6™-EPO incubated with PNGase F and neuraminidase.
B.) PER.C6™-EPO incubated with PNGase F, neuraminidase and galactosidase.
C.) PER.C6™-EPO incubated with PNGase F and neuraminidase, and subsequently treated with galactosidase and bovine kidney fucosidase.
D.) PER.C6™-EPO incubated with PNGase F and neuraminidase, and subsequently treated with galactosidase, bovine kidney fucosidase and GlcNAc-ase.
E.) PER.C6™-EPO incubated with PNGase F and neuraminidase, and subsequently treated with galactosidase and almond meal fucosidase.
F.) PER.C6™-EPO incubated with PNGase F and neuraminidase, and subsequently treated with galactosidase, almond meal fucosidase and GlcNAc-ase.

SUMMARY OF THE INVENTION

The present invention provides methods for identifying, selecting and obtaining mammalian cells that are capable of producing proteinaceous molecules, such as peptides and proteins comprising post-translational modifications, wherein said post-translational modifications are predetermined and brought about by the mammalian cell in which the proteinaceous molecule is expressed. The invention further provides methods for obtaining and producing proteinaceous molecules, such as erythropoietin (EPO), using mammalian cells obtainable according to methods of the present invention and on mammalian cells that have been obtained on the basis of their ability to produce proteins and/or post-translational modifications that are indicative for the predetermined post-translational modification that is desired.

The present invention provides a method for producing a proteinaceous molecule comprising a predetermined post-translational modification, comprising the steps of: providing a mammalian cell obtainable by methods according to the invention, with a nucleic acid encoding said proteinaceous molecule in such a way that said mammalian cell harbors said nucleic acid in an expressible form; and culturing said mammalian cell under conditions conducive to the production of said proteinaceous molecule.

In one embodiment of the invention, the invention provides a method for producing a proteinaceous molecule comprising a predetermined post-translational modification, comprising the steps of: identifying a mammalian cell having the ability to provide the proteinaceous molecule with said predetermined post-translational modification; providing said mammalian cell with a nucleic acid encoding said proteinaceous molecule in such a way that said mammalian cell harbors said nucleic acid in an expressible form; and culturing said mammalian cell under conditions conducive to the production of said proteinaceous molecule.

In another embodiment, the invention provides a method for producing a proteinaceous molecule comprising a predetermined post-translational modification, said method comprising the steps of: identifying a mammalian cell having the ability to provide said proteinaceous molecule with said predetermined post-translational modification; providing said mammalian cell with a nucleic acid encoding said proteinaceous molecule in such a way that said mammalian cell harbors said nucleic acid in an expressible form; culturing said mammalian cell under conditions conducive to the production of said proteinaceous molecule; analyzing said post-translational modifications on said proteinaceous molecule so produced; and determining whether said post-translational modification present on said proteinaceous molecule comprises said predetermined post-translational modification.

In one preferred embodiment, the present invention provides mammalian cells that have neural characteristics and properties such that significant amounts of recombinant proteins can be produced that harbor 'neural- or brain-type' properties. The production of recombinant proteins, like brain-type EPO, carrying specific predetermined post-translational modifications, is now feasible by using the methods and means of the present invention.

The invention moreover provides methods for producing a proteinaceous molecule comprising a predetermined post-translational modification, said method comprising the steps of: providing a mammalian cell obtainable by a method according to the present invention, with a nucleic acid encoding said proteinaceous molecule in such a way that said mammalian cell harbors said nucleic acid in an expressible form; culturing said mammalian cell under conditions conducive to the production of said proteinaceous molecule, and purifying said proteinaceous molecule from the mammalian cell culture.

In another embodiment, the present invention provides methods for producing a proteinaceous molecule comprising a predetermined post-translational modification, said method comprising the steps of: providing a mammalian cell obtainable by a method according to the present invention, with a nucleic acid encoding said proteinaceous molecule in such a way that said mammalian cell harbors said nucleic acid in an expressible form; culturing said mammalian cell under conditions conducive to the production of said proteinaceous molecule; analyzing said post-translational modifications on said proteinaceous molecule so produced; and determining whether said post-translational modification present on said proteinaceous molecule comprises said predetermined post-translational modification.

Preferably, said methods for producing proteinaceous molecules comprise the extra step of purifying said proteinaceous molecule from the mammalian cell culture. More preferred are methods for producing a proteinaceous molecule in a mammalian cell of the invention, wherein said mammalian cell is immortalized and/or expresses E1A adenoviral sequences. Immortalization or introduction of E1A adenoviral sequences can take place prior to the identification of the obtained mammalian cell, but might also take place after the cell is identified, selected and/or obtained.

The present invention furthermore provides methods for purifying proteinaceous molecules, wherein said proteinaceous molecules are purified from cell culture on the basis of the predetermined post-translational modification present on the molecule, said predetermined post-translational modification being brought about by the mammalian cell on which the molecule was produced.

The present invention furthermore provides for use of a composition of erythropoietin-like molecules selected from the group consisting of erythropoietin, one or more muteins of erythropoietin, one or more derivatives of erythropoietin, or a collection of one or more fractions of erythropoietin molecules sialylated to a varying degree, for the preparation of a medicament for the treatment of a disorder selected from the group consisting of ischemia, a reperfusion injury, a hypoxia-induced disorder, an inflammatory disease, a neurodegenerative disorder, and acute damage to the central- or peripheral nervous system, wherein said composition of erythropoietin-like molecules has on a protein content basis a lower erythropoietic activity in vivo than erythropoietin-like molecules currently used for treatment of anemia, such as epoetin alfa and epoetin beta. The present invention also provides pharmaceutical compositions comprising such erythropoietin-like molecules. The invention also provides methods for treatment or prevention said disorders, comprising administering said compositions.

In other aspects, the present invention provides a method for producing in a mammalian cell proteinaceous molecules in need of a glycosylation structure selected from the group consisting of a (sialyl)Lewis X and/or LacdiNac containing N-linked glycan structures, characterized in that said cell expresses nucleic acid encoding E1A from an adenovirus, with the proviso that when said proteinaceous molecule is erythropoietin said mammalian cell is not a PER.C6™ cell, when said proteinaceous molecule is glycodelin or protein C or tissue factor pathway inhibitor said mammalian cell is not a HEK293 cell and when said proteinaceous molecule is matrix metalloprotease 1 said mammalian cell is not a HT1080 cell.

It is another aspect of the invention to provide a method for producing a fraction enriched in a proteinaceous molecule having N-linked glycans comprising (sialyl)Lewis X and/or LacdiNac structures, comprising the steps of: a) recombinantly expressing said proteinaceous molecule in a cell that expresses nucleic acid encoding E1A from an adenovirus; and b) fractionating the proteinaceous molecules so produced, thereby obtaining a fraction which is enriched in molecules having said N-linked glycans comprising (sialyl) Lewis X and/or LacdiNac structures. In another aspect the invention provides a method for fractionating a mixture comprising proteinaceous molecules that comprise Lewis X structures, said method employing binding of said molecules to an AAL lectin. In other embodiments, fractions so obtained are provided.

It is another aspect of the present invention to provide compositions comprising erythropoietin-like molecules selected from the group consisting of erythropoietin, one or more muteins of erythropoietin, and one or more derivatives of erythropoietin, characterized in that the average number of of lewis-X structures on N-linked glycans per erythropoietin-like molecule is at least about 2.2. In other embodiments, said average number is at least about 2.6, 2.7, 3.6, 4.1 or 5.7. In another aspect, the compositions or fractions according to the invention are used for the preparation of a medicament.

In another aspect the invention provides for the use of erythropoietin recombinantly producible in a mammalian cell which expresses nucleic acid encoding E1A from an adenovirus, for the preparation of a medicament for the treatment of a disorder selected from the group consisting of ischemia, a reperfusion injury, a hypoxia-induced disorder, an inflammatory disease, a neurodegenerative disorder, and acute damage to the central- or peripheral nervous system. In another embodiment, the invention provides a method for the preventative and/or therapeutic treatment of a disorder selected from the group consisting of ischemia, a reperfusion injury, a hypoxia-induced disorder, an inflammatory disease, a neurodegenerative disorder, and acute damage to the central- or peripheral nervous system, said method comprising the step of administering to a human or animal subject a composition of erythropoietin-like molecules selected from the group consisting of erythropoietin, one or more muteins of erythropoietin, and one or more derivatives of erythropoietin, wherein said composition of erythropoietin-like molecules is characterized in that it is recombinantly producible in a mammalian cell comprising nucleic acid encoding E1A from an adenovirus. In certain preferred embodiments, said cell is a PER.C6™ cell.

DETAILED DESCRIPTION

It is the merit of the present invention to provide recombinant production systems suitable for the production of proteins in need of a predetermined post-translational modification. In a first aspect such recombinant systems can be provided using methods according to the invention for identifying expression systems capable of applying the post-translational modification needed for the protein in question or the intended use of the protein in question. In a second aspect, the invention provides a method of making expression systems having the ability to apply a desired post-translational modification of a protein in need thereof. Further aspects of the invention comprise isolated proteins having predetermined post-translational modifications so produced, methods of use, and pharmaceutical compositions comprising the same. The present invention thus provides a method for identifying a mammalian cell capable of producing a proteinaceous molecule comprising a predetermined post-translational modification, said method comprising the steps of: a) analyzing the post-translational modification on a protein produced by said mammalian cell; and b) determining whether said protein comprises said predetermined post-translational modification.

In another embodiment the invention provides a method for selecting a mammalian cell capable of producing a proteinaceous molecule comprising a predetermined post-translational modification, said method comprising the steps of: a) analyzing the presence or absence of a tissue specific marker or a combination of tissue specific markers in said mammalian cell or on the cell surface of said mammalian cell, which marker or combination of said markers is indicative for the ability of said cell to apply the predetermined post-translational modification on a proteinaceous molecule in need thereof, when produced in said cell using techniques of recombinant DNA and cell culture otherwise well known to those of skill in the art; and b) selecting said mammalian cell on the basis of the presence or absence of said tissue specific markers.

In yet another embodiment, the invention provides a method for obtaining a mammalian cell from a heterogeneous cell population, said mammalian cell being capable of producing a proteinaceous molecule comprising a predetermined post-translational modification, said method comprising the steps of: a) sorting cells on the basis of the post-translational modifications on proteins produced by said cells in said heterogeneous cell population; and b) selecting the cells capable of producing proteins comprising said predetermined post-translational modification. Such sorting may be accomplished using methods known in the art, including but not limited to the sorting of cells using fluorescently labeled antibodies recognizing the predetermined post-translational modification.

In another embodiment, the invention provides a method for identifying a mammalian cell capable of producing a proteinaceous molecule comprising a predetermined post-translational modification, said method comprising the steps of: providing said mammalian cell with a nucleic acid encoding a protein in need of and capable of receiving the post-translational modifications, in such a way that said mammalian cell harbors said nucleic acid in an expressible form; culturing said mammalian cell under conditions conducive to the production of said protein; analyzing the post-translational modification on said protein produced by said mammalian cell; and verifying the presence of said post-translational modification on said protein. According to another embodiment, the invention provides a method for identifying a mammalian cell capable of producing a molecule comprising a predetermined post-proteinaceous translational modification, said method comprising the steps of: providing said mammalian cell with a nucleic acid encoding said proteinaceous molecule capable of comprising post-translational modifications, in such a way that said mammalian cell harbors said nucleic acid in an expressible form; culturing said mammalian cell under conditions conducive to the production of said proteinaceous molecule; analyzing the post-translational modification on said proteinaceous molecule produced by said mammalian cell; and determining whether said post-translational modification present on said proteinaceous molecule comprises said predetermined post-translational modification.

A proteinaceous molecule as used herein refers to, but is not limited to, molecules such as peptides, polypeptides and proteins, as well as to mutants of peptides, polypeptides and proteins (molecules comprising deletions, point mutations, swaps and/or chemically induced alterations), as long as they are capable of receiving the predetermined post-translational modification, i.e. have the required amino acid residue(s) in the right context amenable to the modification (e.g. they should comprise an Asn-X-Ser/Thr sequence in case the addition of an N-linked glycan structure is desired, which can be applied to the Asn residue in this context). It also refers to peptides, polypeptides and proteins carrying tags and/or other proteinaceous and non-proteinaceous labels (e.g., radio-active compounds). An example of such a protein is human EPO, which has besides the renal- or serum-type form, other phenotypes such as a brain-type form. Other, non-limiting examples of classes of proteins that have certain characteristics that possibly play an important role in the functionality of the protein in certain tissues and that should (when recombinantly expressed) harbor the predetermined post-translational modifications for a proper function include monoclonal antibodies, neurotrophins, cytokines, insulin-like growth factors, TGF-β like growth factors, fibroblast growth factors, epidermal growth factors, heparin binding growth factors, tyrosine kinase receptor ligands and other trophic factors. Most of these factors are associated with disease syndromes, and therefore most of the proteins might be used in recombinant form in the treatment of humans, provided that the proteins harbor the post-translational modifications necessary to be active in vivo. These proteins should therefore be produced on expression systems that are capable of providing the desired post-translational modifications. Examples of such proteins are, but are not limited to, transferrin, glycodelin, Nerve Growth Factor (NGF), Brain-derived neurotrophic factor, Neurotrophin-3, -4/5 and -6, Ciliary neurotrophic factor, Leukemia inhibitory factor, Cardiotrophin-1, Oncostatin-M, several Interleukins, GM-CSF, G-CSF, IGF-1 and -2, TGF-β, Glial-derived neurotrophic factor, Neurturin, Persephin, Myostatin, Fibroblast Growth Factor-1, -2 and -5, Amphiregulin, Acetylcholine receptor inducing activity, Netrin-1 and -2, Neuregulin-2 and -3, Pleiotrophin, Midkine, Stem Cell Factor (SCF), Agrin, CSF-1, PDGF and Saposin C. Monoclonal antibodies as used herein refer to human and humanized antibodies, to parts thereof, and to equivalents such as single chain Fv (scFv) fragments, Fab fragments, CDR regions, variable regions, light chains and heavy chains, or any other format suitable for use as a specific ligand.

According to one specific embodiment production systems are provided that are capable of applying lewis X structures and/or LacdiNAc on proteins capable of receiving N-linked glycan structures. In accordance with the invention such expression systems can be identified, selected or specifically designed. An example of such purposive design is the introduction into a mammalian cell of nucleic acid comprising an E1A sequence of an adenovirus such that said E1A sequence is expressed in said mammalian cell. Examples of such cells already in existence are HEK293, PER.C6™, 911. Although these cell lines are known per se and have been used for protein production (Van den Nieuwenhof et al, 2000; WO 00/63403; Grinnell et al, 1994), the decisive effect of E1A on the ability to apply lewis X and/or LacdiNAc structures to proteins produced thereon has hitherto not been appreciated.

A post-translational modification as used herein refers to any modification that is present on or in said proteinaceous molecule. It refers to modifications that are introduced during or subsequent to the translation of said molecule from RNA in vivo or in vitro. Such modifications include, but are not limited to, glycosylation, folding, phosphorylation, γ-carboxylation, γ-hydroxylation, multimerization, sulphide bridging and for instance processing events such as the clipping-off or the addition of one or more amino acids. A predetermined post-translational modification as used herein refers to any post-translational modification that is useful for the selected treatment. According to a preferred embodiment, predetermined post-translational modification refers to a form of modification that makes the modified protein particularly useful to treat disorders of specific tissues, organs, compartments and/or cells of a human or animal body. The proteinaceous molecule carrying such predetermined post-translational modifications could as a result be devoid of significant effect (such as detrimental- or other undesired side-effects) other than on the tissue, organ, compartment and/or cell that is to be treated. According to one embodiment, the predetermined post-translational modification causes the protein comprising the predetermined post-translational modification to be cleared from the blood more rapidly, e.g., to reduce adverse side effects. The predetermined post-translational modification can be fully understood in detail in advance, but can also be generally referred to as being a desired state that is required for a proper and wanted activity of the proteinaceous molecule comprising such predetermined post-translational modification, meaning that the detailed modifications present on the proteinaceous molecule of interest do not necessarily have to be fully understood and/or defined, as long as the desired activity is there. Examples of desired glycosylation modifications in O- and/or N-glycans, depending on the intended use, are structures such as Lewis x, sialyl Lewis x, GalNac, GlcNac, LacdiNAc, α1,3-linked fucose attached to N-acetyl-glucosamine, terminal N-acetyl-glucosamine, terminal galactose, bisecting N-acetyl-glucosamine, sulphate group and sialic acid.

The mammalian cells of the present invention are preferably human or of human origin, for the production of human proteins to produce proteins that most likely carry mammalian-, and preferably human, characteristics. To produce proteinaceous molecules that should have neural post-translational modifications, it is preferred to use cells that have neural characteristics, such as protein markers that are indicative for neural cells. This does not exclude that a non-neural cell might be extremely useful in producing proteins comprising neural-type post-translational modifications. It depends on the protein activity that is required, to select, identify or obtain a cell that is capable of producing such post-translational modifications.

Since it is required to produce large quantities of proteins when these will be applied in therapeutic settings, it is preferred that the mammalian cells of the invention are immortalized. Immortalization can be brought about in many ways. Examples of methods to obtain immortalized cells are actively transforming a resting cell into a dividing cell by the addition of nucleic acids encoding transforming and/or immortalizing proteins, or through chemical treatment through which endogenous proteins might become transforming, or by taking cells from tumor material. One preferred method to immortalize non-tumorous cells is by the addition of the E1 region of adenovirus as was shown for cell lines such as 911 and PER.C6™. Other methods of immortalizing cells are known, such as transformation using certain Human Papillomavirus (HPV) protein encoding sequences (e.g. HeLa cells). The addition of certain viral proteins, such as E1 from adenovirus might be beneficial for the production of recombinant proteins, since many of such proteins have transcription-activating features, as well as anti-apoptotic effects. It has now surprisingly been found that expression of E1A of adenovirus in the host cell used as expression system according to the invention, changes the characteristics of the expression system such that it aquires the ability to apply N-linked glycosylation structures that comprise lewis X and/or LacdiNAc.

A suitable cell line for the methods for producing proteinaceous molecules in need of lewis X and/or LacdiNAc-containing N-linked glycans is PER.C6™, deposited under No. 96022940 at the European Collection of Animal Cell Cultures at the Center for Applied Microbiology and Research. Other suitable cell lines according to this aspect include HEK293, 911 and other mammalian cells that may be modified by introduction into one or more of said cells or ancestors thereof, of nucleic acid that contains E1A sequences of an adenovirus in expressible format. Optionally, E1B sequences in expressible format are included, which can be advantageous because of the anti-apoptotic effects exerted by E1B, to counteract the potential apoptotic effects of E1A expression.

The methods for producing proteinaceous molecules according to the invention further may comprise the extra step of purifying said proteinaceous molecule from the mammalian cell culture. Purification as used herein might be performed by using conventional methods that have been described in the art, however, it is preferred to use purification methods that comprise a step in which the post-translational modifications present in and/or on said proteinaceous molecules are employed. Even more preferred are purification methods that comprise a step in which the predetermined post-translational modifications present in and/or on said proteinaceous molecules are employed. When affinity purification methods are applied, it is preferred to use antibodies or other binders, such as lectins specific for particular carbohydrate moieties and that are directed against certain types of post-translational modifications. Examples of such antibodies are antibodies directed against (sialyl) Lewis x structures, lacdiNac structures or GalNac Lewis x structures. Non-limiting examples of lectins useful according to this aspect of the invention are AAL and selectins, such as E-selectin, P-selectin, L-selectin. Using such binders enables one to purify the (recombinant) proteins such that a high percentage of the purified protein carries the desired predetermined post-translational modification. Even more preferred are methods in which the proteinaceous molecule is purified to homogeneity. Examples of methods for purification of proteins from mammalian cell culture are provided by the present invention and encompass for instance affinity chromatography methods for the purification of brain-type glycosylated EPO by using antibodies or lectins recognizing Lewis x structures present in the N-glycans of the recombinantly produced product.

The present invention provides a pharmaceutically acceptable composition comprising a proteinaceous molecule having a predetermined post-translational modification, obtainable according to methods of the present invention, and a pharmaceutically acceptable carrier. Pharmaceutically acceptable carriers are known to those having ordinary skill in the art. In a preferred embodiment said proteinaceous molecule in said pharmaceutically acceptable composition is erythropoietin. According to the invention, erythropoietin produced in cells with neural protein markers acquires a post-translational modification that is active in neural tissue or on neural cells. However, the post-translational modifications are not comparable to the post-translational modifications seen on EPO that circulates in the blood. The erythropoietic effects of the EPO produced on cells with the neural protein markers is significantly lower. In accordance with the present invention it is now strongly suggested that this is due to the absence of a high percentage of sialic acids, and/or to the presence of brain-type features such as Lewis x structures and terminal galactosides. This is advantageous, since such a brain-type EPO can be used in relatively high dosages in the treatment of disorders related to neural tissue or in the treatment of tissue damaged by ischemia (such as an ischemic heart), while at the same time having a significantly reduced effect on erythropoiesis as compared to the EPO preparations currently available. The invention provides recombinant erythropoietin comprising at least one post-translational modification selected from the group consisting of: a sialyl Lewis x structure, a Lewis x structure, a α1,3-linked fucose attached to N-acetyl-glucosamine, a LacdiNAc structure, a terminal N-acetyl-glucosamine group and a terminal galactose group. Said recombinant erythropoietin is producible on a mammalian cell obtainable according to the present invention, as well as on mammalian cells previously known, but not previously appreciated to be suitable for this purpose. One example is PER.C6™ cells. The present invention in accordance with one embodiment further provides the use of PER.C6™ cells for the production of a proteinaceous molecule comprising a predetermined post-translational modification, wherein it is preferred that said proteinaceous molecule is rapidly cleared from the blood and/or used in high dosage. In the case of EPO, producible on PER.C6™, a high dosage may be used to treat or prevent acute damage associated with hypoxia, while limiting the adverse side effects of erythropoiesis.

In one embodiment of the present invention, the proteinaceous molecules of the present invention are suitable for the treatment of a human or a human body by surgery, therapy or diagnosis. Preferably EPO-like molecules according to the invention are used for the manufacture of a medicament for the treatment of hypoxia-induced disorders, neurodegenerative afflictions, or acute damage to the central- or peripheral nervous system. In another preferred embodiment, said proteinaceous molecules such as EPO are used for the manufacture of a medicament for the treatment of ischemia and/or reperfusion injuries. In yet another preferred embodiment, said proteinaceous molecules such as EPO are used for the manufacture of a medicament for the treatment of immune disorder and/or inflammatory disease.

Methods and compositions are disclosed herein for the production and manufacturing of recombinant proteins. The invention is particularly useful for the production of proteins that require co-translational and/or post-translational modifications such as glycosylation and proper folding and relates furthermore to the use of human cells capable of producing brain-type co- and/or post-translational modifications on proteinaceous molecules. These cells can for instance be used for the production of human glycoproteins with neural features that might be therapeutically beneficial, due to their neural features.

The present invention also provides the use of a human cell line with neural characteristics that modifies recombinantly expressed proteins with neural properties such as 'brain-type' or 'neural-type' post-translational modifications such as glycosylation, phosphorylation or folding. An example of such a cell line, named PER.C6™ (U.S. Pat. No. 6,033,908), was generated by the immortalization of human embryonic retina cells using a construct harboring Adenovirus E1 genes. Previously, PER.C6™ cells have proven to be particularly suitable for the production of recombinant human proteins, since high yields of proteins such as the human EPO and fully human monoclonal antibodies can be obtained (described in WO 00/63403). The present invention discloses that recombinant proteins produced by PER.C6™ cells can acquire certain tissue specific features such as neural characteristics (e.g., post-translational modifications such as glycosylation). This is exemplified by the production of a protein that harbors so-called brain-type oligosaccharides. It is shown that human EPO produced by PER.C6™ cells is modified with N-linked sugars that significantly differ from the N-linked sugars found in human urinary EPO or in recombinant human EPO produced by Chinese Hamster Ovary (CHO) cells or Baby Hamster Kidney (BHK) cells. Human urinary EPO and recombinant human EPO produced in CHO and BHK cells contain glycosylation structures that can be referred to as 'renal-type' or 'serum-type' oligo-saccharides. Typically, the N-linked sugars of these CHO- and BHK-EPO preparations are highly branched, highly galactosylated, and highly sialylated, whereas they lack peripheral α1,3-linked fucose (Tsuda et al. 1988; Takeuchi et al. 1988; Nimtz et al. 1993; Watson et al. 1994; Rahbek-Nielsen et al. 1997).

Herein, the nature of the-oligosaccharides linked to human EPO produced on PER.C6™ has been elucidated and shown to be signifantly different from the oligosaccharides present in human urinary EPO and recombinant human EPO produced in CHO and BHK cells. Firstly, the average sialic acid content of the oligosaccharides of PER.C6™-produced human EPO is significantly lower than the average sialic acid content of human urinary EPO or recombinant human EPO (from CHO and BHK). The very low sialic acid content in PER.C6™-produced human EPO is indicative of the presence of N-linked oligosaccharides that contain terminating galactose and/or N-acetyl-galactosamine and/or N-acetyl-glucosamine. Secondly, N-acetyl-galactosamine is found in significant amounts in the N-linked sugars of PER.C6™-produced human EPO, whereas N-acetyl-galactosamine is not found in the N-linked sugars of human urinary EPO and recombinant human EPO produced by CHO cells. Only trace amounts of N-acetyl-galactosamine have been reported to occur in the N-linked sugars in a few batches of recombinant human EPO produced in BHK cells (Nimtz et al. 1993). Third, the N-linked sugars of human EPO produced in PER.C6™ cells are found to contain a very high amount of fucose. A fraction of the fucoses is α1,3-linked to a peripheral N-acetyl-glucosamine thereby forming a so-called Lewis x structure (FIG. 5). Lewis x structures have never been reported to occur in human urinary EPO or in recombinant human EPO produced in CHO and BHK cells. The (sialyl) Lewis x structures present on EPO according to the invention make that this EPO is suitable for binding to selectins and a further application in cardioprotection is envisaged.

Because the protein-linked oligosaccharides have a great impact on the physicochemical properties of the polypeptide such as tertiary conformation, solubility, viscosity, and charge, PER.C6™-produced human EPO has physicochemical properties that differ significantly from human urinary EPO and recombinant human EPO produced by CHO and BHK cells (Toyoda et al. 2000). Clearly, PER.C6™-produced human EPO is less charged than human urinary EPO and recombinant human EPO produced by CHO and BHK cells due to a lower sialic acid content and it may be more hydrophobic due to the very high fucose content. As a result, the average pI of PER.C6™-produced human EPO is significantly higher than the average pI of human urinary EPO or recombinant human EPO produced by CHO and BHK cells. Because the glycans of EPO, in particular the sialic acids, also have an influence on the binding to the EPO receptor, it is expected that PER.C6™-produced human EPO has a different affinity for the EPO receptor than human urinary EPO and recombinant human EPO produced by CHO and BHK cells. Although production of EPO on PER.C6™ cells has been disclosed previously (WO 00/63403), none of the structural details of the produced EPO were disclosed then. Hence the insights obtained herein now justify the conclusion that production of EPO on PER.C6™ makes it suitable for entirely new applications, especially where erythropoiesis is to be seen as an (undesired) side-effect. Of course, other proteins can benefit from the new insights provided herein. According to one other aspect of the invention, a method is provided for the production of protein in need of lewis X and/or LacdiNAc containing N-glycans, using PER.C6™ or any E1A expressing mammalian cell. Examples of proteins that may benefit from such structures, and hence can suitably be produced on said cells, are erythropoietin, transferrin, a glycodelin such as glycodelin A (PP14), Nerve Growth Factor (NGF), Brain-derived neurotrophic factor, Neurotrophin-3, -4/5 and -6, Ciliary neurotrophic factor, Leukemia inhibitory factor, Cardiotrophin-1, Oncostatin-M, an Interleukin, GM-CSF, G-CSF, IGF-1 and -2, TGF-β, Glial-derived neurotrophic factor, Neurturin, Persephin, Myostatin, Fibroblast Growth Factor-1, -2 and -5, Amphiregulin, Acetylcholine receptor inducing activity, Netrin-1 and -2, Neuregulin-2 and -3, Pleiotrophin, Midkine, Stem Cell Factor (SCF), Agrin, CSF-1, PDGF, Saposin C, soluble complement receptor-1, alpha-1 acid glycoprotein, acute-phase proteins, E-selectin ligand-1, LAM-1, Carcinoembryonic antigen-like CD66 antigens, peripheral lymph node Addressin, CD75, CD76, CD45RO, CD21, P-selectin glycoprotein ligand-1, GlyCAM-1, Mucin-type glycoproteins, CD34, podocalyxin, α1-antichymotrypsin, α1-protease inhibitor, α-amylase, salivary proline-rich glycoproteins, SERP-1, interferon-β, β-trace protein, Protein C, Urokinase, Schistosome glycoprotein, Glycodelin A, tissue factor pathway inhibitor, α-fetoprotein, human pregnancy proteins such as gonadotropic hormones such as Follicle Stimulating Hormone (FSH), Luteinising Hormone (LH), human Choriogonadotropin (hCG), or fragments or variants of any of these that are capable of receiving said glycosylation structures. Fragments as used herein are parts of the protein and can be peptides of several amino acids long up to almost the whole protein. Variants can be muteins, fusion proteins, proteins or peptides coupled to other non-protein moieties, and the like. Such fragments or variants according to the invention should be capable of receiving the post-translational modifications.

In other aspects of the invention, methods are provided for producing a fraction enriched in a proteinaceous molecule having N-linked glycans comprising (sialyl) Lewis X and/or LacdiNac structures, comprising the steps of: a) recombinantly expressing said proteinaceous molecule in a cell that expresses nucleic acid encoding E1A from an adenovirus; and b) fractionating the proteinaceous molecules so produced, thereby obtaining a fraction which is enriched in molecules having said N-linked glycans comprising (sialyl) Lewis X and/or LacdiNac structures. The proteineceous molecules mentioned above can benefit from this aspect of the invention. Protein C produced on HEK293 dells and subsequently purified has been described to have a particular glycosylation structure comprising GalNAc-lewis X structures (Grinnell et al, 1994), but the purified proteins was not purposefully enriched in this type of sugars, and not by deliberately choosing a production cell that expresses E1A. It is the merit of the present invention to teach that mammalian cells expressing adenoviral E1A can be used to produce the proteins with N-linked glycans comprising (sialyl) Lewis X and/or LacdiNAc structures purposefully, and furthermore to enrich for these particular fractions. Preferably, said fractions are enriched by a method comprising an affinity purification step that employs the desired glycan structures, such as using binding to a lectin or a monoclonal antibody that binds to said N-linked glycans comprising (sialyl) Lewis X and/or LacdiNAc structures. It is shown herein that using these methods for EPO production one is able to obtain fractions of EPO with particular glycosylation profiles. It is an aspect of the invention to provide compositions comprising erythropoietin-like molecules selected from the group consisting of erythropoietin, one or more muteins of erythropoietin, and one or more derivatives of erythropoietin, characterized in that the average number of of lewis-X structures on N-linked glycans per erythropoietin-like molecule is at least about 2.2. In other embodiments, said average number of lewis-X structures on N-linked glycans per erythropoietin-like molecule is at least about 2.6, 2.7, 3.6, 4.1, or 5.7. Such compositions can be valuable for medicinal purposes as disclosed herein.

The present invention furthermore discloses the use of brain-type proteins produced in human neural cells for the treatment of ischemia/reperfusion injury in mammals and especially in humans. Ischemia/reperfusion injury as used herein is-defined as the cellular damage that occurs after reperfusion of previously viable ischemic tissues. Ischemia/reperfusion injury is associated with, for example, but not limited to thrombolytic therapy, coronary angioplasty, aortic cross clamping, cardiopulmonary bypass, organ or tissue transplantation, trauma and shock.

The present invention provides the use of therapeutic proteins, produced in mammalian cells, with brain-type oligosaccharides. These brain-type oligosaccharides comprise in particular Lewis x structures, sialyl Lewis x structures, or derivatives thereof containing the (sialyl) Lewis x structure, for the treatment of ischemia/reperfusion injury in mammalian subjects such as humans. The presence of (sialyl) Lewis x structures on recombinant proteins targets these proteins to the injured site of ischemia/reperfusion and thereby exerting their ischemia/reperfusion protective effect more effectively than proteins containing no (sialyl) Lewis x structures. The presence of brain-type oligosaccharides on recombinantly expressed proteins is exemplified in the present invention by Erythropoietin (EPO), which is produced on PER.C6™ cells. This particular type of EPO contains the Lewis x as well as the sialyl Lewis x structures. In the present invention experiments are described that show the superiority of PER.C6™ brain-type (or neural-type) EPO compared to serum-type (or renal-type) EPO with respect to the cardioprotective function in in vivo models of cardiac ischemia/reperfusion injury and to stroke.

Another advantage presented by the present invention is that PER.C6™-produced human EPO has a neurotrophic activity. PER.C6™-produced EPO gives the EPO protein physicochemical and/or pharmacokinetic and/or pharmacodynamic advantages in functioning as a neurotrophic and/or neuro-protecting agent. PER.C6™-produced EPO has higher affinity for neural cells and for the EPO-R on neural cells than the highly sialylated serum-type glycosylated human recombinant EPO produced in CHO and BHK cells. Recombinant human EPO produced on non-neural cells (Goto et al. 1988) has a lower affinity for the EPO-R on neural cells than for the EPO-R on erythroid progenitor cells (Musada et al. 1993 and 1994).

The neuroprotective role of EPO clearly opens new possibilities for the use of recombinant human EPO as neuroprotective therapy in response to toxic chemicals that may be induced by inflammation or by hypoxia and/or ischemia, or in neurodegenerative disorders. Yet, a major drawback is that when applied as a neuroprotective agent, recombinant EPO present in the blood circulation will also give rise to an increase of the red blood cells mass or hematocrit. This, in turn, leads to a higher blood viscosity, which may have detrimental effects in brain ischemia (Wiessner et al. 2001).

The present invention provides a solution for the problem that recombinant human EPO that has been applied thus far as a neuroprotective agent has the undesired haematotropic side effect (Wiessner et al. 2001). Thus, it is shown that PER.C6™-produced brain-type glycosylated recombinant human EPO has a high potential as a neurogenesis and/or a neuroprotective agent whereas it has a low potential in stimulating erythropoiesis.

According to the invention, EPO produced on a mammalian cell that expresses E1A, such as PER.C6™-produced EPO, can be administered systemically (intra-venous, intra-peritoneal, intra-dermal) to inhibit, to prevent and/or to repair the neural damage that is caused by, for example, acute head and brain injury or neuro-degenerative disorders. The present invention also provides products that can be used to modulate the function of tissues that might get heavily damaged by hypoxia, such as the central- and peripheral nervous system, retinal tissue and heart tissue in mammals. Such tissues may be diseased but may also be normal and healthy. Disorders that can be treated by products provided by the present invention may result from acute head-, brain- and/or heart injuries, neuro-degenerative diseases, seizure disorders, neurotoxin poisoning, hypotension, cardiac arrest, radiation, multiple sclerosis and/or from injuries due to hypoxia. Hypoxia may be the result of prenatal- or postnatal oxygen deprivation, suffocation, emphysema, septic shock, cardiac arrest, choking, near drowning, sickle cell crisis, adult respiratory distress syndrome, dysrythmia, nitrogen narcosis, post-surgical cognitive dysfunction, carbon monoxide poisoning, smoke inhalation, chronic obstructive pulmonary disease anaphylactic shock or insulin shock. Seizure injuries include, but are not limited to, epilepsy, chronic seizure disorder or convulsions. In case the pathology is a result from neuro-degenerative diseases the disorder may be due to AIDS dementia, Alzheimer's disease, Parkinson's disease, Creutzfeldt-Jakob disease, stroke, cerebral palsy, spinal cord trauma, brain trauma, age-related loss of cognitive function, amyotrophic lateral sclerosis, alcoholism, retinal ischemia, glaucoma, general neural loss, memory loss or aging. Other examples of diseases that may be treated with products provided by the present invention include autism, depression, anxiety disorders, mood disorders, attention deficit hyperactivity disorder (ADHD) and cognitive dysfunction.

PER.C6™-EPO can passively cross the blood-brain barrier in case of blood-brain barrier dysfunction. In case the blood-brain barrier is intact, PER.C6™-EPO is thought to be actively transported over the blood-brain barrier through the EPO-R. Some studies suggested that EPO in itself is able to cross the blood-brain barrier when high doses of recombinant EPO is administered (WO 00/61164). Another predicted route for recombinant PER.C6™-EPO to cross the blood-brain barrier is via the interaction of the (sialyl-) Lewis x glycan structures present on the PER.C6™-produced EPO with E-selectin molecules present on human brain microvessel endothelial cells (Lou et al. 1996). Interaction between E-selectin and EPO may facilitate the transport of EPO across the cerebral endothelial barrier since E-selectin also has been implicated in the migration of T lymphocytes into the CNS (Wong et al. 1999). If required for optimal neuro-protection, PER.C6™-produced EPO can be administered at a significantly higher dose than serum-type EPO, because PER.C6™-EPO will induce erythropoiesis much less efficiently, such that the detrimental effects of the increase in hematocrit is reduced or even absent.

In another aspect of the invention, EPO produced on a mammalian cell that expresses E1A, such as PER.C6™-EPO, can be administered intrathecally by infusion, or through an indwelling ventricular catheter, or through lumbar injection, to inhibit or prevent neural damage. Again, the advantage of using brain-type EPO over serum-type EPO is that in the event of leakage into the blood circulation in the case of blood-brain barrier dysfunction, due to for instance stroke, no undesired side-effects with respect to erythropoiesis will occur.

The present invention establishes that indefinitely growing transformed cells that grow to very high densities under serum-free conditions and that have neural characteristics, such as PER.C6™, are extremely useful to produce factors that depend for their functionality on these characteristics. This inherently also provides the possibility to produce factors that do not have neural features or neural-related functions but that nevertheless benefit from the post-translational modifications that are brought about by such cells. One can envision that some factors also play a role in non-neural tissue but that still require glycosylation structures that include for instance Lewis x structures or fucose residues as described for EPO in the present invention and that can be provided by the means and methods of the present invention. Examples of factors that might be produced by PER.C6™ and that take advantage of the neural characteristics of PER.C6™ cells include, but are not limited to, brain-type erythropoietin, transferrin and the different factors mentioned above. The invention shows that it is very likely that the production of other recombinant neurotrophic glycoproteins will benefit from the brain-type modifications that take place in such cells.

In accordance with the present invention it has surprisingly been found, that erythropoietin-like molecules having on average a lower sialic acid residue count per protein backbone are still effective in the treatment and/or prevention of various disorders. This opens entirely new ways to use EPO and EPO-like molecules hitherto believed to of less or no use, including but not limited to low-sialyl EPO-fractions of EPO batches produced on recombinant mammalian cell systems, discarded upon fractionation because of their low average sialylation degree and/or low associated erythropoietic activity. Thus, the present invention demonstrates that EPO with a low sialic acid content is about as potent in reducing infarct size in an experimentally induced stroke in rats as EPO with a higher sialic acid content. It is well established in the art that a high sialic acid content of EPO correlates to longer circulatory half-lifes and increased erythropoietic potential in vivo (Tsuda et al. 1990; Morimoto et al. 1996).

Hence, in general terms, the invention provides the use of a composition of erythropoietin-like molecules selected from the group consisting of erythropoietin, one or more muteins of erythropoietin, one or more derivatives of erythropoietin, and a composition of one or more fractions of erythropoietin molecules sialylated to a varying degree, for the preparation of a medicament for the treatment of a disorder selected from the group consisting of ischemia, a reperfusion injury, a hypoxia-induced disorder, an inflammatory disease, a neurodegenerative disorder, and acute damage to the central- or peripheral nervous system, wherein said composition of erythropoietin-like molecules has on a protein content basis a lower erythropoietic activity in vivo than epoetin alfa and epoetin beta. Embodiments of the invention comprise compositions and use thereof wherein said erythropoietic activity in vivo is at least 10, 20, 30, 40, 50, 60, 70, 80, or 90% lower than that of epoetin alfa (Eprex) or epoetin beta. Erythropoietin-like molecules are meant to include molecules that have a protein backbone that is identical to or similar to the presently known forms of EPO, e.g. EPO muteins, EPO derivatives, or EPO molecules differing in glycosylation of the protein backbone in qualitative and/or quantitative respect. Muteins as used herein are meant to consist of erythropoietin-like molecules that have one or more mutations in the protein backbone by deletion, addition, substitution and/or translocation of amino acids relative to the protein backbone of epoietin alfa and shall include naturally occurring allelic variants as well as genetically and/or chemically and/or enzymatically obtained variants. Such molecules should still be able to confer a functional activity of EPO. They are obtainable using standard techniques of molecular biology, well known to those of skill in the art. A derivative as used herein is an erythropoietin-like molecule that is obtainable from erythropoietin or epoietin alfa, or any other functional mutein of epoietin alfa by the chemical or enzymatic modification thereof. Erythropoietic activity as meant herein is the stimulatory effect of EPO on red blood cell production in a human or animal subject, as can be measured by the increase in hematocrit values at a certain point in time after administration to the human or animal subject of erythropoietin-like molecules (e.g see example 9), or the measuring the hemoglobin concentration. These methods are all well known those of skill in the art. Epoetin alfa is the recombinant human EPO form present in currently marketed Eprex-™, and is similar or identical (with respect to amino acid and carbohydrate composition) to human erythropoietin isolated from urine of anemic patients. Treatment regimes for erythropoietic purposes are well established. In general EPO dosages are given in IU (international units), referring to the activity of EPO in erythropoiesis. Such IU correlate to the protein content of EPO but are operationally defined, and hence the correlation may vary between different batches. As a rule of thumb, one IU corresponds to 8-10 ng epoetin alfa. For the purpose of describing the invention the erythropoietic activity of the erythropoietin-like molecules is referred to on a protein content basis, to get rid of the variable introduced by defining IU. It will be clear to the person skilled in the art that although the IU are usually given for commercial EPO preparations, the concentration of EPO molecules in such preparations can easily be defined according to standard procedures. This will allow to determine the relative specific activity e.g in IU/g (see e.g. EP 0428267). Several in vivo and in vitro assays useful for these purposes are also described by Storring et al. (1992). Examples of other forms of EPO currently on the market are Procrit or Epogen (both epoetin alfa) and Aranesp (darbepoetin alfa, EPO with extra N-glycosylation sites to increase circulatory half-life and erythropoietic activity). Although the erythropoietic activity may vary somewhat between the various commercial epoetin alfa and epoetin beta preparations on the market, they are generally optimized for high erythropoietic activity. The present invention discloses the use of EPO-like molecules or EPO-forms that have a lower hemopoietic or erythropoietic activity, thereby diminishing or avoiding the side-effects of increased erythropoiesis when this is not desired.

According to another embodiment of the invention, a composition of erythropoietin-like molecules is characterized by an average number of sialic acid residues per erytropoetin-like molecule that is at least 10% lower than the average number of sialic acid residues per erythropoietin molecule in epoetin alfa. According to other embodiments, said average number of sialic acid residues may be chosen to be at least 20%, 30%, 40%, 50%, 60%, 70%, 80% or 90% lower than the average number of sialic acid residues per EPO protein backbone in epoetin alfa. Said average number of sialic acid residues in the erythropoietin-like molecule preferably lies between between 0 and 90% of the average number of sialic acid residues per EPO molecule in epoetin alfa, but the exact percentage may depend from disorder to disorder, and—sometimes—from patient to patient, as some patient—disorder combinations are less vulnerable to high hematocrit values than others. Alternatively, the number of sialic acid residues could be described per EPO-like molecule, e.g. 15, 14, 13, 12, 11, 10, 9, 8, 7, 6, 5, 4, 3, 2, 1 or 0 sialic acid residues per EPO-like molecule. Since the values are averages calculated for a composition that consists of epo-like molecules of varying degree of sialylation, non-integer values in between the mentioned values are possible to define the molecules according to the invention. The optimal range could be determined empirically without undue burden by the person skilled in the art. The average number of sialic acid residues per molecule or the sialic acid content of EPO can be determined according to published procedures, and are well known to persons skilled in the art. One possible procedure is described in EP 0428267. In brief, the sialic acid residues are cleaved from the EPO-like molecules by hydrolysis with 0.35 M sulfuric acid at 80° C. for 30 minutes, and the solutions are neutralized with sodium hydroxide prior to analysis. Alternatively, the sialic acids can be removed by enzymatic cleavage according to standard procedures. The amount of EPO is estimated using well known procedures e.g. by using commercially available protein assay kits (e.g. Bradford assay, Biorad) and standard curves using recombinant human EPO as a standard, absorbance at 280 nm, ELISA, RIA, and the like. Sialic acid content can be analyzed by the procedure of Jourdian et al. (1971). Alternatively, sialic acids can be analysed using High Performance Anion-Exchange Chromatography, using procedures well known to the skilled person (e.g. Analysis of Sialic Acids using High-Performance Anion-Exchange Chromatography, Application note number TN41, Dionex). The sialic acid content can be expressed as moles of sialic acid per mole of EPO, or an average number of sialic acid residues per EPO-like molecule. An indication for the average number of sialic acid residues per EPO-like molecule can also be given by iso-electric focusing (see example 4), which measures the pI.

Several ways can be envisaged to obtain erythropoietin-like molecules with an average lower number of sialic acid residues per erythropoietin-like molecule. These include, but are not limited to treatment of EPO-like molecules, e.g. produced recombinantly in any suitable host cell line, using enzymes that cleave off the sialic acid in particular, such as neuraminidases, or enzymes that cleave off more substituents (including sialic acid) of the glycosylation structures, such as e.g. N-glycanase F (removes whole N-glycan), endoglycosidase $F_2$ (removes bi-antennary structures), endoglycosidase $F_3$ (removes bi- and tri-antennary structures), and the like, or treatment of EPO-like molecules with chemicals, including but not limited to acids, that results in decrease of the average number of sialic acid residues per EPO-like molecule. In particular, a highly sialylated EPO fraction could be thus desialylated and used in the present invention. In yet another embodiment EPO-like molecules with an average lower number of sialic acid molecules are obtained by purifying or separating such forms from a mixture containing both higher and lower sialylated EPO. The currently used production systems generally result in such mixtures, and EPO that is intended for erythropoietic purposes is prepared by purifying the forms with a high average number of sialic acid residues. The present invention discloses use of other fractions from this process, i.e. the EPO forms with a lower number of sialic acid residues. Purifying or separating such fractions can be done using well-established techniques known to the skilled person, such as ion-exchange, affinity purification, and the like. The erythropoietin-like molecules of the invention are preferably produced recombinantly. This can be done in any suitable expression system, including but not limited to Chinese Hamster Ovary cells, Baby Hamster Kidney cells, human cells, such as HeLa, HEK293 or PER.C6™. Expression in lower eukaryotic cells such as insect cells or yeast is also possible. Production of EPO-like molecules having low sialic acid content may be performed on sialylation-deficient cell systems, by way of a natural lack of sialylating enzymes, such as certain prokaryotic hosts, or by mutagenesis or genetic modification of hosts otherwise capable of producing sialylated proteins. Methods and means to produce recombinant proteins are well documented and known to the person skilled in the art, and it will be clear to the skilled person that using a different source for the EPO-like protein is possible without departing from the scope of the invention. In one aspect of the invention, the EPO-like molecules are produced by methods according to the invention, thereby producing molecules with a predetermined post-translational modification. In another aspect of the invention, the composition comprising erythropoietin-like molecules is characterized by the presence of erythropoietin-like molecules that once administered parenterally to a human or an animal subject are cleared from the bloodstream at a faster rate than epoetin alfa and epoetin beta. Clearance from the bloodstream can be measured by methods well known in the art, e.g. by determining the half-life of a protein in blood such as done in example 18. In healthy volunteers epoetin alfa has a circulatory half-life of about 4 hours after repeated intravenous injections. A half-life of about 5 hours in patients with chronic renal insufficiency, and about 6 hours in children has been reported. Using the method of example 8, we measure a half-life of 180 min for epoetin alfa (Eprex). It should be clear to the skilled person that this method can be used to determine the half-life of the compositions of the invention, and express this half-life in hours or in a percentage of the half-life of the standard EPO (Eprex). Similar experiments are feasible in humans to determine the half-life in humans. Erythropoietin-like molecules with a lower ratio of tetra-antennary structures to bi-antennary structures will also have a shorter half life in plasma (Misaizu et al, 1995; Takeuchi et al, 1989). Production of EPO in cell lines that give rise to such lower ratios is feasible, or alternatively these forms are purified away from the forms containing more tetra-antennary structures. Such compositions comprising relatively more bi-antennary structures are also useful according to the invention. It will also be clear that one advantage of the current invention is that higher maximal concentrations of erythropoietin-like molecules in the circulation can be reached as compared to the currently used EPO forms such as Eprex, Procrit, NESP. If high concentrations of EPO-like molecules would be desired for said treatment, this can be done by administering high doses of the compositions of the invention, e.g. in the form of pharmaceutical preparations containing such high doses. Administering of similar doses on a protein content basis of the currently used EPO-like molecules would lead to higher erythropoiesis, which is an undesired side-effect for said treatments.

The invention also provides pharmaceutical compositions comprising said erythropoietin-like molecules, and methods for treatment or preventing disorders selected from said groups, as wel as compositions of erythropoietin-like molecules for the preventative and/or therapeutic treatment of the human or animal body.

EXAMPLES

Example 1

Studies on Expression of Marker Proteins in PER.C6™ Cells

The cells that were transformed with the E1 region of human Adenovirus type 5 and that resulted in the PER.C6 ™ cell line (as deposited under the provisions of the Budapest Treaty under number ECACC no. 96022940 at the European Collection of Animal Cell Cultures at the Center for Applied Microbiology and Research of Porton Down, UK on Feb. 29, 1996) were derived from a human embryonic retina. Retinas generally comprise a number of different cells types (at least 55 different neural subtypes), including neural and fibroblast-like cells (Masland 2001). In order to trace the cellular origin of PER.C6™, a study was performed to test the expression of marker proteins in or on the cells. These markers are known in the art to be characteristic for certain cell types and/or tissues. The marker proteins are given in Table I.

Marker protein expression was tested using antibodies directed against the marker proteins. In each experiment, a negative control (PER.C6™ cells not incubated with antibody) and a positive control were taken along. These positive controls are sections of human tissue known to express the marker protein (Table II).

PER.C6™ cells were cultured on glass slides in a medium chamber (Life Technologies, Nunc Lab-Tek, Chamber Slide, radiation sterilized, 2 medium chambers, cat.no. 154464A). PER.C6™ cells were seeded at 65-70% confluency (2 wells per culturing chamber) and cultured for 24 h at 37° C. (10% $CO_2$, 95% air). The medium was aspirated and. the glass slides with cells were washed with sterile PBS, removed from the medium chamber and air-dried. Cells were fixed on the glass slides by incubation in acetone for 2 min. After air drying, slides were wrapped in aluminum foil and frozen at a temperature lower than −18° C. until use.

Positive control tissues were obtained from banks of tissue slides prepared for routine use at the division of pathology, Academic Hospital Erasmus University (Rotterdam, The Netherlands). Frozen sections were prepared (5 μm) and fixed in acetone, according to routine procedures.

The primary antibodies, their respective marker proteins, the suppliers and the catalog numbers of the antibodies are given in Table III. The dilutions, also detailed in Table III, are made in Phosphate Buffered Saline (PBS), 1% Bovine Serum Albumin. Incubations of the slides with the primary antibody were done for 30 min at room temperature, rinsed with PBS and incubated with the secondary antibody. These secondary antibodies were either goat anti rabbit (DAKO E0432; 1:50 dilution) or goat anti mouse (DAKO E0433; 1:50 dilution), depending on the nature of the primary antibody used. The second antibody was conjugated with biotin. After rinsing with PBS, the slides were incubated with streptavidin-avidin/biotin complex conjugated with alkaline phosphatase (DAKO, K0376). After 30 min of incubation, the samples were rinsed with Tris/HCl pH 8.0, developed with fuchsin substrate chromagen (DAKO K0624) in the dark room for 30 min. Subsequently, the slides were rinsed with tap water for 2 min and counterstained with hematoxylin according to routine procedures well known to persons skilled in the art. Then, the slides were examined microscopically and scored for marker protein expression (negative or positive). The results are presented in Table IV. For neurofilament staining (positive) not all PER.C6™ cells did stain positive as a result of a different cell cycle- or maturation phase of the cell population. This is a normal observation for neurofilament stainings.

From the data obtained it was concluded that PER.C6™ cells are of neural origin since the cells stained positive for vimentin, synaptophysin, neurofilament, GFAP and N-CAM.

Example 2

Monosaccharide Composition of PER.C6™-EPO Derived N-glycans Compared to that of Eprex A first step in characterizing the N-glycan structures produced by PER.C6™ is the measurement of the molar ratio of the various monosaccharides. The monosaccharide analysis was performed using high performance anion exchange chromatography with pulsed amperometric detection (HPAEC-PAD). EPO samples, produced by PER.C6™-derived clones P7, P8, and C25 (P7 and P8 are described in WO 00/63403, and C25 was generated generally according to these methods, using Neomycin resistance gene as a selection marker [plasmid pEPO2001/Neo]) in DMEM and/or JRH medium, were selected for this analysis. Eprex (Jansen Cilag), which is the commercially available recombinant CHO-derived erythropoietin, was analyzed in parallel, and therefore used as a reference.

PER.C6™-EPO samples were purified by affinity chromatography using a column packed with C4 sepharose beads (bedvolume of 4 ml, Amersham Pharmacia Biotech) coupled with mouse monoclonal anti-EPO (IgG1) antibodies. Bound EPO molecules were eluted with 0.1 M glycine-HCl, pH 2.7, and resulting fractions were immediately neutralized by adding sodium/potassium phosphate buffer pH 8.0. Subsequently, the fractions containing EPO—were pooled and the buffer was exchanged to 20 mM Tris-HCl, containing 0.1% (v/v) Tween 20, by utilizing Hiprep 26/10 desalting columns (Amersham Pharmacia Biotech).

For glycan analyses, purified EPO samples were dialyzed overnight against MilliQ-grade water, and dried in a Speedvac evaporator. Dried EPO samples (quantities ranged from 39 to 105 μg) were dissolved in incubation buffer (1:1 diluted C3 profiling buffer, Glyko). Upon addition of sodium dodecyl sulfate (SDS) and beta-mercaptoethanol to final concentrations of 0.1% (w/v) and 0.3% (v/v), respectively, samples were denatured for 5 min at 100° C. Nonidet P-40 (BDH) was thereafter added to a final concentration of 0.75% (v/v), and EPO was deglycosylated overnight at 37° C., using N-glycanase F (mU, Glyko). Upon deglycosylation, released N-glycans were separated from proteins, salts, and detergents by using graphitized carbon black (Carbograph) SPE columns (Alltech), according to Packer et al. (1998).

Purified N-glycan chains were subjected to hydrolysis in 2 M trifluoroacetic acid (TFA) at 100° C. for 4 h. After hydrolysis, monosaccharides were dried in a Speedvac evaporator, washed with water, and again evaporated in a Speedvac. Dried monosaccharides were dissolved in 26 µl MilliQ-grade water. After addition of 6 µl deoxyglucose (100 nmol/ml), which was used as internal standard, samples (24.5 µl) were applied to an HPAEC-PAD BioLC system with a 2 mm-diameter CarboPac PA1 column (Dionex). The column was run isocratically in 16 mM NaOH (Baker) at a flow rate of 0.25 ml/min. The monosaccharide composition was calculated by comparing the profile with that obtained with a mixture of mono saccharide standards that consisted of fucose, deoxyglucose, galactosamine, glucosamine, galactose, and mannose.

The monosaccharide analysis showed that the glycosylation status of PER.C6™-EPO is significantly different from Eprex (Table V). The ratio of the indicated monosaccharides (Man=mannose, Fuc=fucose, GalNAc=N-acetyl-galactosamine, GlcNAc=N-acetyl-glucosamine, Gal=galactose) was normalized to 3 Man. The duplo values are given between brackets. The PER.C6™-EPO samples contain significant amounts of GalNAc, whereas the N-linked sugars of Eprex lack this residue. This suggests that PER.C6™-EPO contains so-called LacdiNAc (e.g., GalNAcβ1-4GlcNAc) structures. Another feature of PER.C6™-EPO is the relative abundance of fucose residues shown in Table V. This strongly indicates the presence of Lewis structures in the N-glycans of PER.C6™-EPO. In contrast, Eprex is known to be devoid of Lewis structures. Consequently, the amount of fucose found in Eprex can be solely attributed to N-glycan core fucosylation. Notably, the data from the monosaccharide analyses also demonstrated that culture conditions affect the glycosylation status of EPO in PER.C6™. It should not be concluded that the culture conditions are solely responsible for the predetermined post-translational modifications that are present on the proteins produced. Of course the cell lines should be able to modify the post-translational modifications of the proteins produced on such cells through the presence of certain specific glycosylation enzymes such as transferases. The culture conditions can only exert additive activities. For instance, when the EPO-producing clones were cultured (in suspension) in JRH Excell 525 medium, the N-linked glycans of EPO were found to contain higher levels of GlcNAc, GalNAc, Gal, and Fuc as compared to the N-linked sugars of EPO derived from cultured (adherent) cells in DMEM (Table V). This effect was particularly evident in the case of clone P8. The elevated level of GlcNAc may suggest that the branching of the N-linked sugars is increased and/or that the N-linked sugars contain more lactosamine repeats, when cells are cultured in JRH medium. The increase in N-acetyl glucosaminylation and in (N-acetyl-) galactosylation in turn gives rise to an increased number of fucose-acceptor sites thereby providing an explanation for the increase of the Fuc content.

Example 3

Mass Spectrometric Analysis to Reveal Structural Differences Between N-glycans of PER.C6™-EPO and Eprex To obtain more detailed information on the structure of the N-glycans produced by PER.C6™, it was decided to analyze the complete sugar chains of PER.C6™-EPO by MALDI-MS. For this analysis, affinity-purified EPO samples, made by PER.C6™-derived clones P7 and P8 in DMEM, which were fractionated further by anion exchange chromatography (as described below) were utilized. PER.C6™-EPO samples, affinity-purified as described in example 2, of which the buffer was thereafter exchanged to PBS, were subjected to anion exchange chromatography using a HiTrap sepharose Q HP column (Amersham Pharmacia Biotech). Three EPO subfractions were obtained by applying a step gradient in 20 mM Tris-HCl/20 µM $CuSO_4$, beginning with 45 mM NaCl (fraction 1), followed by 75 mM NaCl (fraction 2), and ending with 135 mM NaCl (fraction 3). Each step of the gradient lasted 10 min with a flow rate of 1 ml/min. Fractions 1 of four runs were pooled into pool A, fractions 2 into pool B, and fractions 3 into pool C. The resulting pools A, B, and C were thereafter desalted utilizing HiPrep 26/10 desalting columns (Amersham Pharmacia Biotech). The N-linked glycans were released from the EPO pools by N-glycanase F treatment and desialylated by neuraminidase treatment. Eprex was analyzed in parallel as a reference. Representative mass spectra of the various EPO samples are shown in FIG. 1A-G: Eprex and the purified, fractionated (pools A, B, and C from the anion exchange chromatography column). PER.C6™-EPO samples derived from the indicated clones cultured in DMEM were treated with glycanase F and neuraminidase, and thereafter analyzed by MALDI-MS. Symbols (depicted in the spectrum of Eprex) are: closed square is GlcNAc, open circle is Man, closed circle is Gal, open triangle is Fuc. The mass profile of the N-linked sugars of Eprex (FIG. 1A) corresponds to previously published data and indicates that tetra-antennary sugars with or without lactosamine repeats predominate in this EPO preparation. Although Eprex and PER.C6™-EPO contain sugar structures with a similar mass (FIG. 1B-G), the profile of the sugar structures of the latter is much more complex, suggesting that these sugars display a large degree of heterogeneity. The ExPAsy's computer program was used to predict the sugar composition on basis of the observed mass (Table VI and VII). The relative abundance of the different oligo-saccharides in each pool was also presented. The data demonstrated that most N-linked oligosaccharides derived from PER.C6™-EPO contain multiple fucose residues (Table VI and VII, see level of dHex residues). Some glycans were even quadruple-fucosylated. Consequently, these data are in line with our monosaccharide analyses and strongly suggest that PER.C6™-EPO is hyperfucosylated, and, hence, most likely decorated extensively with N-glycans having so-called Lewis structures. Oligosaccharides with (sialylated) Lewis x epitopes are known as essential recognition sequences for selecting, mediating cell-cell adhesions in both inflammatory and immune responses (Varki et al. 1999) and are characteristically found in brain glycoproteins (Margolis and Margolis 1989). Hence, numerous glycoproteins carrying these Lewis x structures have been shown to have therapeutic potential by exhibiting anti-inflammatory and immunosuppressive activities. It is noted here that a mass signal cannot always be unambiguously assigned to a certain sugar structure: e.g. residues like GlcNAc and GalNAc have the same mass. Because the monosaccharide analysis of PER.C6™-EPO revealed the occurrence of GalNAc in the N-linked sugars, it is expected that some of the peaks represent N-glycans with so-called LacdiNAc (e.g., GalNAcβ1-4GlcNAc) structures. For example, peaks with m/z values of ~2038 and ~2185 (Table VI and VII) most likely represent N-glycans with LacdiNAc motifs. Otherwise, these peaks would represent tetra-antennary structures, which terminate in GlcNAc due to the absence of Gal or GalNAc. Although such structures may be present due to incomplete glycosylation, the presence of the proximal Fuc implies that the sugar contained a Gal or GalNAc residue that is necessary to form a motif that is recognized by the fucosyltransferase (FUT) that catalyzes the formation of the Lewis structure.

The relative occurrence of the different sugars varies between the EPO preparations derived from two independent PER.C6™ clones as judged by the difference in the relative height of certain peaks. In particular, the putative bi-antennary sugars with LacdiNAc motifs (FIG. 1; Table VI and VII, signals with m/z values of ~2038 and ~2185) are the major sugars in EPO samples derived from P8, whereas in P7 samples these structures are far less abundant. In the latter clone, the peak with an m/z value of ~2541, putatively corresponding to a fully galactosylated tetra-antennary glycan, was the most abundant structure. These data are in accordance with our monosaccharide analyses, which already indicated that, when grown in DMEM, P8 produced EPO carrying glycans with a lower degree of branching than those derived from P7-EPO (Table V).

Example 4

Comparison of Sialic Acid Content of PER.C6™-EPO and CHO-EPO

The sialic acid content of PER.C6™-EPO was analyzed and compared with erythropoietin derived from Chinese Hamster Ovary cells (CHO-EPO) by iso-electric focusing (IEF) using IPG strips (Amersham Pharmacia Biotech) that have a linear pH gradient of 3-10. After the focusing, the EPO isoforms were passively blotted onto nitrocellulose, and visualized using an EPO-specific antibody and ECL (FIG. 2). EPO made by four different PER.C6™ clones (lanes C, D, E, and F), and three different CHO clones stably expressing EPO (lanes G, H, and I) were analyzed by iso-electric focusing to determine the sialic acid content. The EPO producing CHO and PER.C6™ cell lines were generated generally according to methods described in WO 00/63403 using the Neomycine-resistance gene as a selection marker. One thousand eU of PER.C6™-EPO and 500 eU of CHO-EPO were loaded per strip. Five hundred IU of Eprex (lane A) and neuraminidase-treated (partially desialylated) Eprex (lane B) were used to identify the various EPO-isoforms. After focusing, EPO was blotted onto nitrocellulose filter and visualized using a monoclonal antibody against EPO and ECL. The Eprex sample, representing a commercially available EPO is a formulation containing highly sialylated isoforms and was used as a marker.

The results demonstrated that CHO cells are able to make EPO isoforms containing up to at least 12 sialic acids per molecule (lanes G-I), confirming data by Morimoto et al. (1996). In contrast, although some isoforms with 8-10 sialic acids were produced by PER.C6™, these were underrepresented and only detectable after prolonged exposure of the film (lanes C-F). Consequently, it can be concluded that PER.C6™-EPO is considerably less sialylated than CHO-EPO.

Example 5

α1,3-, α1,6- and α1,2-fucosyltransferase Activities on PER.C6™ Cells

The glycosylation potential of a cell is largely determined by an extensive repertoire of glycosyl-transferases involved in the step-wise biosynthesis of N- and O-linked sugars. The activity of these glycosyl-transferases varies between cell lines and, hence, glycoproteins produced in different cell lines acquire different glycans. In view of the data shown herein, demonstrating that PER.C6™-EPO glycans are heavily fucosylated, the activity of numerous fucosyltransferases (FUTs) involved in the synthesis of N-linked sugars was analyzed using methods generally known to persons skilled in the art (Van den Nieuwenhof et al. 2000). In this study, we studied the activities of α1,6-FUT, which is involved in core fucosylation of N-glycans, α1,2-FUT which mediates the capping of terminal galactose residues, giving rise to so-called Lewis y epitopes, and α1,3-FUT, which generates Lewis x structures. For comparison, we also analyzed the corresponding FUT activities present in CHO cells.

The activities of the indicated FUTs in cell-extracts of PER.C6™ and CHO were measured using a glycosyltransferase activity assay. This assay measures the glycosyltransferase-catalyzed reaction between a saccharide (in this case fucose) and a sugar substrate. The GalT activity was also measured as an internal control. The values represent the mean values from two experiments. All values, and in particular those of PER.C6™ were 2-3 fold lower in the second experiment. Notably, the activities were expressed per mg protein (present in the cell extract). Because PER.C6™ cells are significantly bigger than CHO cells, the differences between the FUT and GalT activities of CHO and PER.C6™ cells may be bigger or smaller than they appear. The results of the glycosyltransferase activity assays are shown in Table VIII and reveal that PER.C6™ as well as CHO possess significant α1,6-FUT activity, which suggests that both cell lines can produce core-fucosylated glycan chains. α1,3-FUT activity was, however, only significant in PER.C6™ cells while hardly detectable in CHO cells. None of the two cell lines exhibited α1,2-FUT activity. Taken together, these data show a difference between the glycosylation potential of CHO and PER.C6™, and explain why PER.C6™-EPO contains more fucoses than CHO-produced EPO (Eprex).

Example 6

Glycans with Lewis x Epitopes Present on PER.C6™-EPO.

Because PER.C6™ possesses α1,3-, but no α1,2-fucosyltransferase activity, it is very likely that PER.C6™ produced N-glycan chains which contain Lewis x instead of Lewis y epitopes. We verified this by labeling PER.C6™-EPO with a mouse monoclonal antibody (anti-Lewis x, human IgM; Calbiochem) that specifically recognizes Lewis x structures, using western blotting. Equal amounts of PER.C6™-EPO (derived from clone P7, here indicated as P7.100) and Eprex, untreated (−) or treated with HCl (+), were run on a SDS-polyacrylamide gel and blotted onto a nitrocellulose membrane using methods known to persons skilled in the art. A monoclonal antibody (anti-mouse IgM, Calbiochem) and ECL (Amersham Pharmacia Biotech) were used to detect the Lewis x epitope. As can be seen in FIG. 3, only PER.C6™-EPO could be labeled with the antibody specific for the Lewis x epitope. Location of the molecular weight marker (52, 35 and 29 kDa) is indicated. Because the α1,3-fucose linkage is acid-labile, the signal was lost after treatment with HCl.

Example 7

Lewis x Structures Expression at Cell Surface of PER.C6™ Cells

To find out whether Lewis x structures generally occur in PER.C6™ cells, we labeled the surface of CHO and normal (i.e., not EPO producing) PER.C6™ cells with Lewis x specific antibodies (Calbiochem). The cells were incubated with the primary antibodies (mAb α Lewis x used at 0.16 µg/ml, and mAb α sialyl-Lewis x used at 5 µg/ml). FITC-conjugated anti-IgM was used as a secondary antibody. The labeled cells were analyzed by FACS. The dashed line represents the signal of cells incubated with the secondary antibody only (negative control). The results shown in FIG. 4 revealed that PER.C.6™ cells were strongly labeled with the antibodies in contrast to CHO cells that are unable to produce these structures. Notably, we repeatedly observed that PER.C6™ cells displayed a heterogeneous pattern of staining with the Lewis x antibodies. Labeling with an antibody specific for sialyl Lewis x structures (Calbiochem) gave a moderate positive signal only when a very high concentration of the antibody was used.

Example 8

Inhibition of Apoptosis by PER.C6™-EPO (Brain-type) in vitro, in NT2 Cells and hNT Cells Cultured Under Hypoxic Conditions PER.C6™-produced (brain-type) EPO and serum-type EPO are compared in their in vitro activity to protect rat-, mouse- and human cortical neural cells from cell death under hypoxic conditions and with glucose deprivation. For this, neural cell cultures are prepared from rat embryos as described by others (Koretz et al. 1994; Nagayama et al. 1999; White et al. 1996). To evaluate the effects of PER.C6™-produced brain-type EPO and serum-type EPO, the cells are maintained in modular incubator chambers in a water-jacketed incubator for up to 48 h at 37° C., in serum-free medium with 30 mM glucose and humidified 95% air/5% $CO_2$ (normoxia) or in serum-free medium without glucose and humidified 95% $N_2$/5% $CO_2$ (hypoxia and glucose deprivation), in the absence or presence of 30 pM purified PER.C6™-produced brain-type EPO or 30 pM Eprex. The cell cultures are exposed to hypoxia and glucose deprivation for less than 24 h and thereafter returned to normoxic conditions for the remainder of 24 h. The cytotoxity is analyzed by the fluorescence of Alamar blue, which reports cells viability as a function of metabolic activity.

In another method, the neural cell cultures are exposed for 24 h to 1 mM L-glutamate or α-amino-3-hydroxy-5-methylisoxazole-4-propionic acid (AMPA) under normoxic conditions, in the absence or presence of various concentrations of purified PER.C6™-produced EPO or Eprex. The cytotoxity is analyzed by the fluorescence of Alamar blue, which reports cell-viability as a function of metabolic activity. The viability of cells treated with PER.C6™-EPO is expected to be similar to the viability of cells treated with Eprex.

Example 9

Activity of PER.C6™-EPO (Brain-type) in Stimulating Erythropoiesis in Rats Compared to Serum-Type EPO The potential of recombinant human EPO to stimulate the production of red blood cells can be monitored in a rodent model that has been described by Barbone et al. (1994). According to this model, the increase in the reticulocyte counts is used as a measure for the biological activity of the recombinant human EPO preparation. Reticulocytes are the precursors of red blood cells and their production, in response to EPO, can be used as a measure for the potential of EPO in stimulating the production of red blood cells. An increased production of red blood cells, in turn, leads to a higher hematocrit value.

The activities of PER.C6™-EPO and Eprex were compared in six groups of three Wag/Rij rats. Various doses of PER.C6™-EPO (P7-EPO), Eprex and diluent buffer as a negative control were injected intravenously in the penile vein at day 0, 1, and 2. PER.C6™-EPO was administered at a dose of 5, 25, or 125 eU (Elisa units) as determined by the commercially available EPO-specific R&D Elisa Kit, whereas Eprex was administered at a dose of 1 or 5 eU. All EPO preparations were diluted to the proper concentration in PBS/0.05% Tween 80 in a total volume of 500 µl. At day 3, 250 µl of EDTA blood was sampled by tongue puncture. On the same day, the percentage of reticulocytes in the total red blood cell population was determined.

As shown in FIG. 6 (bars indicate the percentage of reticulocytes present in the total red blood cell population), the daily administration of 1 eU of Eprex into the rats, for a total period of three days, caused a significant increase in the reticulocyte counts at the fourth day compared to reticulocyte counts in rats that received diluent buffer only. The reticulocyte counts were even more boosted by increasing the Eprex dose five-fold. The reticulocyte counts were clearly less increased using equivalent amounts of PER.C6™-EPO. A similar increase in reticulocyte counts was observed when 1 eU of Eprex and 25 eU of PER.C6™-EPO was used indicating that PER.C6™-EPO is at least 25 times less active in stimulating the red blood cell production than Eprex. The difference between the potential of Eprex and PER.C6™-EPO in stimulating the red blood cell production was even more pronounced at a higher dose (i.e. 5 eU Eprex and 125 eU PER.C6™-EPO).

Example 10

Effect of PER.C6™-EPO on Cerebral Ischemia Following Experiment Subarachnoid Hemorrhage To show that PER.C6™-EPO is more effective in neuroprotection during cerebral ischemia than serum-type EPO, we compare the effects of systemic adminstration of PER.C6™-produced brain-type EPO and serum-type EPO in a rabbit model of subarachnoid hemorrhage induced acute cerebral ischemia. Therefore, 32 animals that are divided into 4 groups (n=8) are studied.

Group 1, subarachnoid hemorrhage;
Group 2, subarachnoid hemorrhage plus placebo;
Group 3, subarachnoid hemorrhage plus recombinant human serum-type EPO; and
Group 4, subarachnoid hemorrhage plus recombinant PER.C6™-produced EPO.

The experimental subarachnoid hemorrhage is produced by a percutaneous injection of autologous blood into the cisterna magna after anesthesizing the animal. After the injection, the rabbits are positioned in ventral recumbence for 15 min to allow ventral blood-clot formation. Animals of group 2, 3, and 4 are injected with diluent buffer, Eprex, and purified PER.C6™-produced brain-type EPO, respectively, at 5 min after the induction of subarachnoid hemorrhage, and are continued at 8, 16, and 24 h thereafter. All injections are administered intra-peritoneally. The diluent buffer consists of serum albumin (2.5 mg/ml), sodium chloride (5.84 mg/ml), anhydrous citric acid (0.057 mg/ml, $H_2O$). The animals are euthanized at 24 h after the subarachnoid hemorrhage, and their brains are removed. The brains are thereafter coronally sectioned at 10-25 µm in a freezing microtome, starting at the bregma and continuing posteriorly to include the cerebellum (Ireland and MacLeod 1993). To visualize and assess the number of ischemia-induced damaged neurons, the slices are stained with hematoxylin and eosin. The number of eosinophilic neuronal profiles containing pyknotic nuclei, per high-power microscopic field (100×) is determined in five randomly selected sections of the lateral cortex obtained at several coronal levels posterior to the bregma. PER.C6™-EPO treated animals are expected to have a lower number of damaged neurons than animals that are not treated or that are treated with a placebo.

Example 11

Erythropoietin Receptor Expression in Rat Neonatal Cardiomyocytes Following Hypoxia/Reoxygenation Primary cultures of neonatal rat cardiomyocytes are prepared from the ventricles of 1-day-old Sprague-Dawley rats, as previously described (Simpson and Savion 1982). Hypoxia was created by incubating the cardiomyocytes in an airtight Plexiglas chamber with <1% $O_2$ and 5% $CO_2$/95% $N_2$ at 37° C. for 2 h using Gas Pak Plus (BBL). By replacing the medium saturated with 95% air and 5% $CO_2$, the cells were exposed to normotoxic atmosphere (reoxygenation).

Cardiomyoctes are washed twice with ice-cold PBS and total RNA is isolated using Trizol (GIBCO), extracted by chloroform and precipitated by isopropyl alcohol. For Northern analysis, 15 µg of total RNA is separated on a 1.5% formaldehyde/MOPS-agarose gel, blotted to nitrocellulose, and hybridized with a $^{32}P$-labeled probe for EPO receptor (±400 bp cDNA fragment). Hybridization takes place overnight at 65° C. in phosphate buffer, pH 7.2 and is followed by 2 washes in 2×SSC at room temperature, 2 washes in 0.2×SSC/0.1% SDS at 65° C. and 2 washes in 2×SSC at room temperature. Hybridization signals are visualized by exposing the membrane to an X-ray film (Kodak). Expression levels are corrected for GAPDH mRNA levels.

Example 12

The Effect of Brain-type PER.C6™-EPO and Serum-type EPO (Eprex) on Apoptosis in Rat Neonatal Cardiomyocytes, Cultured under Hypoxic Conditions Primary cultures cultures of neonatal rat cardiomyocytes are prepared from the ventricles of 1-day-old Sprague-Dawley rats as previously described (Simpson and Savion 1982). Hypoxia is created by incubating the cardiomyocytes in an airtight Plexiglas chamber with <1% $O_2$ and 5% $CO_2$/95% $N_2$ at 37° C. for 2 h using Gas Pak Plus (BBL) By replacing the medium saturated with 95% air and 5% $CO_2$, the cells are exposed to normotoxic atmosphere (reoxygenation). The experiment is divided into 4 groups:
  A) cardiomyocytes cultured under normoxic conditions (95% air/5% $CO_2$);
  B) cardiomyocytes cultured under hypoxia/reoxygenation conditions in the presence of 30 pM purified PER.C6™-produced EPO;
  C) cardiomyocytes cultured under hypoxia/reoxygenation conditions in the presence of 30 pM purified Eprex; and
  D) cardiomyocytes cultured under hypoxia/reoxygenation conditions in the absence of EPO.

All experiments are performed in triplicate. Apoptosis is quantified by morphological analysis, DNA laddering and by terminal deoxyribonucleotide transferase-mediated dUTP nick end labeling (TUNEL). For morphological analysis myocytes monolayers are fixed and stained with Hoechst 33324. The morphological features of apoptosis (cell shrinkage, chromatin condensation, and fragmentation) are monitored by fluorescence microscopy. At least 400 cells from 12 randomly selected fields per dish are counted.

For determining DNA laddering (characteristic for apoptosis), cardiomyocytes are lysed in lysis buffer and electrophoresed on 2% agarose gel. The gel is stained with ethidium bromide, and DNA fragments are visualized under ultraviolet light. In situ detection of apoptotic cardiomyocytes is performed by using TUNEL with an in situ cell death detection kit (Boehringer Mannheim).

Example 13

The Effect of PER.C6™-EPO and Serum-EPO on the Infarct Size in a Rat Model of Myocardial Ischemria/Reperfusion Adult male Sprague-Dawley rats (300 to 400 g) are anesthetized with sodium pentobarbital (20 mg/kg IP) and ketamine HCl (60 mg/kg IP). Jugular vein and trachea are cannulated, and ventilation is maintained with 100% oxygen by a rodent ventilator adjusted to maintain exhaled $CO_2$ between 3.5% and 5%. A left thoracotomy was performed and a suture was placed 3 to 4 mm from the origin of the left coronary artery. Five minutes before ischemia animals are randomly given various concentrations of PER.C6™-EPO, serum-type EPO or saline (n=6 for each group). Ischemia (30 min) is initiated by tightening of the suture around the coronary artery and is followed by 4 h of reperfusion. Sham-operated rats are prepared identically, except that the suture is not tightened (n=6).

After reperfusion, infarct size is determined by differential staining with patent blue violet (5%) and triphenyl tetrazolium chloride (TTC). The coronary ligature is retightened, and an intravenous injection of patent blue violet is given to stain the normally perfused regions of the heart. The heart is then removed and bathed in ice-cold saline before removal of the atria, great vessels and right ventricle. The left ventricle is sliced into thin sections, and the unstained are at risk (AAR) is separated from the normally perfused blue sections, cut into 1-2 $mm^3$ pieces, and incubated with TTC. With a dissecting microscope, the necrotic areas (AN, pale) are separated from the TTC-positive (brick red-staining) areas. All areas of the myocardium are then weighed individually, and infarct size is calculated.

Example 14

Isolation and Fractionation of PER.C6™-EPO Glycoforms Containing a High α1,3-Linked Fucose Content The fucose-specific *Aleuria aurantia* lectin (AAL) was used to preferentially purify PER.C6™-EPO glycoforms with a high Lewis x and/or sialyl-Lewis x content. EPO that was secreted into the culture medium by EPO-producing PER.C6™ cells was first cleared from cell debris and other contaminants by affinity column chromatography using monoclonal antibodies specific for human EPO (see example 2). Thereafter, about 270 μg (or 27,000 eU) of the purified EPO was subjected to a second chromatography procedure in which the EPO molecules were bound to a column containing the immobilized AAL at 0.1 ml/min (AAL Hitrap column 1 ml, Bio Med Labs). EPO glycoforms carrying fucose were eluted from the column by using L-fucose (Sigma) as a competitor for binding to AAL. Four EPO subfractions were obtained by applying a step gradient in PBS (Gibco, containing 154 mM NaCl, 1.05 mM $KH_2PO_4$ and 3.0 mM $Na_2HPO_4$, pH=7.4), beginning with 60 μM fucose (fraction 1), followed by 200 μM fucose (fraction 2), followed by 400 μM fucose (fraction 3), and ending with 1000 μM fucose (fraction 4). The first step of the gradient lasted 10 min and the other steps lasted 5 min with a flow rate of 0.5 ml/min. The UV signal at 214 nm of the chromatogram showed that material eluted from the column in every fraction (see FIG. 9). 0.5 ml portions were collected and two or three peak fractions were pooled (see FIG. 9).

Figure 10B:
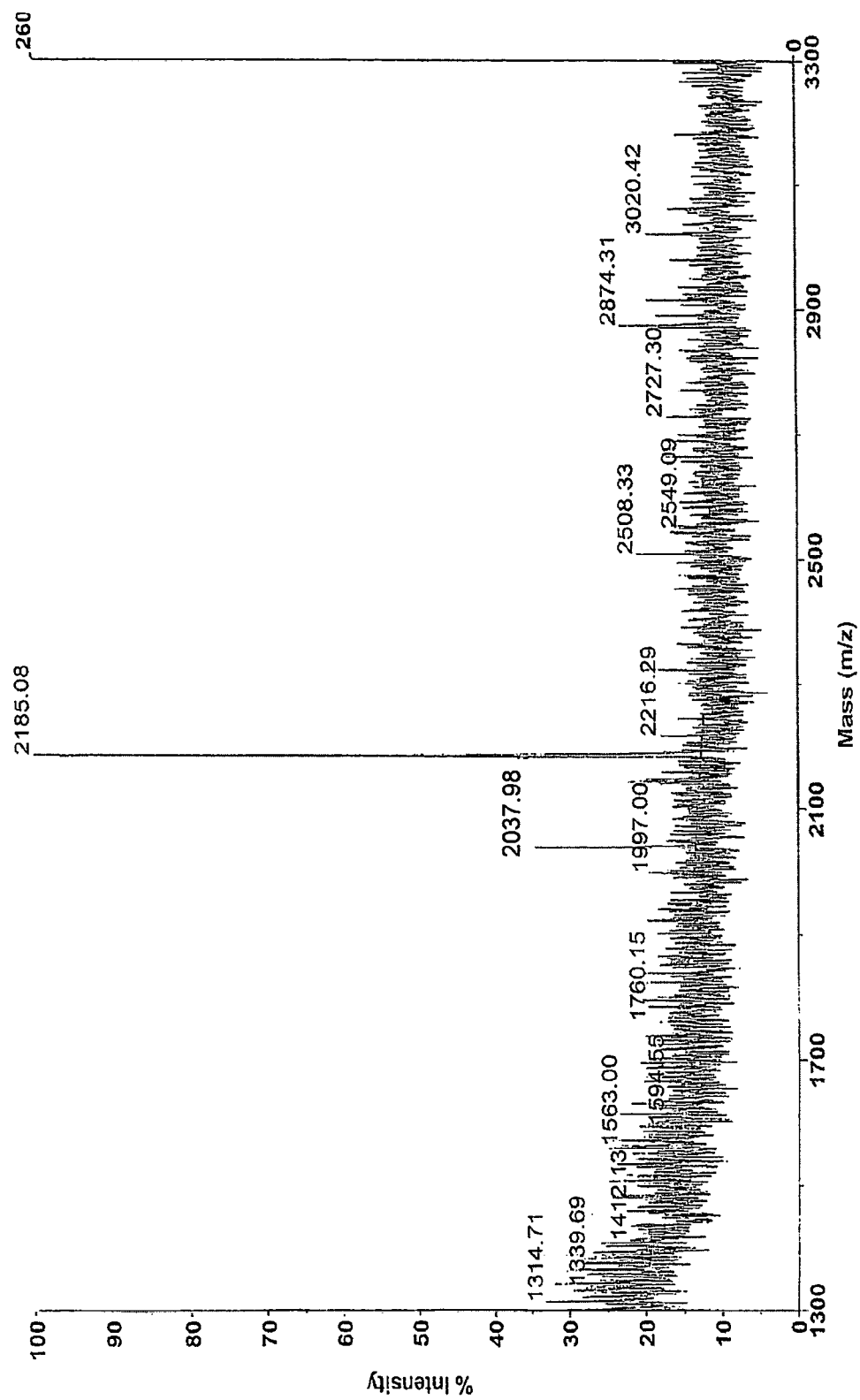

The buffer of the fractions was exchanged using a 10 kDa microcon (Millipore) to 20 mM phosphate and the fractions were concentrated on the same microcon to 20-30 μl. The N-linked glycans were released from the EPO pools by N-glycanase F treatment and desialylated by neuraminidase treatment. Representative MALDI-TOF MS spectra of the various EPO samples are shown in FIG. 10A. The relative abundance of the different oligosaccharides in each pool was also presented (see Table IX). The data demonstrate that the fractions eluting later from the AAL column contain relatively more fucose residues. For example, the fractions eluting later from the column are enriched in glycans giving rise to peaks at 2507.9 and 2978.1 Dalton, which contain 3 or 4 fucose residues, while glycans with a mass of 1891.7 and 2215.8, which contain only 1 fucose residue, are relatively underrepresented in these fractions. Therefore, these fractions are enriched with N-glycans having so-called Lewis X structures. The average number per EPO-molecule of Lewis X structures on N-linked glycans that was released using PNGaseF and detected with MALDI-TOF MS was for this experiment: 2.2 for fraction 1, 2.7 for fraction 2, 3.6 for fraction 3, 4.1 for fraction 4. The starting material contained 2.6 Lewis X structures per EPO molecule. In an independent experiment with clone C25, a fraction 4 was obtained (spectrum in FIG. 10B) that was even more enriched for Lewis X structures, having 5.7 lewis X structures on N-linked glycans per EPO molecule. This method enables one to purify erythropoietin from the culture medium by employing the specific characteristics of the post-translational modifications, such as Lewis x structures brought about by the cells in which the protein is produced. This does however, not imply that other methods cannot be employed for proper purification of the protein with the (predetermined) post-translational modifications.

The material eluted in fraction 4 represents a novel form of EPO; it contains predominantly N-linked glycans with a mass of ~2185 kDa, which in turn corresponds to a complex bi-antennary N-linked sugar with GalNAc-Lewis x structures on both antennae. Fraction 4 contained about 8% of the total EPO that had been eluted in fraction 1-4. This indicates that the novel form of EPO with predominantly bi-antennary GalNAc-Lewis x structures represents a low abundant form of EPO, which can be enriched using the above described method.

Example 15

Isolation and Fractionation of PER.C6™-EPO Glycoforms with a High LacdiNAc Content PER. C6™-EPO glycoforms carrying so-called lacdiNAc oligosaccharide structures are specifically isolated by the use of monoclonal antibodies against these lacdiNAc structures. Mouse monoclonal antibodies such as 99-2A5-B, 100-2H5-A, 114-2H12-C, 259-2A1, and 273-3F2 (Van Remoortere et al. 2000) specifically recognize lacdiNAc structures and are purified and coupled to CNBr-activated Sepharose 4B beads according to procedures commonly known by a person skilled in the art. PER.C6™-EPO that is secreted into the culture medium by human EPO-producing PER.C6™ cells is first roughly separated from cell debris and other contaminants by affinity column chromatography using monoclonal antibodies specific for human EPO. Thereafter, the purified EPO is subjected to a second chromatography procedure in which the EPO molecules carrying lacdiNAc structures are bound to a column containing the immobilized lacdiNAc-specific monoclonal antibodies. EPO glycoforms that lack the lacdiNAc structures do not bind to the column and are collected in the flow-through. EPO glycoforms carrying the lacdiNAc structures are eluted from the column at a low pH or by using GalNAc or synthetic lacdiNAc oligosaccharides as a competitor for binding to the lacdiNAc specific antibodies. EPO glycoforms carrying a relatively high percentage of lacdiNAc structures are separately eluted from the column by increasing the GalNAc or lacdiNAc concentration step-wise or gradually during the elution. EPO glycoforms with a relatively high percentage of lacdiNAc structures are eluted at a higher concentration of GalNAc or lacdiNAc than EPO glycoforms possessing a relatively low percentage of lacdiNac structures. In accordance with the method described above, also this method enables one to purify erythropoietin from the culture medium by employing the specific characteristics of the post-translational modifications, such as Lewis x and lacdiNac structures brought about by the cells in which the protein is produced.

Example 16

Isolation and Fractionation of PER.C6™-EPO Glycoforms with a High GalNAc-Lewis x Content PER.C6™-EPO glycoforms carrying so-called GalNAc-Lewis x oligosaccharide structures are specifically isolated by the use of monoclonal antibodies against these GalNAc-Lewis x structures. Mouse monoclonal antibodies such as 114-5B1-A, 176-3A7, 290-2D9-A, and 290-4A8 (Van Remoortere et al. 2000) specifically recognize GalNAc-Lewis x structures and are purified and coupled to CNBr-activated Sepharose 4B beads according to procedures commonly known by persons skilled in the art. PER. C6™-EPO that is secreted into the culture medium by human EPO-producing PER.C6™ cells is first roughly separated from cell debris and other contaminants by affinity column chromatography using monoclonal antibodies specific for human EPO. Thereafter, the purified EPO is subjected to a second chromatography procedure in which the EPO molecules carrying GalNAc-Lewis x structures are bound to a column containing the immobilized GalNAc-Lewis x specific monoclonal antibodies. EPO glycoforms that lack the GalNAc-Lewis x structures do not bind to the antibodies attached to the column and are collected in the flow-through. Bound EPO glycoforms carrying the GalNAc-Lewis x structures are eluted from the column at low pH or by using synthetic GalNAc-Lewis x as a competitor for binding to the GalNAc-Lewis x specific antibodies. EPO glycoforms carrying a high GalNAc-Lewis x content can be separately eluted from the column by increasing the concentration of GalNAc-Lewis x competitor step-wise or gradually during the elution. EPO glycoforms with a high GalNAc-Lewis x content are eluted at a higher concentration of GalNAc-Lewis x than EPO glycoforms possessing a low GalNAc-Lewis x content. Again, in accordance with the methods described above, also this method enables one to purify EPO from the culture medium by employing the specific characteristics of the post-translational modifications, such as Lewis x, lacdiNac or GalNac-Lewis x structures brought about by the cells in which the protein is produced. This does however, not imply that other modifications with the (predetermined) post-translational modifications cannot be employed for proper purification of the protein.

It will be understood by those of skill in the art, that although the invention has been illustrated with detailed examples concerning EPO, the present invention is not limited to production and/or purification of EPO with brain-type characteristics. Various other (human) therapeutic and/or diagnostic peptides and proteins, which may find use in treating disorders of the brain and other parts of the central- and peripheral nervous system and/or other ischemic/reperfusion damaged tissues, can be produced by means and methods of the present invention.

Example 17

EPO with a Low Sialic Acid Content has a Similar Potency as EPO with a High Sialic Acid Content in Reducing the Infarct Size After Middle Cerebral Artery Occlusion in Rats The effect of PER.C6™-EPO and Eprex on the size of a brain infarct, which was experimentally induced by the occlusion of the middle cerebral artery (MCA), was studied in F344/Ico male rats weighing 200-250 g, using a method similar to the method published by Siren et al., 2001. The right carotid artery of the animals was permanently occluded whereas the MCA was reversibly occluded for 60 min using a metal clip. Purified PER.C6™-EPO with an average sialic acid content of <6 sialic acids per molecule or Eprex (Jansen-Cilag; commercially available EPO) with an average sialic acid content >9 sialic acids per molecule) was applied intravenously at 5 min before the onset of the MCA occlusion at a dose of 5000 eU (ELISA units) per kg body weight. Notably, the sialic acid content of the PER.C6™-EPO preparation ranged from 0-9 sialic acids per molecule whereas Eprex contained more than 8 sialic acids per molecule. After a 60-min period, the occlusion was terminated by the removal of the metal clip surrounding the MCA. Reperfusion was observed microscopically after the removal of the clip. Twenty-four hr later the brains of the living rats were examined using MRI to reveal the Apparent Diffusion Coefficient (ADC) and T2 maps. These maps were used to quantify the infarct volumes (FIGS. 7A and 7B).

The results in FIGS. 7A and 7B show that rats treated with the PER.C6™-EPO and Eprex preparations displayed a similar reduction in the infarct size compared to the non-treated animals. Since the PER.C6™-EPO preparation has a much lower sialic acid content than the Eprex preparation this result demonstrates that a high sialic content is not essential for the neuroprotective activity of EPO in vivo.

Example 18

Determination of Half-life of EPO in Rats

To determine the half-life of Eprex in vivo, male Wag/Rij rats have been injected intravenously with 150 eU Eprex diluted in PBS/0.05% Tween-80 to a final volume of 500 µl. Just before the administration of the substrate, 200 µl of EDTA blood was sampled as negative control using the technique described in Lab. Animals 34, 372. At t=5, 15, 30, 60, 120, 180, 240, 300, 360, 420, 480, and 540 min after injection 200 µl EDTA blood was taken from the animals using the same technique. After the last blood sampling, the animals were sacrificed. The specimen was centrifuged at 760×g for 15 min at RT within 30 min of collection. The plasma samples were tested in an EPO specific Elisa (R&D) to determine the concentration of EPO in each sample.

As shown in FIG. 8, the decrease in the concentration of Eprex in the plasma displays a bi-phasic curve representing a distribution phase and a clearance phase. On basis of these results it can be estimated that Eprex had a half-life of about 180 min during the clearance phase. The half-life of PER.C6™-EPO is measured using the same protocol.

Example 19

The Effect of E1A Expression on the Glycosylation of EPO in HT1080 Cells

HT1080 cells were stably transfected with expression vectors encoding the adenovirus type 5 E1A (pIg.E1A.neo) or E1A+E1B (pIg.E1A.E1B; both plasmids described in U.S. Pat. No. 5,994,128) genes to determine the effect of the expression of the adenovirus type 5 E1A and/or E1A +E1B genes on glycosylation. To follow the glycosylation of a marker protein, the cells were co-transfected with an expression vector coding for EPO (pEPO2001/neo). Control HT1080 cells were transfected with the EPO expression vector only.

The transfection was performed with lipofectamine (Gibco) when the cells reached 70-90% confluency using 1.0 µg pE1A.neo or pE1A.E1B and 1.0 µg pEPO2001.neo per 7,85 cm² dish. Medium was replaced at day 2, 3, 7, 10 and 13 with selection medium containing DMEM, 1% NEAA (non-essential aminoacids, Invitrogen), 250 µg/ml Geneticin (Gibco) and 10% FBS. Preliminary experiments with stable E1A-transfected HT1080 cells revealed that E1A expression causes an altered morphology of the cells. In line with observations described by Frisch et al. (1991), we observed that a stable expression of the E1A gene induces a flat morphology. With this knowledge we made a rough selection for E1A expressing clones by picking flat clones. The clones were picked at day 14 and cultured in 24-wells plates with selection medium at 37° C./10% $CO_2$.

EPO-producing cells were selected on basis of the presence of EPO in the medium when the cells had reached sub-confluency. EPO was measured using an EPO-specific ELISA (Quantikine® IVD human EPO-ELISA, R & D systems). The EPO-producing cultures were scaled-up and analyzed for E1A expression. Therefore, the cells were lysed in lysis buffer (1% NP40, 0.5% deoxycholic acid, 0.5% SDS, 150 mM NaCl, 20 mM Tris-HCl, pH7.5) supplemented with 1 tablet Complete Mini proteinase inhibitors (Roche Diagnostics) per 10 ml. The lysates were cleared by centrifugation for 10 min at 14,000 g. Equal amounts (based on protein content) of the cleared cell lysates were electrophoresed under reducing conditions through a 10% BisTris gel (NuPAGE, Invitrogen). Proteins were thereafter transferred onto a PDVF membrane (P-Immobilon) using the Trans-Blot system of NuPAGE (Invitrogen). The blots were blocked for 1 hr or o/n at RT with 5% Protifar (Nutricia) in TBST, followed by an incubation with monoclonal mouse-anti-human E1A IgG2 (clone M73, Santa Cruz), diluted 1:400 in 5% Protifar/TBST, for 1 hr at RT or o/n at 4° C. The blots were washed with TBST and incubated with a peroxidase-conjugated goat anti-mouse IgG (Biorad), diluted 1:1000 in 5% Protifar/TBST, for 45 min at RT. After washing with TBST the blots were stained using the ECL plus system (Amersham Pharmacia Biotech). 55% of the EPO positive E1A clones and 68% of the EPO positive E1A.E1B clones revealed a clear expression of E1A (Table X). HT1080/E1A-EPO and HT1080/E1A.E1B-EPO clones that expressed E1A at a high level displayed a flat morphology (e.g. FIG. 11).

EPO was produced by HT1080/EPO, HT1080/E1A-EPO, and HT1080/E1A.E1B-EPO clones for glycan analysis. Therefore, the HT1080/E1A.EPO clone 008, the HT1080/E1A.E1B.EPO clone 072 and the HT1080/EPO clone 033 (Table X) was seeded at 175 cm² flasks at passage number (pn) 7. After 24 hrs, when cells reached a 60-80% confluency, selection medium was replaced by production medium (DMEM, 1% NEAA). This medium was harvested after 3 days and cells were lysed with lysis buffer. EPO was purified from the media according to example 2.

The N-linked glycans of the various EPO preparations were released by N-glycanase F treatment and subsequently analyzed by High Performance Anion Exchange Chromatography with Pulsed Amperometric Detection (HPAEC-PAD; Dionex). In this particular chromatography system the EPO derived glycan chains are separated under alkaline conditions on the basis of their charge. As demonstrated in FIG. 12, the glycans of EPO produced by the HT1080/E1A-EPO cells are less charged than those of EPO produced by the control HT1080/EPO cells, which indicates that EPO produced by the latter cells is more extensively sialylated than EPO produced by the E1A-expressing cells. More detailed information on the structure of the N-glycans was obtained by MALDI-MS analysis of the sugar chains of the EPO preparations. The N-linked glycans were released from the EPO preparations by N-glycanase F treatment and desialylated by neuraminidase treatment. The mass spectra of various representative EPO preparations are shown in FIG. 13. The GlycoMod software (WorldWideWeb.expasy.ch/tools/glycomod) was used to predict the sugar composition on basis of the observed mass (Table XI). The data show that the mass spectrum of the glycans of EPO produced by the control HT1080/EPO cells differs from those of EPO produced by the HT1080/E1A-EPO and HT1080/E1A.E1B-EPO cells. The mass spectra revealed that EPO produced by the latter cells possesses relatively less hexoses and relatively more deoxyhexoses compared to EPO produced by the control cells. In addition, glycan structures with a relatively low mass containing a relatively high amount of hexosamines and deoxyhexoses were found in EPO produced by the HT1080/E1A-EPO and HT1080/E1A.E1B-EPO cells. Some of these were absent in the EPO produced by the control cells. The mass profiles of the glycans of EPO produced by the E1A and E1A+E1B expressing HT1080 cells are similar to that of the glycans of EPO produced in PER.C6™ cells (see example 3) suggesting that the glycans of EPO produced by the former cells contain Lewis X and LacdiNAc structures, and structures that lack terminal galactoses. To confirm that EPO produced by the E1A and E1A+E1B expressing HT1080 cells contains more fucoses and GalNAc than the EPO produced by the control HT1080 cells a monosaccharide analysis was performed. Therefore, the N-linked glycans were released from the EPO preparations by N-glycanase F neuraminidase treatment, and thereafter hydrolyzed and analyzed by HPAEC-PAD. FIG. 14 shows the monosaccharide profiles of the EPO glycans, normalized for the amount of mannose. The data show that the N-linked glycans of EPO produced by the E1A and E1A+E1B expressing cells indeed possess relatively high amounts of fucose and GalNac.

The mass spectra and monosaccharide data strongly suggest that EPO produced by the E1A and E1A+E1B expressing cells contain multiple fucose residues. To support these data, the EPO preparations were treated with alpha-fucosidase (Almond meal) cleaving terminal alpha 1-3 and alpha 1-4 fucose residues. Thereafter, the samples were analyzed by Maldi-MS and the results were compared with the results obtained from EPO preparations that were not subjected to the alpha-fucosidase treatment. FIG. 15 shows that after the alpha-fucosidase treatment peaks that represent N-glycans with antennary fucoses decreased and peaks that are derived from these structures increased. For example, peaks with m/z values of ~2038 and ~2184 decreased, while the 1892 peak increased.

Collectively, the data show that the expression of adenovirus E1A alone or together with E1B can change the glycosylation profile of cells. The observation that the expression of E1A alone is sufficient for this change indicates that E1A is responsible for this change. The changes in glycosylation typically include the formation of Lewis x, LacdiNAc, and GalNAc-Lewis x structures. Many E1A and E1A+E1B expressing HT1080 cells have been characterized and the majority of these cells produced glycans that possess these characteristic glycan structures. Yet, the abundance of these structures, compared to the glycan structures that are produced by the HT1080 parental cells, varied (data not shown). The abundance of the glycan structures correlated largely to the expression level of E1A. This indicates that the extent to which the glycosylation profile is influenced by E1A is largely dependent on the level at which the E1A gene is expressed.

Example 20

Comparison of the Heamatopoietic Activity of PER.C6™-EPO and CHO-EPO at a High Dose The heamatopoietic activity of PER.C6™-EPO was determined in rats and compared with EPO derived from Chinese hamster ovary cells (CHO-EPO). Two CHO-EPO preparations were chosen; (1) Eprex (Jansen Cilag), which is a commercially available recombinant CHO-EPO with a high sialic acid content and (2) frCHO-EPO, a CHO-EPO preparation with a lower (similar to that of PER.C6™-EPO) sialic acid content (see FIG. 16), which was obtained by producing EPO by CHO cells and subsequent purification of these poorly sialylated isoforms by chromatographic methods as described in examples 2 and 3, and EP 0428267.

The study was performed with four groups of six WAG/Rij rats. A single dose of 5000 eU (ELISA units, as determined by the commercially available EPO-specific R&D Elisa Kit) per kg body weight Eprex, frCHO-EPO, PERC6-EPO or diluent buffer (as control) was injected intravenously in the penile vein. All EPO preparations were diluted to the proper concentration in diluent buffer (PBS, 0.03% Tween-80, 0.5% Glycine) in a total volume of 500 μl. After four days 250 μl EDTA blood was sampled by tongue puncture.

At the same day the blood samples were analyzed for the heamatocrit and the percentage of reticulocytes in the total red blood cell population using an automatic heamatocytometer.

The hematocrit levels were determined and expressed as a volume percentage of packed red cells, obtained by centrifuging of the blood (FIG. 17). The results demonstrate that PER.C6™-EPO and frCHO-EPO did not induce the hematocrit, whereas Eprex did.

As shown in FIG. 18, EPO induced a significant increase in reticulocyte counts compared to rats that received diluent buffer only. Eprex and frCHO-EPO displayed a similar stimulation; this stimulation was significantly higher ($p<0.001$) than in PERC6-EPO treated animals.

Evaluation of the RNA content in the reticulocytes allowed us to determine their degree of maturity. The immature reticulocyte fraction (IRF) is shown in FIG. 19. Eprex-treated rats revealed significantly higher percentages of immature reticulocytes compared to control rats. This indicates that the formation of reticulocytes stimulated by Eprex is still ongoing after four days of injection. This effect is less pronounced or absent in the frCHO-EPO and PER.C6™-EPO-treated rats, respectively (FIG. 19).

Collectively, the data show that all three EPO preparations induce the formation of reticulocytes; yet, the duration of the effect was the longest for Eprex and the shortest for PER.C6™-EPO while frCHO-EPO displayed an intermediate effect. This suggests that the low heamatopoietic effect of PER.C6™-EPO is not only due to its low sialic acid content but also due to other glycan features.

Example 21

Detailed Structure Analysis of the N-glycans of PER.C6™-EPO

Mass signals, obtained by mass spectrometry, cannot always be unambiguously assigned to a certain sugar structure, due to the fact that various isomeric structures may exist. To obtain further information on the structure of the N-linked glycans of PER.C6™-EPO, endo- and exoglycosidase treatments of the PER.C6™-EPO have been employed.

First, endoglycosidase F2 was used. This enzyme cleaves between the GlcNAc residues of the trimannosyl core of high mannose or bi-antennary complex type N-linked glycans (FIG. 20). In contrast to PNGase F, endoglycosidase F2 does not cleave tri- or tetra-antennary glycans and can thus be used to discriminate between bi- and tri-/tetra-antennary glycan structures. In FIG. 21 the MALDI spectra are presented of PER.C6™-EPO treated either with PNGase F or with endoproteinase F2. When comparing these spectra, it should be kept in mind that the glycans released by endoglycosidase F2 are smaller than glycans released by PNGase F. This is a difference of a GlcNAc and fucose residue (349 Da) and is due to the different cleavage sites of the enzymes (see FIG. 20).

All structures observed in a PNGase F digest at m/z>2185 are tri- or tetra-antennary structures, since none of these glycans is observed in the endoglycosidase F2 digest. Most structures at lower masses, i.e. m/z 1485, 1648, 1689, 1835, 1851, 1997, 2038, and 2185 have a corresponding peak in the endoglycosidase F2 digest and are bi-antennary. It is possible that also some isomeric tri- or tetra-antennary structures are present, but this is not much since peak ratios in both spectra in FIG. 21 are largely comparable. The spectrum of the endoglycosidase F2 digest lacks the peaks corresponding to m/z 1892 and 2054 in the PNGase F spectrum. This proves that these peaks represent glycans that are not bi-antennary, but instead tetra-antennary without or with one galactose residue, respectively. These data confirm that PER.C6™-EPO contains glycans with terminal GlcNAc.

Next, exoglycosidases were used to further investigate the N-glycan structures. Glycans were released from PER.C6™-EPO by PNGase F and desialylated using neuraminidase. Subsequently, the samples were treated with different combinations of the following exoglycosidases:

1) β-galactosidase, which cleaves non-reducing, terminal Galβ1-4GlcNAc (and Galβ1-4GalNAc and at higher enzyme ratios Galβ1-3 linkages).
2) Bovine kidney α-fucosidase, which cleaves α1-2,3,4 and 6 linked fucose from N- and O-glycans. It cleaves α1-6 linked fucose on the trimannosyl core of N-linked glycans more efficiently than other α-fucose linkages.
3) Almond meal α-fucosidase, which cleaves non-reducing, terminal α1-3 or α1-4 fucosidase residues.
4) β-N-Acetylglucosaminidase (GlcNAc-ase), which cleaves non-reducing, terminal β1-2,3,4,6-linked N-acetylglucosamine from complex carbohydrates. It does not cleave N-acetylgalactosamine residues.

The linkage-types expected on PER.C6™-EPO glycans are shown in FIG. 22. The galactosidase and fucosidase incubations were performed simultaneously, i.e., during fucosidase incubation still active galactosidase was present. Further GlcNAc-ase treatments were performed when galactosidase and fucosidase had lost their activity.

In FIG. 23 the results are presented for the galactosidase treatment. In this figure the m/z values and relative intensities are given of all peaks in the spectrum, which have a relative intensity (i.e., height of peak divided by the summarized heights of all peaks) of 5% or higher. The proposed glycan structures are indicated as well. The peaks that were assigned to galactosylated structures had shifted after galactosidase treatment, albeit not always complete. It was found that the galactosidase does not release galactose when a fucose is present on the adjacent GlcNAc residue. Some tri-antennary glycans seemed to appear after the galactosidase treatment (m/z 1689). This was caused by contaminating GlcNAc-ase, which was demonstrated to be present in the galactosidase preparation using standard glycans (data not shown).

The galactosidase-treated glycans were then subjected to fucosidase treatment (FIGS. 24 and 26). In case of bovine kidney fucosidase, this resulted in a 146 Da shift of all peaks in the spectrum. This is the mass of a fucose residue. Since this fucosidase preferably cleaves α1-6 linked fucose residues, and since all peaks lose only one 146 Da-unit, this indicates that all glycans contained a core fucose.

The galactosidase-treated glycan pool that was subsequently incubated with almond meal fucosidase gave a relative simple spectrum (FIGS. 25 and 26). All fucose residues were removed from the antennae, leaving only singly (core) fucosylated glycans. The remaining terminal galactose residues were also removed because the galactosidase was still active during the fucosidase incubation. After GlcNAc-ase treatment of the de-fucosylated glycans only four peaks were left. The major peak was observed at m/z 1079 and represents the fucosylated trimannosyl core. The peaks at m/z 1485 and m/z 1891 confirm the presence of GalNAc residues in the antenna, since this residue is not removed by the GlcNAc-ase. The peak at m/z 1444 proves the presence of lactosamine repeats: the galactose must have been shielded by a GlcNAc during galactosidase treatment.

REFERENCES

Anchord D T, Brot F E, Bell C E and Sly W S (1978) Human beta-glucuronidase: in vivo clearance and in vivo uptake by a glycoprotein recognition system on reticuloendothelial cells. Cell 15:269

Barbone A G, Aparicio B, Anderson D W, Natarajan J and Ritchie D M (1994) Reticulocyte measurements as a bioassay for erythropoietin. J Pharm Biomed Anal 12:515-522

Brines M L, Ghezzi P, Keenan S, Agnello D, De Lanerolle N C, Cerami C, Itri L M and Cerami A (2000) Erythropoietin crosses the blood-brain barrier to protect against experimental brain injury. Proc Natl Acad Sci USA 97:10526-10531

Buemi M, Allegra A, Corica F, Floccari F, D'Avella D, Aloisi C, Calapai G, Iacopino G and Frisina N (2000) Intravenous recombinant erythropoietin does not lead to an increase in cerebrospinal fluid erythropoietin concentration. Nephrol Dial Transplant 15:422-423

Buerke N, Weyrich A S, Zheng Z, Gaeta F C A, Forrest M J and Lefer A M (1994) Sialyl Lewis$^x$-containing oligosaccharide attenuates myocardial reperfusion injury in cats. J Clin Invest 93:1140-1148

Chikuma M, Masuda S, Kobayashi T, Nagao M and Sasaki R (2000) Tissue-specific regulation of erythropoietin production in the murine kidney, brain, and uterus. Am J Physiol Endocrinol Metab 279:E1242-E1248

Dame C, Juul S E and Christensen R D (2001) The biology of erythropoietin in the central nervous system and its neurotrophic and neuroprotective potential. Biol Neonate 79:228-235

Foxall C S, Watson S R, Dowbenko D, Fennie C, Lasky L A et al. (1992) The three members of the selectin receptor family recognize a common carbohydrate epitope: the sialyl Lewis$^x$ oligosaccharide. J Cell Biol 117:895-902

Goto M, Akai K, Murakami A, Hashimoto C, Tsuda E, Ueda M, Kawanishi G, Takahashi N, Ishimoto A, Chiba H and Sasaki R (1988) Production of recombinant erythropoietin in mammalian cells: host-cell dependency of the biological activity of the cloned glycoprotein. Bio/Technology 6:67-71

Grinnell B W, Hermann R B, Yan S B (1994) Human Protein C inhibits selectin-mediated cell adhesion: role of unique fucosylated oligosaccharide. Glycobiol 4: 221-225.

Hoffmann A, Nimtz M, Wurster U and Conradt H S (1994) Carbohydrate structures of β-trace protein from human cerebrospinal fluid: evidence for "brain-type" N-glycosylation. J Neurochem 63:2185-2196

Hoffmann A, Nimtz M, Getzlaff R and Conradt H S (1995) brain-type N-glycosylation of asialo-transferrin from human cerebrospinal fluid. FEBS Lett 359:164-168

Ireland W P and MacLeod W S (1993) A method for finding stereotaxic coordinates from brain sections. J Neurosci Methods 49:93-96

Jourdian G W, Dean L and Roseman S (1971). The sialic acids. XI. A periodate-resorcinol method for the quantitative estimation of free sialic acids and their glycosides.

Juul S E, Harcum J, Li Y and Christensen R D (1997) Erythropoietin is present in the cerebrospinal fluid of neonates. J Pediatr 130:428-430

Konishi Y, Chui D-H, Hirose H, Kunishita T and Tabari T (1993) Trophic effect of erythropoietin and other hematopoietic factors on central cholinergic neurons in vitro and in vivo. Brain Res 609:29-35

Koretz B, Von B Ahern K, Wang N, Lustig H S and Greenberg D A (1994) Pre- and postsynaptic modulators of excitatory neurotransmission: comparative effects on hypoxia/hypoglycemia in cortical cultures. Brain Res 643:334-337

Lou J, Dayer J-M, Grau G E and Burger D (1996) Direct cell/cell contact with stimulated T lymphocytes induces the expression of cell adhesion molecules and cytokines by human brain microvascular endothelial cells. Eur J Immunol 26:3107-3113

Margolis R U and Margolis R K (1989) Neurobiology of glycoconjugates. Plenum Press, New York Marti H H, Gassmann M, Wenger R H, Kvietikova I, Morganti-Kossmann C, Kossmann T, Trentz O and Bauer C (1997) Detection of erythropoietin in human liquor: intrinsic erythropoietin in the brain. Kidney Int 51:416-418

Masland R H (2001) The fundamental plan of the retina. Nat Neurosci 4:877-886

Masuda S, Nagao M and Sasaki R (1999) Erythropoietic, neurotrophic, and angiogenic functions of erythropoietin and regulation of erythropoietin production. Int J Hematol 70:1-6

Misaizu T, Matsuki S, Strickland T W, Takeuchi M, Kobata A and Takasaki S (1995) Role of antennary structure of N-linked sugar chains in renal handling of recombinant human erythropoietin. Blood 86:4097-4104

Morimoto K, Tsuda E, Said A A, Uchida E, Hatakeyama S, Ueda M and Hayakawa T (1996) Biological and physicochemical characterization of recombinant human erythropoietins fractionated by Mono Q column chromatography and their modification with sialyltransferase. Glycoconjugate J 13:1013-1020

Nagayama T, Sinor A D, Simon R P, Chen J, Graham S, Jin K and Greenberg D A (1999) Cannabinoids and neuroprotection from global and focal cerebral ischemia and in vitro. J Neurosci 19:2987-2995

Nimtz M, Martin W, Wray V, Klöppel K-D, Augustin J and Conradt H S (1993) Structures of sialylated oligosaccharides of human erythropoietin expressed in recombinant BHK-21 cells. Eur J Biochem 213:39-56

Rahbek-Nielsen H, Roepstorff P, Reischl H, Wozny M, Koll H and Haselbeck A (1997) Glycopeptide profiling of human urinary erythropoietin by matrix-assisted laser desorption/ionization mass spectrometry. J Mass Spectrom 32:948-958

Sadamoto Y, Igase K, Sakanaka M, Sato K, Otsuka H, Sakaki S, Masuda S and Sasaki R (1998) Erythropoietin prevents place navigation disability and cortical infarction in rats with permanent occlusion of the middle cerebral artery. Biochem Biophys Res Commun 253:26-32

Sasaki R, Masuda S and Nagao M (2001) Pleiotropic functions and tissue-specific expression of eryhtropoietin. News Physiol Sci 16:110-113

Simpson P and Savion S (1982) Differentiation of rat myocytes in single cell cultures with and without proliferating nonmyocardial cells Circ Res 50:101-116

Sirén A-L, Fratelli M, Brines M, Goemans C, Casagrande S, Lewczuk P, Keenan S, Gleiter C, Pasquali C, Capobianco A, Mennini T, Heumann R, Cerami A, Ehrenreich H and Ghezzi P (2001) Erythropoietin prevents neuronal apoptosis after cerebral ischemia and metabolic stress. Proc Natl Acad Sci USA 98:4044-4049

Stahl P D, Rodman J S, Miller M J and Schlesinger P H (1978) Evidence for receptor-mediated binding of glycoproteins, glycoconjugates, and lysosomal glycosidases by alveolar macrophages. Proc Natl Acad Sci USA 75:1399

Storring P L and Gaines Das R E (1992) The international standard for recombinant DNA-derived erythropoietin:

collaborative study of four recombinant DNA-derived erythropoietins and two highly purified human urinary erythropoietins. J. Endocrinol. 134: 459-484

Takeuchi M, Takasaki S, Miyazaki H, Kato T, Hoshi S, Kochibe N and Kobata A (1988) Comparative study of the asparagine-linked sugar chains of human erythropoietins purified from urine and the culture medium of recombinant Chinese hamster ovary cells. J Biol Chem 263:3657-3663

Takeuchi M, Inoue N, Strickland T W, Kubota M, Wada M, Shimizu R, Hoshi S, Kozutsumi H, Takasaki S, and Kobata A (1989) Relationship between sugar chain structure and biological activity of recombinant human erythropoietin produced in Chinese hamster ovary cells. Proc Natl Acad Sci USA 86:7819-7822

Takeuchi M and Kobota A (1991) Structures and functional roles of the sugar chains of human erythropoietins. Glycobiol 1:337-346

Toyoda T, Itai T, Arakawa T, Aoki K H and Yamaguchi H (2000) Stabilization of human recombinant erythropoietin through interactions with the highly branched N-glycans. Japan Biochem Soc 128:731-737

Tsuda E, Goto M, Murakami A, Akai K, Ueda M, Kawanishi G, Takahashi N, Sasaki R, Chiba H, Ishihara H, Mori M, Tejima S, Endo S and Arata Y (1988) Comparative structural study of N-linked oligosaccharides of urinary and recombinant erythropoietins. Biochemistry 7:5646-5654

Tsuda E, Kawanishi G, Ueda M, Masuda S and Sasaki R (1990) The role of carbohydrate in recombinant human erythropoietin. Eur J Biochem 188:405-411

Van den Nieuwenhof I M, Koistinen H, Easton R L, Koistinen R, Kamarainen M, Morris H R, Van Die I, Seppala M, Dell A and Van den Eijnden D H (2000) Recombinant glycodelin carrying the same type of glycan structures as contraceptive glycodelin-A can be produced in human kidney 293 cells but not in chinese hamster ovary cells. Eur J Biochem 267:4753-62

Van Eijk H G, Van Noort W L, Dubelaar M-L and Van der Heul C (1983) The microheterogeneity of human serum transferrins in biological fluids. Clin Chim Acta 132:167-172

Van Reemoortere A, Hokke C H, Van Dam G J, Van Die I, Deelder A M and Van den Eijnden D H (2000) Various stages of Schistosoma express Lewis x, LacdiNAc, GalNAcβ1-4(Fucα1-2Fucα1-3) GlcNAc carbohydrate epitopes: detection with monoclonal antibodies that are characterized by enzymatically synthesized neoglycoproteins. Glycobiol 10:601-609

Wasley L C, Timony G, Murtha P, Stoudemire J, Dorner A J, Caro J, Krieger M and Kaufman R J (1991) The importance of N- and O-linked oligosaccharides for the biosynthesis and in vitro and in vivo biological activities of erythropoietin. Blood 77:2624-2632

Watson E, Bhide A and Van Halbeek H (1994) Structure determination of the intact major sialylated oligosaccharide chains of recombinant human erythropoietin expressed in Chinese hamster ovary cells. Glycobiol 4:227-237

White M J, DiCaprio M J and Greenberg D A (1996) Assessment of neuronal viability with Alamar blue in cortical and granule cell cultures. J Neurosci Meth 70:195-200

Wiessner C, Allegrini P R, Ekatodramis D, Jewell U R, Stallmach T and Gassmann M (2001) Increased cerebral infarct volumes in polyglobulic mice overexpressing erythropoietin. J Cereb Blood Flow Metab 21:857-864

Wong D, Prameya R and Dorovini-Zis K (1999) In vitro adhesion and migration of T lymphocytes across monolayers of human brain microvessel endothelial cells: regulation by ICAM-1, VCAM-1, E-selection and PECAM-1. J Neuropath Exp Neurology 58:138-152

TABLE I

| Marker protein | Description |
| --- | --- |
| Pan-keratin | Detection of almost all cytokeratins. Labels keratinized and corneal epidermis, stratified squamous epithelia of internal organs, stratified epithelia, hyperproliferative keratinocytes, and simple epithelia. |
| EMA | Epithelial membrane antigen. Labels normal and neoplastic epithelium. |
| S100 | EF-band type $Ca^{2+}$ binding proteins. Expressed in neural tissues and other tissues. |
| Vimentin | Cytoskeletal intermediate filaments (=structural protein). Is a general marker of cells originating in the mesenchyme. Expressed during skeletal muscle development. |
| Desmin | Cytoskeletal intermediate filaments (=structural protein). Expressed during skeletal muscle development. |
| s.m. actin | Smooth muscle cell actin. Stains smooth muscle cells and myo-epithelial cells. |
| Synaptophysin | Reacts with neuroendocrine cells. |
| Chromogranin | Acidic glycoproteins that are widely expressed within secretory granules of endocrine, neuroendocrine and neural tissue. |
| NSE | Neuron specific enolase. Labels cells of neural and neuroendocrine origin |
| Neurofilament | Reacts with phosphorylated neurofilament protein and Labels neural processes and pheripheral nerves as well as symphataetic ganglion cells and adrenal medulla. |
| GFAP (polycon) | Glial Fibrillary Acidic Protein. GFAP is specifically found in astroglia, which are highly responsive to neurologic insults. Astrogliosis is found to be a result of mechanical trauma, AIDS dementia and prion infection and is accompanied by an increase in GFAP expression. Immunohistochemical marker for localizing benign astrocyte and neoplastic cells of glial origin in the central nervous system. |
| CD31 | Reacts with PECAM-1. Present on platelets, monocytes, granulocytes, lymphocytes, endothelial cells. |
| CD34 | Recognizes O-glycosylated transmembrane glycoprotein. Expressed on hemopoietic stem cells, vascular EC, embryonic fibroblasts, some cells in fetal adult nerve tissue. |
| N-CAM | Neuronal cell adhesion molecules. N-CAM is involved in cell-cell interactions during growth. |

TABLE II

| Marker protein | Control tissue |
| --- | --- |
| Pan-keratin | Colon carcinoma |
| EMA | Colon carcinoma |
| S100 | Pancreas |
| Vimentin | Tonsil |
| Desmin | Colon |
| s.m. actin | Tonsil |
| Synaptophysin | Pancreas |
| Chromogranin | Pancreas |
| NSE | Pancreas |
| Neurofilament | Colon |
| GFAP (polycon) | Brain |
| CD31 | Colon |
| CD34 | Tonsil |
| N-CAM (CD56) | Colon |

TABLE III

| Marker protein | Supplier | Antibody | Catalog nr | Antibody dilution |
|---|---|---|---|---|
| Pan-keratin | Biogenex | Mouse IgG1 | MU071-UC | 1:200 |
| EMA | Dako | Mouse IgG2a | M0613 | 1:50 |
| S100 | Dako | Rabbit | Z0311 | 1:3000 |
| Vimentin | Biogenex | Mouse IgG1 | MU074-UC | 1:3200 |
| Desmin | Sanbio | Mouse IgG | MON 3001 | 1:50 |
| s.m. actin | Biogenex | Mouse IgG2a | MU128-UC | 1:150 |
| Synaptophysin | Dako | Mouse IgG1 | M0776 | 1:50 |
| Chromogranin | Biogenex | Mouse IgG1 | MU126-UC | 1:150 |
| NSE | Dako | Mouse IgG1 | M0873 | 1:250 |
| Neurofilament | Sanbio | Mouse IgG | MON3004 | 1:300 |
| GFAP (polycon) | Dako | Mouse IgG1 | M0761 | 1:200 |
| CD31 | Dako | Mouse IgG1 | M0823 | 1:60 |
| CD34 | Biogenex | Mouse IgG1 | MU236-UC | 1:20 |
| N-CAM (CD56) | Neomarkers | Mouse IgG1 | MS.204.P | 1:10 |

TABLE IV

| Marker protein | Score |
|---|---|
| Pan-keratin | Negative |
| EMA | Negative |
| S100 | Negative |
| Vimentin | Positive |
| Desmin | Negative |
| s.m. actin | Negative |
| Synaptophysin | Positive |
| Chromogranin | Negative |
| NSE | Negative |
| Neurofilament | Positive |
| GFAP (polycon) | Positive |
| CD31 | Negative |
| CD34 | Negative |
| N-CAM (CD56) | Positive |

TABLE V

| Clone and culture conditions | Molar ratio of neutral monosaccharides normalized to three mannose residues | | | | |
|---|---|---|---|---|---|
| | Man | Fuc | GalNAc | GlcNAc | Gal |
| P8 - DMEM | 3 | 0.5 (0.9) | 0.4 (0.4) | 2.2 (2.7) | 1.7 (1.3) |
| P8 - JRH | 3 | 1.5 (1.4) | 0.7 (0.8) | 6.1 (6.4) | 3.5 (3.9) |
| P7 - DMEM | 3 | 1.5 (1.4) | 0.4 (0.3) | 5.5 (6.1) | 2.3 (3.3) |
| P7 - JRH | 3 | 1.8 (1.7) | 0.4 (0.4) | 6.1 (6.8) | 3.6 (4.2) |
| C25 - DMEM | 3 | 2.0 | 1.0 | 6.0 | 2.2 |
| Eprex | 3 | 0.7 | — | 5.4 | 4.1 |

TABLE VI

| P7 | Percentage of total | | | Ratio |
|---|---|---|---|---|
| Mass (m/z) | Pool A | Pool B | Pool C | Hex:HexNAc:dHex |
| 1809.64 | 2.34 | 2.99 | 2.44 | 5:4:1 |
| 1850.67 | 2.57 | 5.31 | 2.49 | 4:5:1 |
| 1891.69 | 5.06 | 10.39 | 1.31 | 3:6:1 |
| 1955.70 | — | 1.95 | 2.16 | 5:4:2 |
| 1996.72 | 6.37 | 7.96 | 6.38 | 4:5:2 |
| 2037.75 | 6.33 | 5.16 | 5.39 | 3:6:2 |
| 2053.74 | 3.70 | 4.11 | 1.98 | 5:5:1 |
| 2142.78 | 2.19 | 3.68 | 2.45 | 4:5:3 |
| 2174.77 | 6.53 | 3.63 | 8.04 | 6:5:1 |
| 2183.81 | 6.69 | 5.02 | 7.57 | 3:6:3 |
| 2199.80 | 3.78 | 4.65 | 1.58 | 4:6:2 |
| 2215.80 | 4.13 | 4.95 | 4.15 | 5:6:1 |
| 2256.82 | — | 1.30 | | 4:7:1 |
| 2320.83 | 2.34 | 2.04 | 3.29 | 6:5:2 |
| 2361.86 | 4.35 | 3.30 | 3.23 | 5:6:2 |
| 2377.85 | 3.77 | 3.79 | 2.86 | 6:6:1 |
| 2507.91 | 1.62 | 2.32 | 1.32 | 5:6:3 |
| 2523.91 | 2.09 | 2.60 | 1.61 | 6:6:2 |
| 2539.90 | 11.89 | 4.81 | 19.32 | 7:6:1 |
| 2580.93 | 3.32 | 1.53 | 1.69 | 6:7:1 |
| 2612.94 | — | — | 1.78 | 6:5:3 |
| 2669.97 | 1.95 | 2.34 | — | 6:6:3 |
| 2685.96 | 6.21 | 3.11 | 5.81 | 7:6:2 |
| 2726.99 | 1.62 | 1.38 | 1.36 | 6:7:2 |
| 2832.02 | 3.64 | 1.55 | 3.08 | 7:6:3 |
| 2905.04 | 1.79 | — | 2.45 | 8:7:1 |
| 2978.08 | 2.23 | 1.65 | — | 7:6:4 |

TABLE VII

| P8 | Percentage of total | | | Ratio |
|---|---|---|---|---|
| Mass (m/z) | Pool A | Pool B | Pool C | Hex:HexNAc:dHex |
| 1809.64 | — | 1.03 | — | 5:4:1 |
| 1850.67 | 3.36 | 2.05 | — | 4:5:1 |
| 1891.69 | 5.11 | 2.11 | 3.04 | 3:6:1 |
| 1955.70 | 1.46 | 1.22 | 1.08 | 5:4:2 |
| 1996.72 | 5.05 | 4.61 | 6.54 | 4:5:2 |
| 2012.72 | 1.34 | 1.38 | 1.35 | 5:5:1 |
| 2037.75 | 14.62 | 14.34 | 12.48 | 3:6:2 |
| 2053.74 | 3.73 | 2.76 | 4.29 | 4:6:1 |
| 2142.78 | 2.57 | 1.97 | 2.06 | 4:5:3 |
| 2158.78 | 1.43 | 1.91 | — | 5:5:2 |
| 2174.77 | 2.40 | 2.53 | 5.58 | 6:5:1 |
| 2183.81 | 16.91 | 15.79 | 14.90 | 3:6:3 |
| 2199.80 | 1.74 | 3.18 | 4.90 | 4:6:2 |
| 2215.80 | 4.23 | 4.20 | 3.08 | 5:6:1 |
| 2256.82 | 2.08 | 3.04 | 2.17 | 4:7:1 |
| 2320.83 | 1.67 | 1.88 | 2.23 | 6:5:2 |
| 2361.86 | 3.25 | 2.25 | 3.02 | 5:6:2 |
| 2377.85 | 1.50 | 1.84 | 2.73 | 6:6:1 |
| 2402.88 | 2.05 | 2.20 | 4.26 | 4:7:2 |
| 2418.88 | 0.97 | 1.54 | — | 5:7:1 |
| 2466.89 | 1.03 | — | — | 6:5:3 |
| 2507.91 | 2.04 | 2.48 | — | 5:6:3 |
| 2523.91 | 1.58 | 1.73 | 1.47 | 6:6:2 |
| 2539.90 | 2.48 | 4.79 | 9.56 | 7:6:1 |
| 2548.94 | 1.26 | 1.14 | 0.66 | 4:7:3 |
| 2580.93 | 1.87 | 2.07 | 2.48 | 6:7:1 |
| 2685.96 | 2.74 | 3.39 | 4.30 | 7:6:2 |
| 2726.99 | 2.55 | 3.12 | — | 6:7:2 |
| 2768.01 | 1.35 | — | — | 5:8:2 |
| 2832.02 | 2.14 | 3.06 | 1.91 | 7:6:3 |
| 2873.05 | 1.70 | 1.81 | 1.63 | 6:7:3 |
| 2889.04 | 1.14 | 0.67 | — | 7:7:2 |
| 2978.08 | 0.89 | 0.99 | 2.39 | 7:6:4 |
| 3019.10 | 1.09 | 1.26 | — | 6:7:4 |

TABLE VIII

| | FT activities (nmol/hr/mg protein) | | | |
|---|---|---|---|---|
| | α1,2 FT | α1,3 FT | α1,6 FT | GalT |
| CHO | <0.01 | 0.03 | 4.31 | 12.5 |
| PER.C6 | <0.01 | 0.65 | 3.62 | 3.41 |

TABLE IX

| Mass (m/z) | Hex | HexNAc | dHex | Fraction 1 | Fraction 2 | Fraction 3 | Fraction 4 |
|---|---|---|---|---|---|---|---|
| 1631.6 | 3 | 4 | 2 | ND | ND | ND | 1.16 |
| 1688.6 | 3 | 5 | 1 | 3.22 | 3.09 | 2.22 | 2.82 |
| 1793.7 | 4 | 4 | 2 | 1.29 | 1.15 | ND | 0.83 |
| 1809.6 | 5 | 4 | 1 | ND | 1.50 | 2.10 | 2.82 |
| 1834.7 | 3 | 5 | 2 | 1.71 | 1.77 | 1.73 | 1.41 |
| 1891.7 | 3 | 6 | 1 | 10.98 | 7.96 | 5.19 | 4.31 |
| 1955.7 | 5 | 4 | 2 | 0.86 | 3.36 | 0.87 | 1.33 |
| 1996.7 | 4 | 5 | 2 | 2.40 | 2.65 | 2.47 | 2.32 |
| 2037.8 | 3 | 6 | 2 | 4.03 | 4.86 | 4.82 | 3.65 |
| 2053.7 | 5 | 5 | 1 | 6.43 | 5.39 | 3.89 | 2.65 |
| 2101.8 | 5 | 4 | 3 | 1.29 | 1.55 | ND | DN |
| 2142.8 | 4 | 5 | 3 | 1.71 | 2.03 | 1.36 | 2.98 |
| 2174.8 | 6 | 5 | 1 | 1.29 | 1.95 | 1.36 | 0.00 |
| 2183.8 | 3 | 6 | 3 | 8.57 | 11.05 | 16.44 | 22.54 |
| 2199.8 | 4 | 6 | 2 | 4.54 | 5.04 | 4.94 | 3.81 |
| 2215.8 | 5 | 6 | 1 | 5.66 | 4.60 | 2.84 | 2.32 |
| 2256.8 | 4 | 7 | 1 | 1.97 | 1.77 | 0.87 | 1.33 |
| 2320.8 | 6 | 5 | 2 | 1.03 | 1.27 | 0.87 | 1.49 |
| 2361.9 | 5 | 6 | 2 | 4.46 | 4.86 | 4.39 | 3.31 |
| 2377.9 | 6 | 6 | 1 | 5.23 | 2.21 | 2.10 | 1.66 |
| 2507.9 | 5 | 6 | 3 | 1.65 | 1.68 | 3.71 | 5.47 |
| 2523.9 | 6 | 6 | 2 | 3.43 | 2.21 | 2.22 | 1.82 |
| 2539.9 | 7 | 6 | 1 | 10.72 | 6.19 | 4.94 | 4.47 |
| 2580.9 | 6 | 7 | 1 | 2.14 | 2.21 | 1.85 | 1.16 |
| 2670.0 | 6 | 6 | 3 | 0.86 | 1.68 | 2.47 | 2.82 |
| 2686.0 | 7 | 6 | 2 | 6.69 | 6.90 | 5.93 | 3.81 |
| 2727.0 | 6 | 7 | 2 | 2.70 | 3.36 | 2.72 | 1.82 |
| 2832.0 | 7 | 6 | 3 | 2.83 | 4.60 | 6.43 | 3.81 |
| 2873.1 | 6 | 7 | 3 | 1.29 | 1.55 | 4.57 | 2.98 |
| 2978.1 | 7 | 6 | 4 | 1.03 | 1.55 | 3.58 | 3.73 |
| 3019.1 | 6 | 7 | 4 | ND | ND | 2.47 | 2.90 |
| 3124.1 | 7 | 6 | 5 | ND | ND | 0.62 | 2.49 |

TABLE X

| | Clone | Morphology | E1A expression |
|---|---|---|---|
| E1A.EPO clones | 004 | Flat | ++ |
| | 008* | Flat | ++ |
| | 025 | Flat | +++ |
| | 028 | Small needles | − |
| | 034 | Flat | ±− |
| | 056 | Flat + parental | − |
| | 062 | Flat | +++ |
| | 066 | Flat | ++ |
| | 076 | Parental | − |
| E1A.E1B.EPO clones | 002 | Flat | ++ |
| | 003 | Flat + parental | ++ |
| | 005 | Flat | ++ |
| | 023 | Flat | +++ |
| | 025 | Flat + parental | − |
| | 026 | Flat | +++ |
| | 028 | Flat + parental | + |
| | 031 | Flat | + |
| | 033 | Flat | +++ |
| | 035 | Parental | − |
| | 049 | Flat | ++ |
| | 051 | Flat + parental | + |
| | 057 | Flat, irregular | + |
| | 058 | Flat | ++ |
| | 062 | Flat | ++ |
| | 067 | Flat | ++ |
| | 072* | Flat, irregular | ++ |
| | 076 | Flat | +++ |
| | 077 | Flat | +++ |

TABLE XI

| [M + Na] + | 1647.6 | 1809.6 | 1891.7 |
|---|---|---|---|
| HexNAc | 2 | 2 | 4 |
| Hex | 1 | 2 | |
| dHex | | | |

TABLE XI-continued
| Proposed structure | 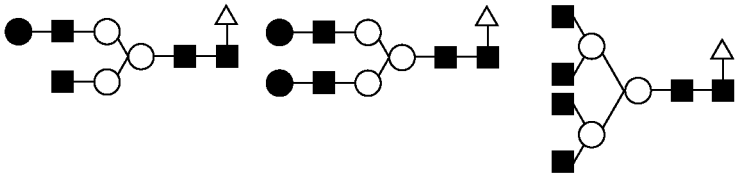 | 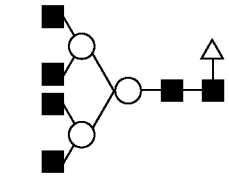 | 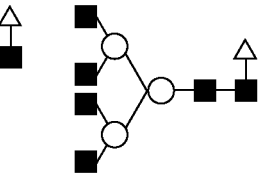 |
|---|---|---|---|
| Clone 033 | | | |
| Clone 008 | 2% | 2% | |
| Clone 072 | | 1% | 6% |
| Other possible stucture | | | 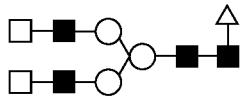 |
| | | | |
|---|---|---|---|
| [M + Na]+ | 1996.7 | 2037.8 | 2174.8 |
| HexNAc | 3 | 4 | 3 |
| Hex | 1 | | 3 |
| dHex | 1 | 1 | |
| Proposed structure | 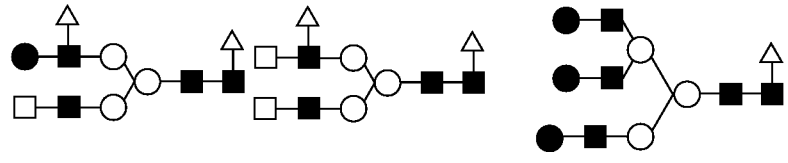 | 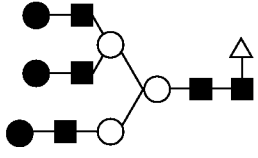 | 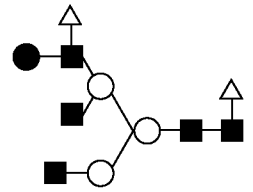 |
| Clone 033 | | | 11% |
| Clone 008 | 1% | 4% | 4% |
| Clone 072 | 2% | 9% | 4% |
| Other possible stucture | 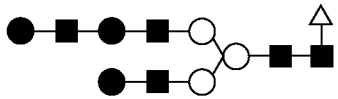 | | 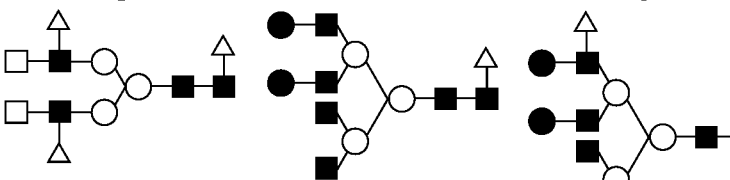 |
| | | | |
|---|---|---|---|
| [M + Na]+ | 2183.8 | 2215.8 | 2361.9 |
| HexNAc | 4 | 4 | 4 |
| Hex | 2 | 2 | 2 |
| dHex | 2 | | 1 |
| Proposed structure | 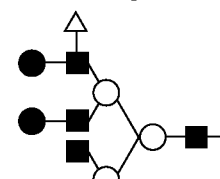 | 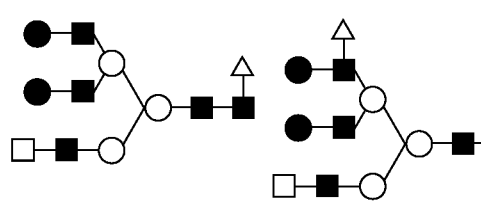 | 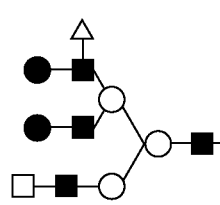 |
| Clone 033 | | | |
| Clone 008 | 8% | 4% | 3% |
| Clone 072 | 8% | 2% | 2% |
| Other possible stucture | | 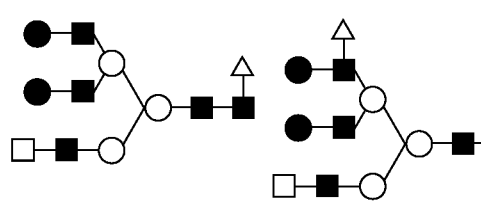 | 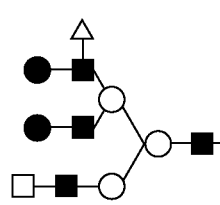 |
| | | | | |
|---|---|---|---|---|
| [M + Na]+ | 2377.9 | 2402.9 | 2539.9 | 2580.9 |
| HexNAc | 4 | ? | 4 | 5 |
| Hex | 3 | | 4 | 3 |
| dHex | | | | |

TABLE XI-continued

| | Col A | Col B | Col C |
|---|---|---|---|
| Proposed structure | (structure) | (structure) | (structure) |
| Clone 033 | 3% | 78% | |
| Clone 008 | 3% | 28% | 6% |
| Clone 072 | 3% | 26% | 11% |
| [M + Na] + | 2686.0 | 2727.0 | 2832.0 |
| HexNAc | 4 | 5 | 4 |
| Hex | 4 | 3 | 4 |
| dHex | 1 | 1 | 2 |
| Proposed structure | (structure) | (structure) | (structure) |
| Clone 033 | 4% | | |
| Clone 088 | 14% | 6% | 8% |
| Clone 072 | 9% | 7% | 6% |
| [M + Na] + | | 2873.1 | 2905.0 |
| HexNac | | 5 | 5 |
| Hex | | 3 | 5 |
| dHex | | 2 | |
| Proposed structure | | (structure) | (structure) |
| Clone 033 | | | 4% |
| Clone 008 | | 3% | 3% |
| Clone 072 | | 3% | 2% |

The invention claimed is:

1. A method for the therapeutic treatment of a disorder selected from the group consisting of cerebral ischemia and myocardial infarction, said method comprising:
   administering to a human or animal subject suffering from or at risk of suffering from cerebral ischemia or myocardial infarction a composition comprising erythropoietin molecules, wherein said composition of erythropoietin molecules has an average number of Lewis-X structures on N-linked glycans per erythropoietin molecule of at least 2.7.

2. A method for purifying an erythropoietin having at least one N-linked glycan comprising a Lewis X structure, said method comprising:
   expressing a nucleic acid encoding said erythropoietin in a mammalian cell, wherein the mammalian cell expresses a nucleic acid encoding E1A from an adenovirus,
   purifying the expressed erythropoietin, said purifying comprising a step of binding of the expressed erythropoietin to a lectin or to a monoclonal antibody that binds to N-linked glycans comprising Lewis X structures, and
   fractionating the expressed erythropoietin based on the Lewis X content to obtain a composition containing an average number of Lewis-X structures on N-linked glycans per erythropoietin molecule of at least 2.7.

3. The method according to claim 2, comprising a step of binding of the expressed erythropoietin to an AAL lectin.

4. The method according to claim 2, wherein said mammalian cell is obtained from a cell deposited under No. 96022940 at the European Collection of Animal Cell Cultures at the Center for Applied Microbiology and Research.

* * * * *